(12) United States Patent
Itskovitz-Eldor et al.

(10) Patent No.: US 8,541,234 B2
(45) Date of Patent: Sep. 24, 2013

(54) METHODS OF GENERATING TENDON TISSUE IN VITRO FROM CONNECTIVE TISSUE PROGENITOR CELLS

(75) Inventors: Joseph Itskovitz-Eldor, Haifa (IL); Shahar Cohen, Kiryat-Motzkin (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/526,633

(22) Filed: Jun. 19, 2012

(65) Prior Publication Data

US 2012/0253463 A1     Oct. 4, 2012

Related U.S. Application Data

(62) Division of application No. 12/087,664, filed as application No. PCT/IL2007/000047 on Jan. 11, 2007, now Pat. No. 8,241,902.

(60) Provisional application No. 60/861,081, filed on Nov. 27, 2006, provisional application No. 60/861,080, filed on Nov. 27, 2006, provisional application No. 60/757,864, filed on Jan. 11, 2006.

(51) Int. Cl.
*C12N 15/02*     (2006.01)

(52) U.S. Cl.
USPC .......................................... 435/377; 435/384

(58) Field of Classification Search
None
See application file for complete search history.

(56) References Cited

U.S. PATENT DOCUMENTS

| | | |
|---|---|---|
| 7,297,539 B2 | 11/2007 | Mandalam et al. |
| 2003/0021771 A1 | 1/2003 | Xu et al. |
| 2003/0026786 A1 | 2/2003 | Pittenger et al. |
| 2003/0036194 A1 | 2/2003 | Xu et al. |
| 2003/0109038 A1 | 6/2003 | Thies |
| 2003/0219423 A1 | 11/2003 | Gazit et al. |
| 2009/0093056 A1 | 4/2009 | Itskovitz-Eldor et al. |
| 2010/0035341 A1 | 2/2010 | Itskovitz-Eldor et al. |

FOREIGN PATENT DOCUMENTS

| | | |
|---|---|---|
| EP | 1627913 | 2/2006 |
| WO | WO 2005/001076 | 1/2005 |
| WO | WO 2005/012512 | 2/2005 |
| WO | WO 2005/108559 | 11/2005 |
| WO | WO 2005/121319 | 12/2005 |
| WO | WO 2007/080590 | 7/2007 |
| WO | WO 2007/080591 | 7/2007 |

OTHER PUBLICATIONS

Calve et al. Engineering of Functional Tendon. Tissue Engineering, 2004, vol. 10, pp. 755-764.*
Ouyang et al. Knitted Poly-lactide-co-glycolide Scaffold Loaded with Bone Marrow Stromal Cells in Repair and Regeneration of Rabbit Achilles TendonTissue Engineering, 2003, vol. 9, pp. 431-439.*
International Preliminary Report on Patentability Dated Jan. 22, 2009 From the International Bureau of WIPO Re.: Application No. PCT/IL000047.
International Preliminary Report on Patentability Dated Jan. 22, 2009 From the International Bureau of WIPO Re.: Application No. PCT/IL2007/000046.
Communication Pursuant to Article 94(3) EPC Dated Aug. 2, 2011 From the European Patent Office Re. Application No. 07700739.1.
Communication Pursuant to Article 94(3) EPC Dated Oct. 11, 2011 From the European Patent Office Re.: Application No. 07700738.3.
Communication Pursuant to Article 94(3) EPC Dated Dec. 16, 2009 From the European Patent Office Re.: Application No. 07700738.3.
Communication Pursuant to Article 94(3) EPC Dated Oct. 25, 2010 From the European Patent Office Re.: Application No. 07700739.1.
Communication Pursuant to Article 94(3) EPC Dated Nov. 26, 2010 From the European Patent Office Re.: Application No. 07700738.3.
Communication Pursuant to Article 94(3) EPC Dated Oct. 29, 2009 From the European Patent Office Re.: Application No. 07700739.1.
Notice of Allowance Dated Feb. 17, 2012 From the US Patent and Trademark Office Re. U.S. Appl. No. 12/087,664.
Office Action Dated Aug. 8, 2010 From the Israel Patent Office Re. Application No. 192709 and Its Translation Into English.
Office Action Dated Aug. 8, 2010 From the Israel Patent Office Re. Application No. 192710 and Its Translation Into English.
Office Action Dated Mar. 24, 2011 From the Israel Patent Office Re. Application No. 192709 and Its Translation Into English.
Office Action Dated Mar. 24, 2011 From the Israel Patent Office Re. Application No. 192710 and Its Translation Into English.
Official Action Dated Jun. 4, 2012 From the US Patent and Trademark Office Re. U.S. Appl. No. 12/087,610.
Official Action Dated Nov. 8, 2011 From the US Patent and Trademark Office Re. U.S. Appl. No. 12/087,610.
Official Action Dated Feb. 14, 2011 From the US Patent and Trademark Office Re. U.S. Appl. No. 12/087,664.
Official Action Dated Jun. 16, 2011 From the US Patent and Trademark Office Re. U.S. Appl. No. 12/087,664.
Official Action Dated Jul. 22, 2010 From the US Patent and Trademark Office Re. U.S. Appl. No. 12/087,664.
Official Action Dated Nov. 23, 2011 From the US Patent and Trademark Office Re. U.S. Appl. No. 12/087,664.
Official Action Dated Sep. 30, 2010 From the US Patent and Trademark Office Re. U.S. Appl. No. 12/087,664.
Response Dated Jun. 7, 2010 to Search Report and Written Opinion of Dec. 10, 2009 From the Intellectual Property Office of Singapore Issued by the Austrian Patent Office Re.: Application No. 200805148-4.
Response Dated Dec. 8, 2010 to Office Action of Aug. 8, 2010 From the Israel Patent Office Re. Application No. 192709.
Response Dated Dec. 8, 2010 to Office Action of Aug. 8, 2010 From the Israel Patent Office Re. Application No. 192710.
Response Dated Jun. 13, 2010 to Communication Pursuant to Article 94(3) EPC of Dec. 16, 2009 From the European Patent Office Re.: Application No. 07700738.3.

(Continued)

*Primary Examiner* — Deborah Crouch

(57) ABSTRACT

Methods of generating and expanding proliferative, multipotent connective tissue progenitor cells from adult stem cells are provided. Also provided are methods of generating functional tendon grafts in vitro and bone, cartilage and connective tissues in vivo using the isolated cell preparation of connective tissue progenitor cells.

15 Claims, 21 Drawing Sheets
(17 of 21 Drawing Sheet(s) Filed in Color)

(56) References Cited

OTHER PUBLICATIONS

Response Dated Sep. 15, 2011 to Official Action of Jun. 16, 2011 From the US Patent and Trademark Office Re. U.S. Appl. No. 12/087,664.
Response Dated May 16, 2011 to Official Action of Feb. 14, 2011 From the US Patent and Trademark Office Re. U.S. Appl. No. 12/087,664.
Response Dated Aug. 23, 2010 to Official Action of Jul. 22, 2010 From the US Patent and Trademark Office Re. U.S. Appl. No. 12/087,664.
Response Dated Feb. 23, 2011 to Communication Pursuant to Article 94(3) EPC of Oct. 25, 2010 From the European Patent Office Re.: Application No. 07700739.1.
Response Dated Mar. 24, 2011 to Communication Pursuant to Article 94(3) EPC of Nov. 26, 2010 From the European Patent Office Re.: Application No. 07700738.3.
Response Dated Apr. 27, 2010 to Communication Pursuant to Article 94(3) EPC of Oct. 29, 2009 From the European Patent Office Re.: Application No. 07700739.1.
Response Dated Dec. 27, 2010 to Search Report and Written Opinion of Aug. 2, 2010 From the Intellectual Property Office of Singapore Re. Application No. 200805146-8.
Response Dated Dec. 29, 2010 to Official Action of Sep. 30, 2010 From the US Patent and Trademark Office Re. U.S. Appl. No. 12/087,664.
Response Dated Nov. 30, 2011 to Communication Pursuant to Article 94(3) EPC of Aug. 2, 2011 From the European Patent Office Re. Application No. 07700739.1.
Search Report and Written Opinion Dated Aug. 2, 2010 From the Intellectual Property Office of Singapore Issued on Jan. 18, 2010 by the Austrian Patent Office Re. Application No. 200805146-8.
Search Report and Written Opinion Dated Dec. 10, 2009 From the Intellectual Property Office of Singapore Issued by the Austrian Patent Office Re.: Application No. 200805148-4.
Supplementary European Search Report and the European Search Opinion Dated Jul. 10, 2009 From the European Patent Office Re.: Application No. 07700739.1.
Supplementary European Search Report and the European Search Opinion Dated Sep. 22, 2009 From the European Patent Office Re.: Application No. 07700738.3.
Written Opinion Dated Aug. 12, 2008 From the international Searching Authority Re.: Application No. PCT/IL07/00046.
Written Opinion Dated Oct. 15, 2008 From the International Searching Authority Re.: Application No. PCT/IL07/00047.
Banfi et al. "Proliferation Kinetics and Differentiation Potential of Ex Vivo Expanded Human Bone Marrow Stromal Cells: Implications for Their Use in Cell Therapy", Experimental Hematology, XP002441523, 28(6): 707-715, Jun. 2000. Abstract, p.708-709.
Barberi et al. "Derivation of Multipotent Mesenchymal Precursors From Human Embryonic Stem Cells", PLoS Medicine, XP002544487, 2(6): 0554-0560, 2005.
Campagnoli et al. "Identification of Mesenchymal Stern/Progenitor Cells in Human First-Trimester Fetal Blood, Liver, and Bone Marrow", Blood, 98(8): 2396-2402, Oct. 15, 2001. Abstract, p. 2397, r-h col., § 3, 1-h col., § 1, 3, p. 2398, r-h col., § 3, p. 2399, Fig.2, p. 2400, Fig.5.
Cao et al. "Osteogenic Differentiation Within Human Embryoid Bodies Result in a Marked Increase in Osteocalcin Secretion After 12 Days of in Vitro Culture, and Formation of Morphologically Distinct Nodule-Like Structures", Tissue and Cell, XP004965194, 37(4): 325-334, Aug. 2005. Abstract, Material and Method.
Caplan "Mesenchymal Stem Cells: Cell-Based Reconstructive Therapy in Orthopedics", Tissue Engineering, XP002534528, 11(7-8): 1198-1211, Jul. 2005.
Chan et al. "Human Fetal Mesenchymal Stem Cells as Vehicles for Gene Delivery", Stem Cells, 23: 93-102, 2005.
Coelho et al. "Human Bone Cell Cultures in Biocompatibility Testing. Part II: Effect of Ascorbic Acid, ?-Glycerophosphate and Dexamethasone on Osteoblastic Differentiation", Biomaterials, 21(11): 1095-1102, Jun. 2000.
Cohen et al. "Tissue Engineering Using Human Embryonic Stem Cell", Methods in Enzymology—Stem Cell Tools and Other Experimental Protocols, XP009118865, 420: 303-315, 2006.
D'Ippolito et al. "Marrow-Isolated Adult Multilineage Inducible (MIAMI) Cells, A Unique Population of Postnatal Young and Old Human Cells With Extensive Expasion and Differentiation Potential", Journal of Cell Science, XP002559663, 117: 2971-2981, Jun. 15, 2004.
Dominici et al. "Minimal Criteria for Defining Multipotent Mesenchymal Stromal Cells. The International Society for Cellular Therapy Position Statement", Cytotherapy, 8(4): 315-317, 2006.
Galotto et al. "Stromal Damage as Consequence of High-Dose Chemo/Radiotherapy in Bone Marrow Transplant Recipients", Experimental Hematology, 27: 1460-1466, 1999.
Haegel et al. "CD44 in Differentiated Embryonic Stem Cells: Surface Expression and Transcripts Encoding Multiple Variants", Developmental Immunology, 3(4): 239-246, 1994.
Heng et al. "Directing Stem Differentiation Into the Chondrogenic Lineage in Vitro", Stem Cells, XP002534527, 22(7): 1152-1167, 2004.
Heng et al. "Strategies for Directing the Differentiation of Stem Cells Into the Osteogenic Lineage In Vitro", Journal of Bone and Mineral Research, XP002534526, 19(9): 1379-1394, Sep. 2004.
Im et al. "Do Adipose Tissue-Derived Mesenchymal Stem Cells Have the Same Osteogenic and Chondrogenic Potential as Bone Marrow-Derived Cells?", OsteoArthritis and Cartilage, XP005094309, 13(10): 845-853, Oct. 2005. Abstract.
Jaiswal et al. "Osteogenic Differentiation of Purified, Culture-Expanded Human Mesenchymal Stem Cells In Vitro", Journal of Cellular Biochemistry, 64: 295-312, 1997.
Jiang et al. "Pluripotency of Mesenchymal Stem Cells Derived From Adult Marrow", Nature, XP002559664, 418: 41-49, Jul. 4, 2002.
Kelm et al. "Microscale Tissue Engineering Using Gravity-Enforced Cell Assembly", Trends in Biotechnology, XP004497323, 22(4): 195-202, Apr. 2004. Abstract.
Krampera et al. "Mesenchymal Stem Cells for Bone, Cartilage, Tendon and Skeletal Muscle Repair", Bone, XP025061266, 39(4): 678-683, Oct. 2006.
Kuznetsov et al. "Effect of Serum on Human Bone Marrow Stromal Cells: Ex Vivo Expansion and In Vivo Bone Formation", Transplantation, 70(12): 1780-1787, Dec. 27, 2000.
Li et al. "Mesemchymal Stem Cells Derived From the Human Placenta Suppress Allogeneic Umbilical Cord Blood Lymphocyte Proliferation", Cell Research, 15(7): 539-547, Jul. 2005.
Marley et al. "Peripheral Blood Progenitor Cell Mobilisation Alters Myeloid, But Not Erythroid, Progenitor Cell Self-Renewal Kinetics", Bone Marrow Transplantation, 27: 241-248, 2001.
Marlovits et al. "Chondrogenesis of Aged Human Articular Cartilage in a Scaffold-Free Bioreactor", Tissue Engineering, XP002534525, 9(6): 1215-1226, Dec. 2003. Abstract.
Massachusetts Human Stem Cell Bank "Human Embryonic Stem Cell (hESC) Assessment by Flow Cytometry Using Directly Conjugated Antibodies", Massachusetts Human Stem Cell Bank, SOP-CH-001, p. 92-96, Feb. 24, 2009.
Mauney et al. "Matrix-Mediated Retention of Adipogenic Differentiation Potential by Human Adult Bone Marrow-Derived Mesenchymal Stem Cells During Ex Vivo Expansion", Biomaterials, 26(31): 6167-6175, Nov. 2005.
McBeath et al. "Cell Shape, Cytoskeletal Tension, and RhoA Regulate Stem Lineage Commitment", Development Cell, 6: 483-495, Apr. 2004.
Muraglia et al. "Clonal Mesenchymal Progenitors From Human Bone Marrow Differentiate In Vitro According to a Hierarchical Model", Journal of Cell Science, 113: 1161-1166, 2000.
Olivier et al. "Differentiation of Human Embryonic Stem Cells Into Bipotent Mesenchymal Stem Cells", Stem Cells, XP009078939, 24(8): 1914-1922, Aug. 2006. Abstract.
Peter et al. "Osteoblastic Phenotype of Rat Marrow Stromal Cells Cultured in the Presence of Dexamethasone, β-Glycerolphospliate, and L-Ascorbic Acid", Journal of Cellular Biochemistry, 71: 55-62, 1998.

Pittenger et al. "Multilineage Potential of Adult Human Mesenchymal Stem Cells", Science, 284: 143-147, Apr. 2, 1999. p. 143, r-h col., § 2.
Robertson "NIH Sacrifices Commercial Rights in WiCell Deal", Nature Biotechnology, 19: 1001, Nov. 2001.
Sottile et al. "In Vitro Osteogenic Differentiation of Human ES Cells", Cloning and Stem Cells, XP009053197, 5(2): 149-155, 2003. Abstract.
Tsai et al. "Isolation of Human Multipotent Mesenchymal Stem Cells From Second-Trimester Amniotic Fluid Using a Novel Two-Stage Culture Protocol", Human Reproduction, 19(6): 1450-1456, 2004.
Walsh et al. "High Concentrations of Dexamethasone Suppress the Proliferation But Not the Differentiation or Further Maturation of Human Osteoblast Precursors In Vitro: Relevance to Glucocorticoid-Induced Osteoporosis", Rheumatology, 40(1): 74-83, 2001.
Notice of Allowance Dated Aug. 17, 2012 From the US Patent and Trademark Office Re. U.S. Appl. No. 12/087,610.
Communication Pursuant to Article 94(3) EPC Dated Sep. 11, 2012 From the European Patent Office Re.: Application No. 07700739.1.
Pachón-Peña et al. "Stromal Stem Cells From Adipose Tissue and Bone Marrow of Age-Matched Female Donors Display Distinct Immunophenotypic Profiles", Journal of Cellular Physiology, XP055031572, 226(3): 843-851, Mar. 1, 2011.
Hairfield-Stein et al. "Development of Self-Assembled, Tissue-Engineered Ligament From Bone Marrow Stromal Cells", Tissue Engineering, 13(4): 703-710, Apr. 2007. Abstract.
Hasegawa et al. "Human Periodontal Ligament Cell Sheets Can Regenerate Periodontal Ligament Tissue in an Athymic Rat Model", Tissue Engineering, 11 (3-4): 469-478, Mar.-Apr. 2005. Abstract.
Kanzaki et al. "Tissue Engineered Epithelial Cell Sheets for the Creation of a Bioartificial Trachea", Tissue Engineering, 12(5): 1275-1283, May 2006. Abstract.
Larkin et al. "Structure and Functional Evaluation of Tendon-Skeletal Muscle Constructs Engineered In Vitro", Tissue Engineering, 12(1): 3149-3159, 2006.
Ouyang et al. "Assembly of Bone Marrow Stromal Cell Sheets With Knitted Poly (L-Lactide) Scaffold for Engineering Ligament Analogs", Journal of Biomedical Materials Research, Part B: Applied Biomaterials, 75(2): 264-271, Nov. 2005. Abstract.
Patel et al. "Elastin Biosynthesis: The Missing Link in Tissue-Engineered Blood Vessels", Cardiovascular Research, 71: 40-49, 2006.
Communication Pursuant to Article 94(3) EPC Dated Nov. 26, 2012 From the European Patent Office Re.: Application No. 07700738.3.
Communication Pursuant to Article 94(3) EPC Dated Jun. 10, 2013 From the European Patent Office Re. Application No. 07700739.1.
Galotto et al. "Stromal Damage as Consequence of High-Dose Chemo/Radiotherapy in Bone Marrow Transplant Recipients", Experimental Hematology, XP055065103, 27(9): 1460-1466, Sep. 1, 1999.

* cited by examiner

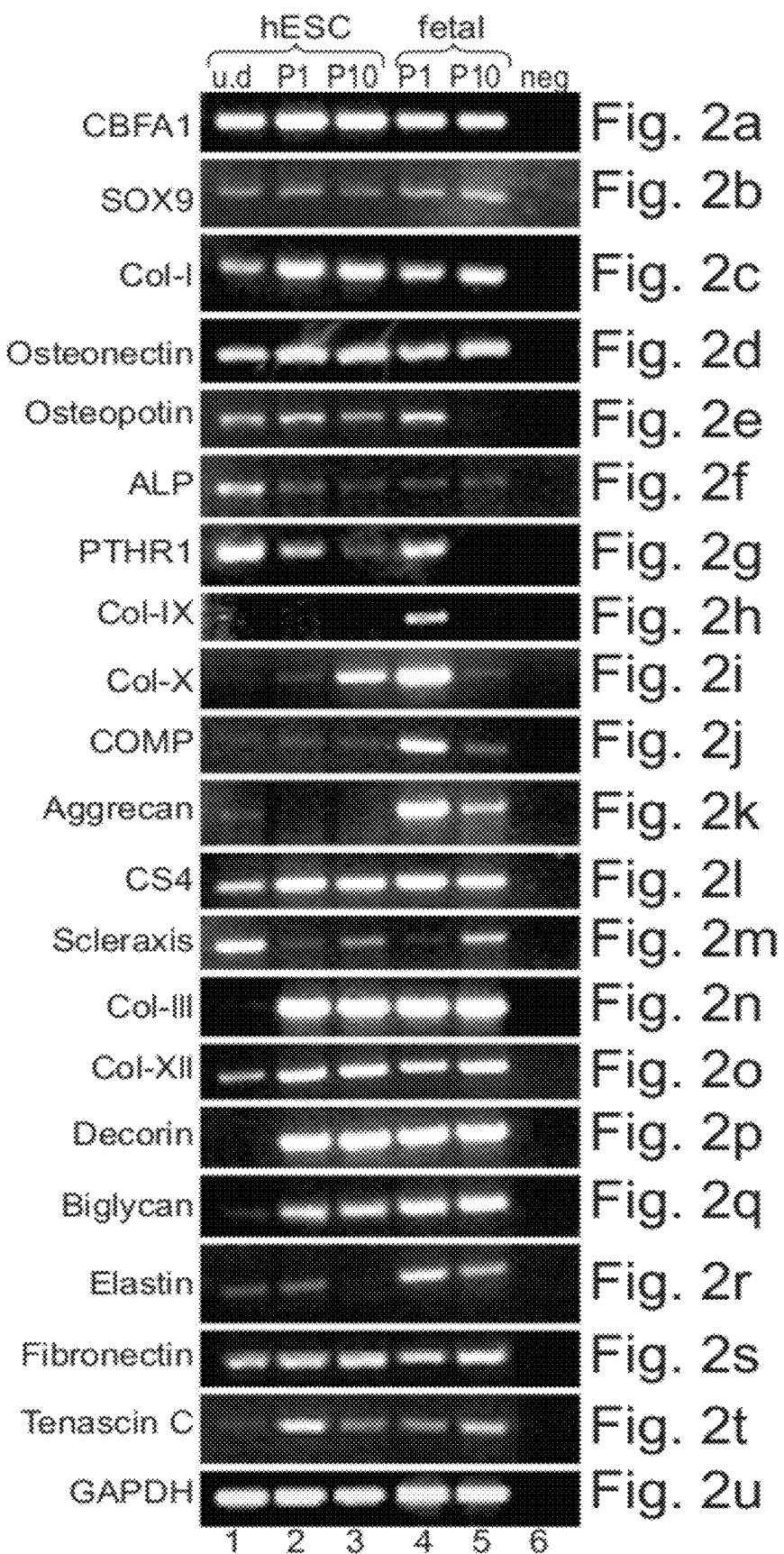

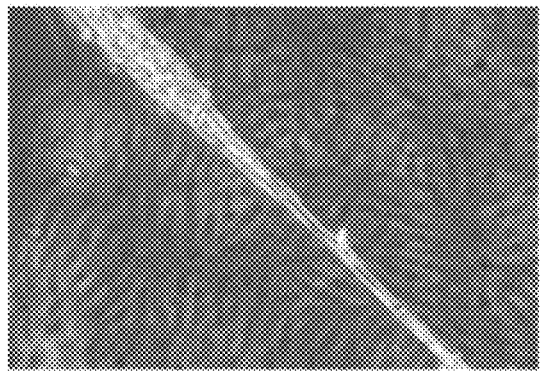 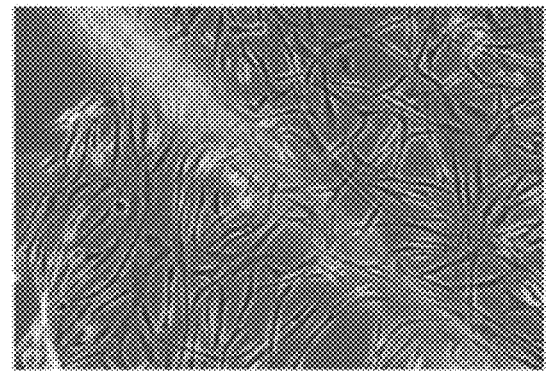
Fig. 5a　　　　　　　　Fig. 5b
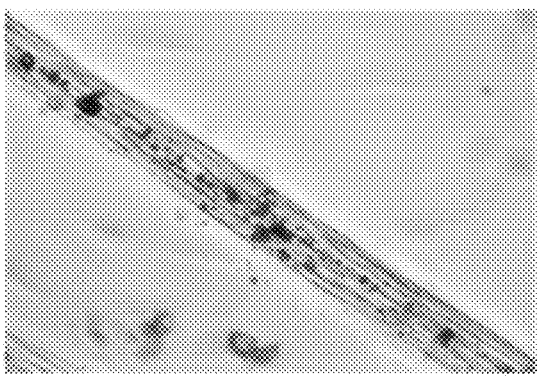 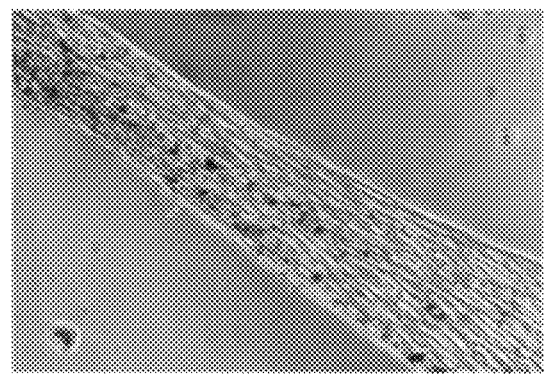
Fig. 5c　　　　　　　　Fig. 5d
 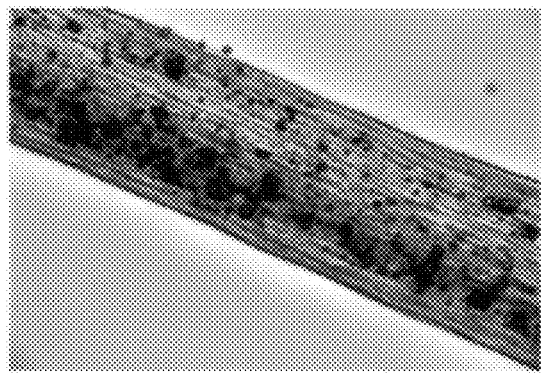
Fig. 5e　　　　　　　　Fig. 5f

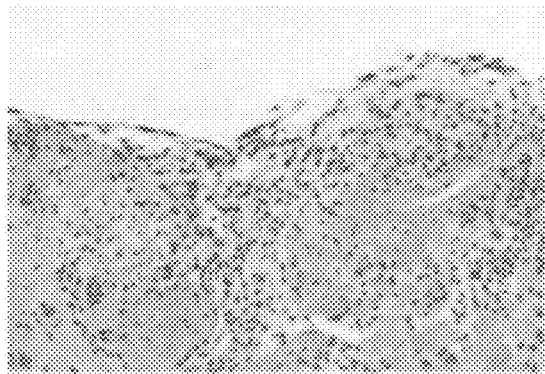 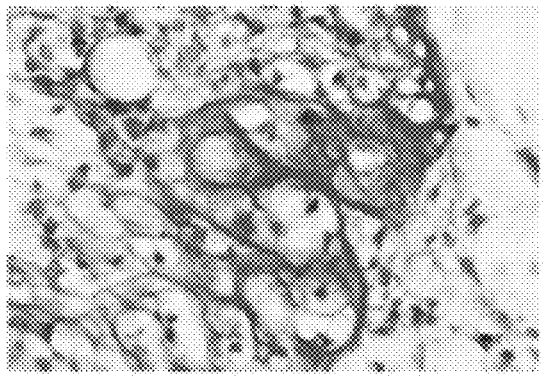
Fig. 9a    Fig. 9b
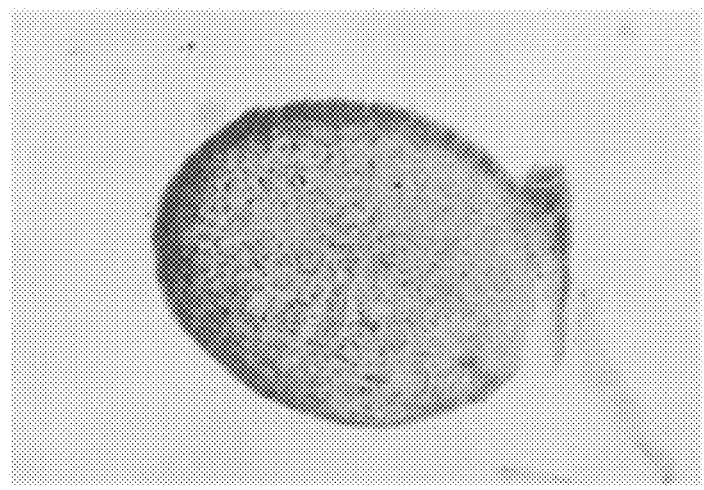
Fig. 10

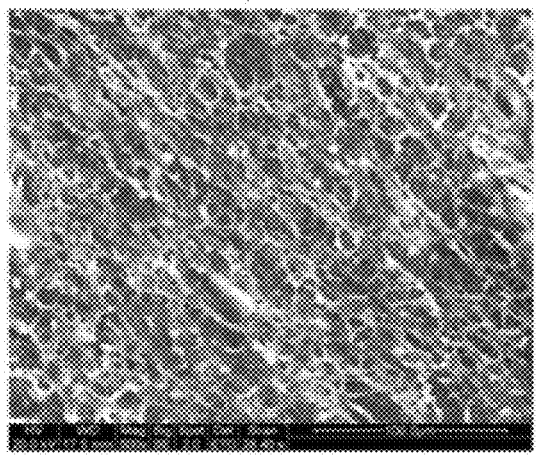
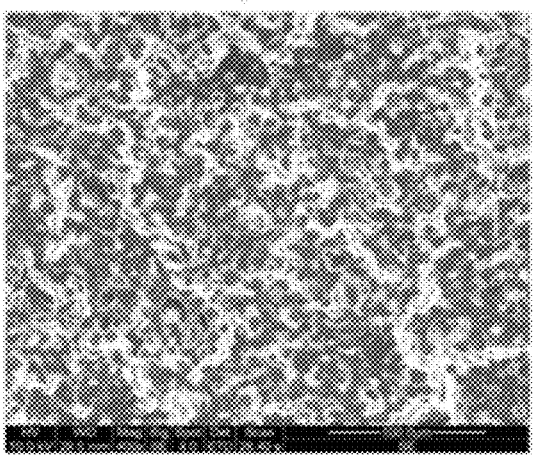
Fig. 16a
Fig. 16b
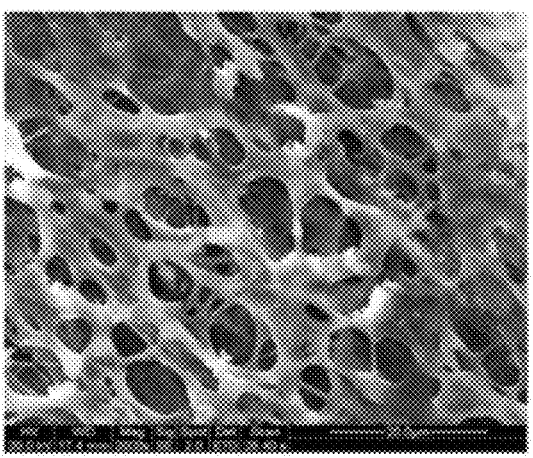
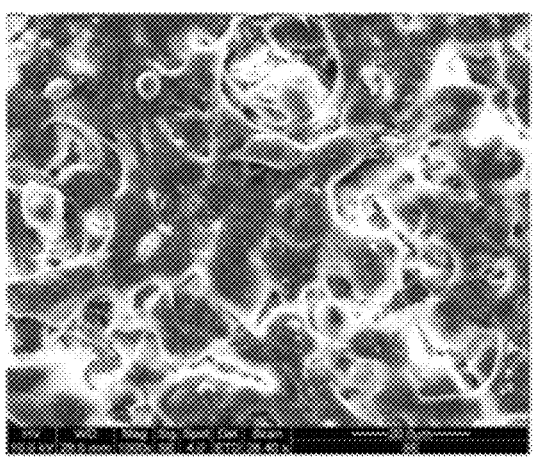
Fig. 16c
Fig. 16d
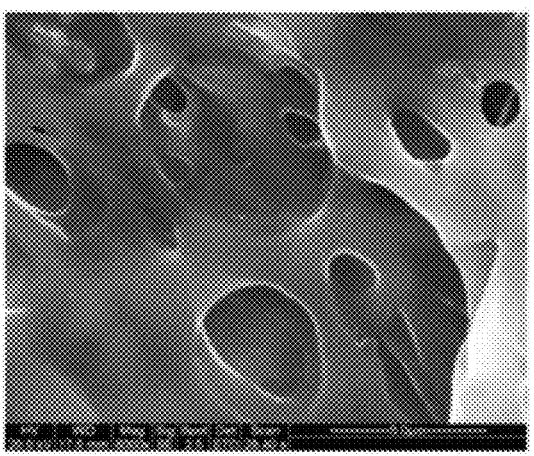
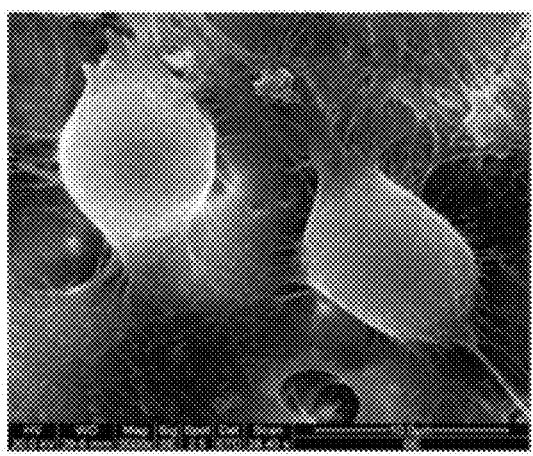
Fig. 16e
Fig. 16f

METHODS OF GENERATING TENDON TISSUE IN VITRO FROM CONNECTIVE TISSUE PROGENITOR CELLS

RELATED APPLICATIONS

This application is a divisional of U.S. patent application Ser. No. 12/087,664 filed on Dec. 2, 2008, which is a National Phase of PCT Patent Application No. PCT/IL2007/000047 having International filing date of Jan. 11, 2007, which claims the benefit of priority of U.S. Provisional Patent Application Nos. 60/861,081 filed on Nov. 27, 2006, 60/861,080 filed on Nov. 27, 2006 and 60/757,864 filed on Jan. 11, 2006. The contents of the above applications are all incorporated herein by reference.

FIELD AND BACKGROUND OF THE INVENTION

The present invention relates to adult tissue-derived connective tissue progenitor cells (CTPs) which exhibit high proliferation rate and multipotent differentiation potential which is maintained for at least 20 passages, and more particularly, to methods of generating and using such cells for cell based therapy and tissue engineering applications.

Cell-based tissue engineering is an evolving interdisciplinary area that offers new opportunities for clinical applications, creating a tool for repairing and replacing damaged or lost tissues with biological substitutes. The shortage of organ transplants and the exceeding number of patients on waiting lists greatly encourage the development of this field. The fundamentals of tissue engineering combine cells, bioactive matrices and chemically and biophysically defined in-vitro culture conditions. For tissue engineering, cells must be easily isolated, sufficient in numbers, with a great proliferation capacity and a well-defined differentiation potential. A number of cell sources have been suggested including primary cells and stem cells which are either host- or donor-derived. A wide array of matrices, either biologically or synthetically designed, are to provide the mechanical cues and three-dimensional environment, supporting cell attachment, migration, proliferation, differentiation and organization into complex tissues. Controlling stem cell proliferation and differentiation into any desired cell type requires the identification of chemicals (e.g., hormones and growth factors) and/or growth conditions (e.g., static or dynamic culturing conditions), which regulate the differentiation into the desired cell or tissue.

Connective tissue repair and regeneration are subjected to intensive research within clinical medicine. Damaged or disordered connective tissues, such as bone, cartilage and tendons need to be reconstructed or replaced due to traumatic injuries, degenerative diseases, tumor resections and congenital malformations. Current strategies in reconstructive orthopedic surgery include the use of autografts, allografts and artificial substitutes, all subjected to various limitations. While the use of cell grafts is limited by availability and morbidity, synthetic grafts are osteoconductively inferior to their biological counterparts, and could fail.

Thus, for cell based therapy and tissue engineering applications, methods of isolating and expanding stem or progenitor cells which can give rise to an unlimited amount of connective tissue cell lineages capable of forming connective tissue in vitro are highly desired.

Various studies attempted to identify culturing conditions which can be used to generate connective tissue progenitor cells which exhibit unlimited expansion in culture and differentiation potential to cells of the connective tissue lineages.

For example, bone marrow-derived MSCs can be cultured in a culture medium (e.g., DMEM) supplemented with serum. However, although cells cultured under such conditions and isolated from the first and second passage in culture were shown capable of differentiating into the adipocytic, chondrocytic, or osteocytic lineages (see e.g., Pittenger, M. F et al, 1999), the use of such cells in tissue engineering applications such as for the in vitro construction of a mature tissue was never demonstrated.

In another study Sottile, et al., 2002, cultured human trabecular bone-derived cells in a culture medium containing serum and fibroblast growth factor (FGF-2). However, the resulting cells reached confluency only after 10-20 days, demonstrating their relatively slow proliferation rate. Although cells isolated from the first passage could be induced to differentiate into osteoblasts, chondrocytes and adipocytes, their low proliferation rate limits their use in cell based therapy and tissue engineering applications.

In another study Zuk, P. A., et al., 2001, cultured processed lipoaspirate (PLA) cells which were obtained from fat tissues in a culture medium (DMEM) supplemented with serum. However, although the cells could be passaged 13 times, their proliferation rate was extremely slow as evidenced by the low passaging frequency (i.e., every 12-13 days). Thus, although PLA cells from the first passage were capable of differentiating into the adipogenic, chondrogenic, myogenic, and osteogenic lineages, their low proliferation rate limits their use for cell based and tissue engineering applications.

U.S. Pat. Appl. No. 20050260748 discloses a method of isolating adult stem cells from an adipose tissue and culturing them in a medium containing N-acetyl-L-cysteine, an antioxidant (e.g., vitamin C) and nicotinamide. For induction into osteogenic differentiation, the cells were cultured in a medium containing dexamethasone, L-ascorbate-2-phosphate and beta-glycerphosphate.

In yet another study, Mastrogiacomo, M., et al., 2005, cultured human skeletal muscle cells in a culture medium containing fibroblast growth factor (FGF-2) and dexamethason and following two passages in such a medium the cells were further induced to differentiate in vitro into the chondrogenic, osteogenic and adipogenic cell lineages. However, the potential of using muscle-derived stem cells cultured under such conditions for generating engineered tissues in vitro was never shown.

Thus, the currently available culturing methods of stem cells do not teach the in vitro construction an engineered tissue (e.g., a mature tissue) in the absence of a scaffold, carrier or a cell support. For example, none of the above-described methods enables the formation of a mature tendon tissue.

There is thus a widely recognized need for, and it would be highly advantageous to have, methods of generating adult stem cells-derived multipotent cells which are suitable for tissue engineering devoid of the above limitations.

SUMMARY OF THE INVENTION

According to one aspect of the present invention there is provided a method of generating connective tissue progenitor cells, comprising culturing adult stem cells in a culture medium which comprises dexamethasone and ascorbic acid so as to allow differentiation of the adult stem cells into the connective tissue progenitor cells, wherein the connective tissue progenitor cells are capable of differentiating into at least two cell lineages of a connective tissue; thereby generating the connective tissue progenitor cells.

According to further features in preferred embodiments of the invention described below, the method further comprising passaging the connective tissue progenitor cells in a presence of the culture medium which comprises dexamethasone and ascorbic acid, wherein a first passage of the passaging is effected no more than 10 days following initial culturing of the adult stem cells in the culture medium.

According to still further features in the described preferred embodiments the at least two cell lineages of the connective tissue are selected from the group consisting of an osteogenic lineage, a chondrogenic lineage, an adipocytic lineage and a tendon and ligament lineage.

According to still further features in the described preferred embodiments the adult stem cells are obtained from a fetal tissue.

According to still further features in the described preferred embodiments the adult stem cells are obtained from a postnatal tissue.

According to still further features in the described preferred embodiments the fetal tissue is obtained from a placenta, amniocytes, amniotic membrane, cord blood and/or chorionic villi sample (CVS).

According to still further features in the described preferred embodiments the postnatal tissue is obtained from umbilical cord, cord blood, foreskin, bone marrow, blood, fat tissue, connective tissue and/or fibroblasts.

According to still further features in the described preferred embodiments the method further comprising expanding the connective tissue progenitor cells in the culture medium which comprises dexamethasone and ascorbic acid so as to obtain at least $3.5 \times 10^9$ connective tissue progenitor cells from a single cell of the adult stem cells following about 20 passages.

According to still further features in the described preferred embodiments culturing is effected under feeder-free culturing conditions.

According to still further features in the described preferred embodiments the culture medium further comprises inorganic phosphate.

According to still further features in the described preferred embodiments the culture medium further comprises serum or serum replacement.

According to still further features in the described preferred embodiments the adult tissue stem cells are of a human origin.

According to still further features in the described preferred embodiments passaging is effected every 2-5 days.

According to still further features in the described preferred embodiments passaging is effected for at least 20 times.

According to still further features in the described preferred embodiments culturing is effected under xeno-free conditions.

According to still further features in the described preferred embodiments passaging is effected under xeno-free conditions.

According to still further features in the described preferred embodiments passaging is effected under feeder-free culturing conditions.

According to another aspect of the present invention there is provided an isolated cell preparation of connective tissue progenitor cells resultant of the method.

According to still further features in the described preferred embodiments the connective tissue progenitor cells are capable of being maintained in a proliferative, non-terminally differentiated state for at least 20 passages in culture.

According to still further features in the described preferred embodiments the connective tissue progenitor cells express CD105, CD166, CD44, CD29 and HLA-ABC.

According to still further features in the described preferred embodiments the connective tissue progenitor cells not expressing CD45 and HLA-DR.

According to still further features in the described preferred embodiments the isolated cell preparation is devoid of feeder cells.

According to still further features in the described preferred embodiments the isolated cell preparation is xeno-free.

According to still further features in the described preferred embodiments the connective tissue progenitor cells are capable of differentiating into cells of a chondrogenic lineage, an osteogenic lineage, an adipocytic lineage, a tendon and ligament lineage.

According to still further features in the described preferred embodiments cells isolated following the at least 20 passages in culture are capable of differentiating into cells of a chondrogenic lineage, an osteogenic lineage, an adipocytic lineage, a tendon and ligament lineage.

According to still further features in the described preferred embodiments the connective tissue progenitor cells are capable of forming mineralized matrix.

According to still further features in the described preferred embodiments the connective tissue progenitor cells are capable of forming a bone tissue.

According to still further features in the described preferred embodiments the connective tissue progenitor cells are capable of forming an extracellular matrix (ECM).

According to still further features in the described preferred embodiments the connective tissue progenitor cells are capable of forming a tendon tissue.

According to still further features in the described preferred embodiments the connective tissue progenitor cells are capable of forming a ligament tissue.

According to still further features in the described preferred embodiments the connective tissue progenitor cells are capable of forming a cartilage tissue.

According to yet another aspect of the present invention there is provided a method of generating a tendon tissue, the method comprising culturing the connective tissue progenitor cells of the isolated cell preparation in a culture medium which comprises ascorbic acid and/or dexamethason under culture conditions devoid of a carrier, thereby generating the tendon tissue.

According to still another aspect of the present invention there is provided a method of forming an extracellular matrix (ECM), the method comprising culturing the connective tissue progenitor cells of the isolated cell preparation of cells in a culture medium which comprises ascorbic acid, thereby forming the ECM.

According to still further features in the described preferred embodiments the culture medium further comprises dexamethason.

The present invention successfully addresses the shortcomings of the presently known configurations by providing methods of generating and using connective tissue progenitor cells from adult stem cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
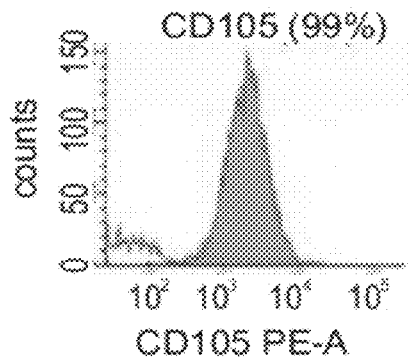
Figure 1B:
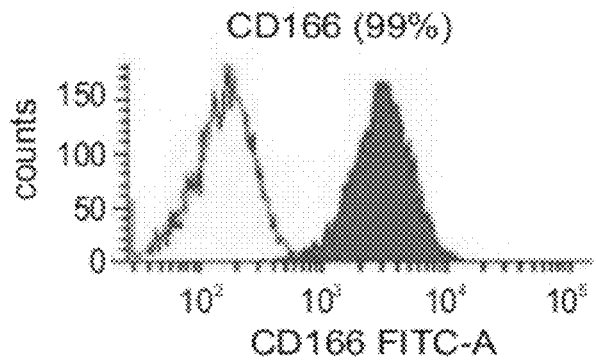
Figure 1C:
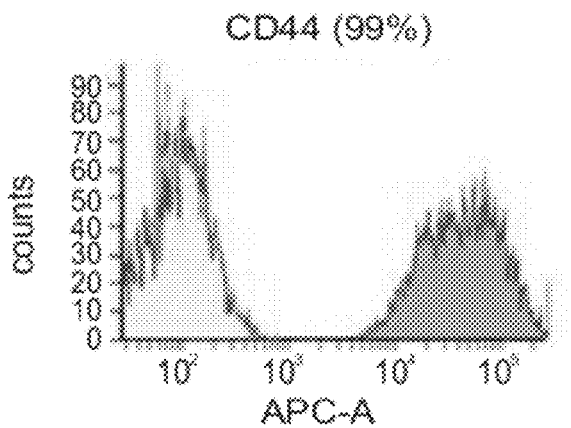
Figure 1D:
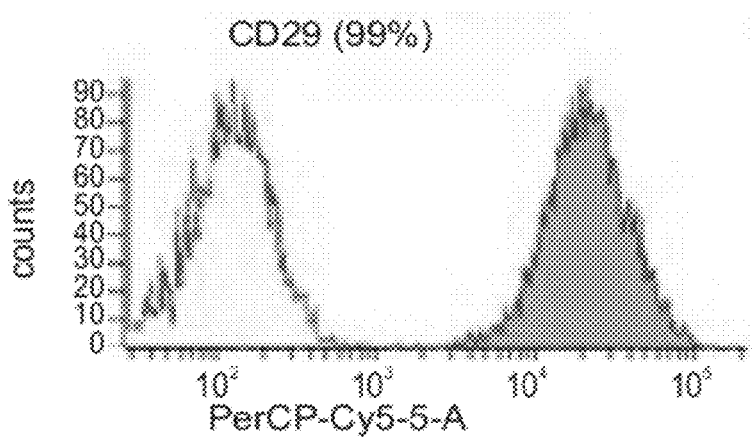
Figure 1E:
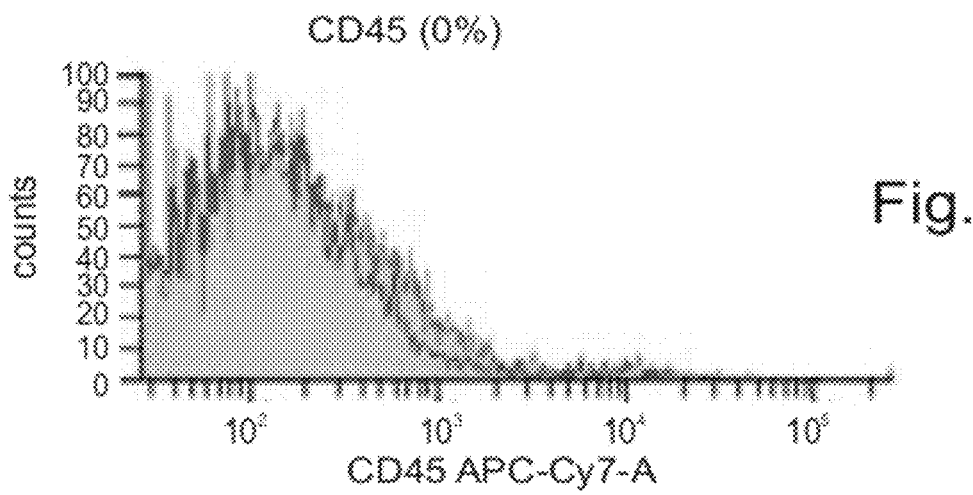
Figure 1F:
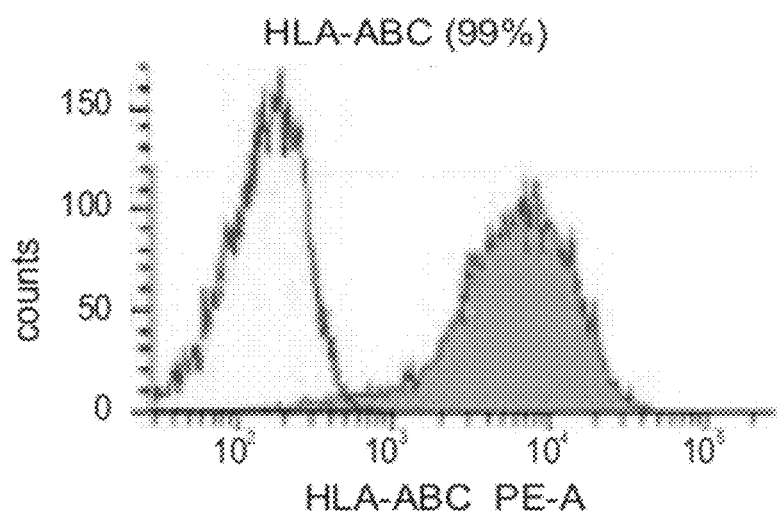
Figure 1G:
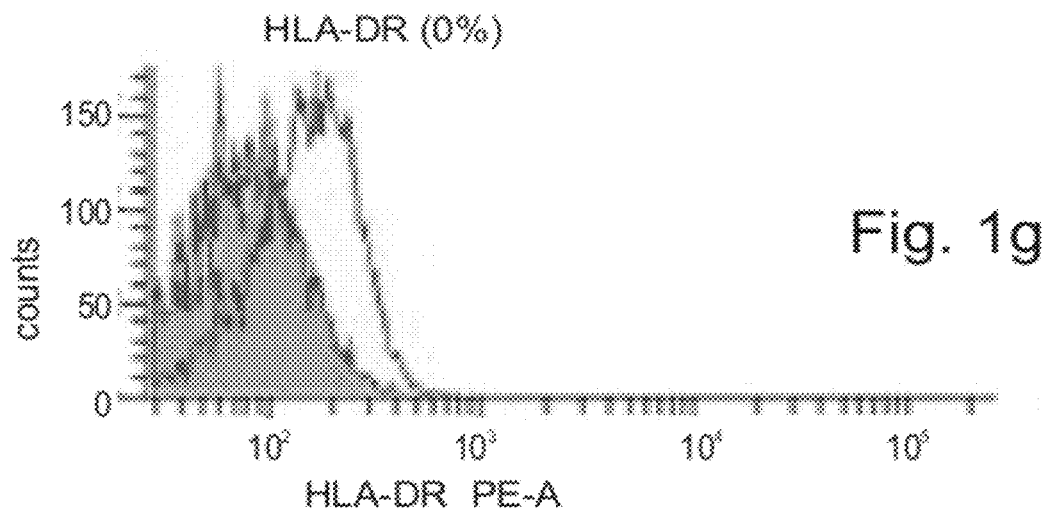

FIGS. 1a-g are FACS analyses of adult stem cells—derived CTPs (generated from a fetal tissue) showing high level of population purity with surface markers characteristic of MSCs. Adult stem cells derived CTPs were cultured in CTP medium for 16 passages and were subjected to FACS analysis using antibodies specific to CD105 (eBioscience, San Diego, Calif., Cat. No. 12-1057-73) (FIG. 1a), CD166 (Serotec, Raleigh, N.C., USA, Cat. No. MCA1926F) (FIG. 1b), CD44 (eBioscience, Cat. No. 10-0441-81) (FIG. 1c), CD29 (Serotec, Cat. No. MCA1926F) (FIG. 1d), CD45 (Pharmingen, Cat. No. 345809) (FIG. 1e), HLA-ABC (eBioscience, Cat. No. 12-9983-71) (FIG. 1f), HLA-DR (eBioscience, Cat. No. 12-9956-71) (FIG. 1g). Note the positive expression of typical MSC surface markers, including CD105 (FIG. 1a), CD166 (FIG. 1b), CD44 (FIG. 1g) and CD29 (FIG. 1d), and the negative expression (absence) of CD45 (FIG. 1e), a hematopoietic marker. Level of cell purity was confirmed to be high. Additionally, all cells were positive for HLA-ABC (FIG. 1f) and negative for HLA-DR (FIG. 1h, the major histocompatibility complex antigens).

FIGS. 2a-u are RT-PCR analyses depicting the expression of markers characteristic of bone, cartilage, tendons and ligaments at passage 1 (p1) and passage 10 (p10) of both adult stem cells-derived CTPs (generated from human fetal bone tissue) (lanes 4 and 5, respectively) and hESC-derived CTPs (lanes 2 and 3, respectively), compared to undifferentiated hESCs (u.d., lane 1) and negative (neg., lane 6) control. Adult stem cells derived CTPs were cultured in CTP medium for 1 or 10 passages, following which RNA was prepared and RT-PCR reactions were performed using the PCR primers listed in Table 1 of the Examples section which follows. The tested markers were: CBFA1 (FIG. 2a), SOX9 (FIG. 2b), Col-I (Collagen type I, FIG. 2c), Osteonectin (FIG. 2d), Osteopontin (FIG. 2e), ALP (alkaline phosphatase, FIG. 2f), PTHR1 (FIG. 2g), Col-IX (Collagen type I, FIG. 2h), Col-X (Collagen type X; FIG. 2i), COMP (FIG. 2j), Aggrecan (FIG. 2k), CS4 (FIG. 2l), Scleraxis (FIG. 2m), Col-III (Collagen type III, FIG. 2n), Col-XII (Collagen type XII, FIG. 2o), Decorin (FIG. 2p), Biglycan (FIG. 2q), Elastin (FIG. 2r), Fibronectin (FIG. 2s), Tenascin C (FIG. 2t) and GAPDH (FIG. 2u). Note that both human fetal-derived CTPs and hESC-derived CTPs express high levels of core binding factor alpha 1 (CBFA1; FIG. 2a) and SOX9 (FIG. 2b), both are early transcription factors known to play a major role in osteoblast and chondrocyte differentiation. Also note that type I collagen (Col-I, FIG. 2c), the most abundant extracellular protein which is synthesized by osteoblasts, osteonectin (FIG. 2d) and osteopontin (FIG. 2e, mainly at passage 1), two major non-collagenous bone matrix proteins, parathyroid hormone receptor 1 (PTHR1; FIG. 2g, mainly at passage 1), which regulates mineral homeostasis and bone formation, and bone-specific alkaline phosphatase (ALP; FIG. 2f), which binds phosphor to calcium and forms bone hydroxyapetite, are all detected at low and high passages, indicating osteogenic potential. Adult stem cells derived CTPs were also positive for cartilage matrix markers: chondroitin sulfate proteoglycan 4 (CS4; FIG. 2l), a cartilage matrix proteoglycan, type X collagen (FIG. 2i, mainly at passage 1), which is a non-fibril-forming collagen restricted to the hypertrophic, calcifying zone of growth plate cartilage, and cartilage oligomeric matrix protein (COMP; FIG. 2j, mainly fetal derived CTPs at passage 1), a key non-collagenous cartilage matrix protein. In addition, note the expression of tendon and ligament specific markers, such as scleraxis (FIG. 2m, mainly at passage 10), a transcription factor expressed both in their mature and early progenitor populations, and other ECM-related proteins, including type III (Col-III; FIG. 2n) and type XII (Col-XII; FIG. 2o) collagens, decorin (FIG. 2p), biglycan (FIG. 2q), elastin (FIG. 2r), fibronectin (FIG. 2s), and tenascin-C (FIG. 2t), were detected.

Figure 3A:
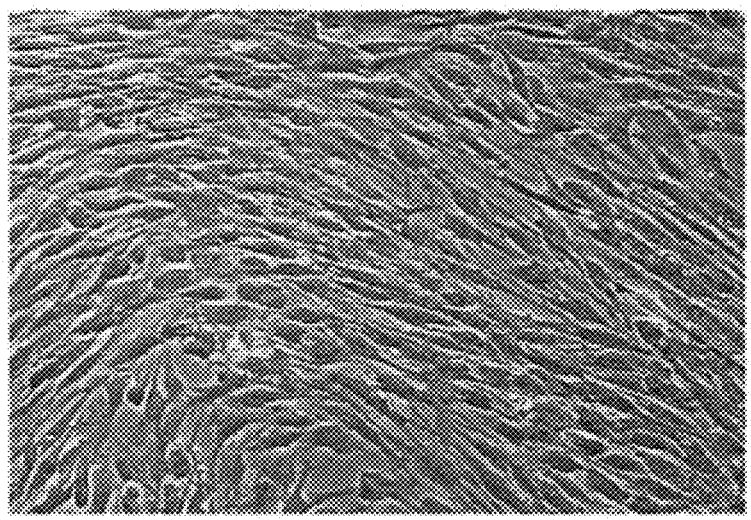
Figure 3B:
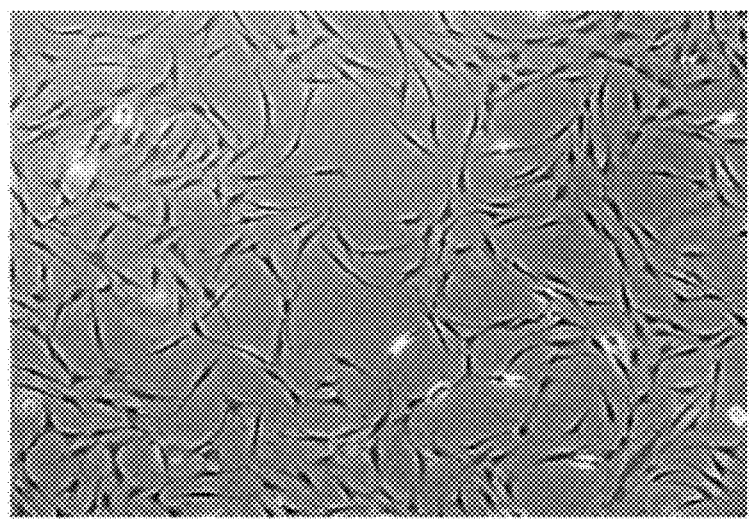
Figure 3C:
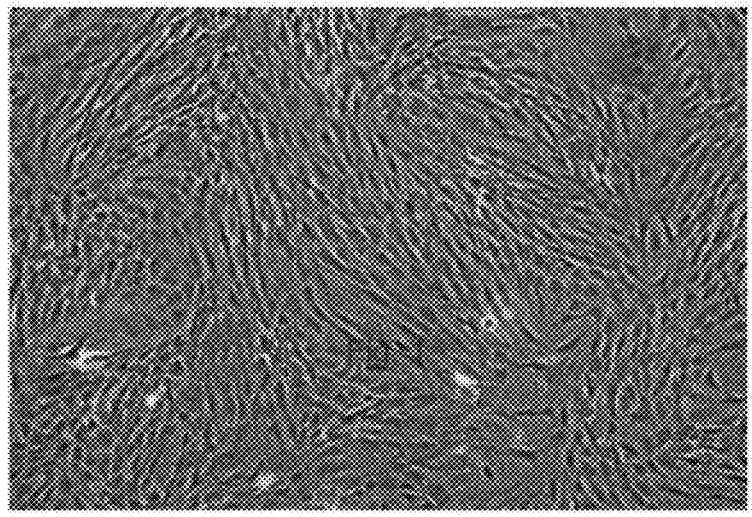
Figure 4A:
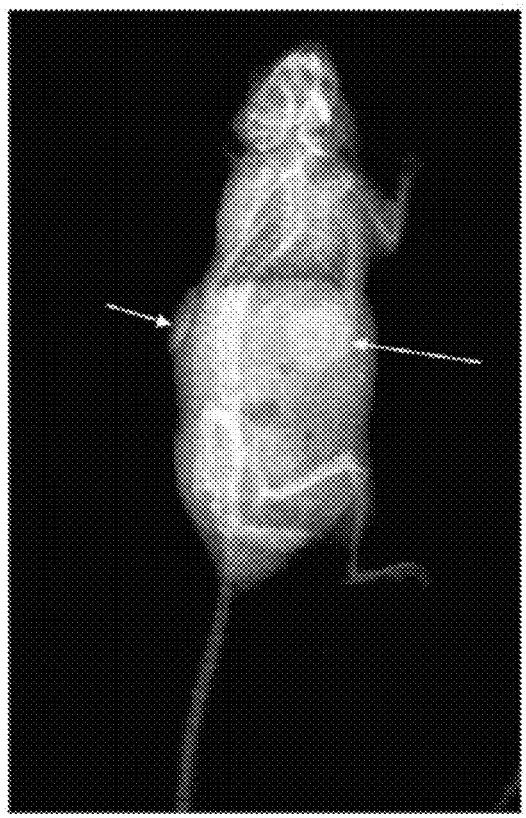
Figure 4B:
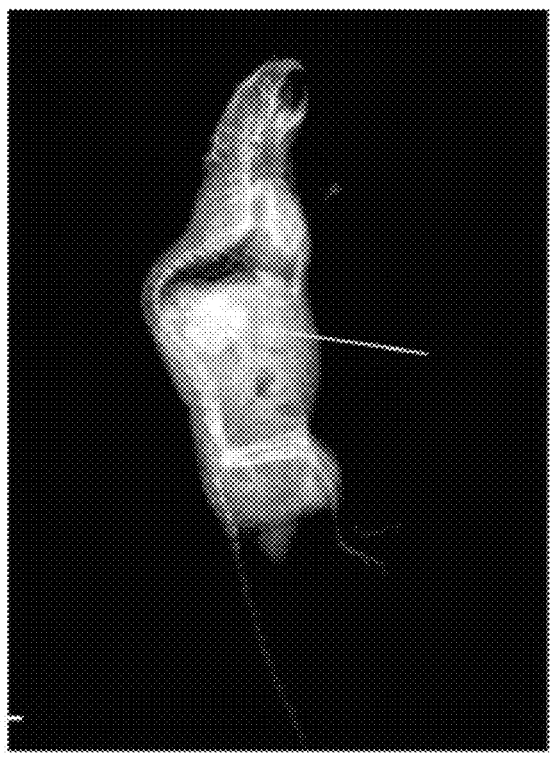
Figure 4C:
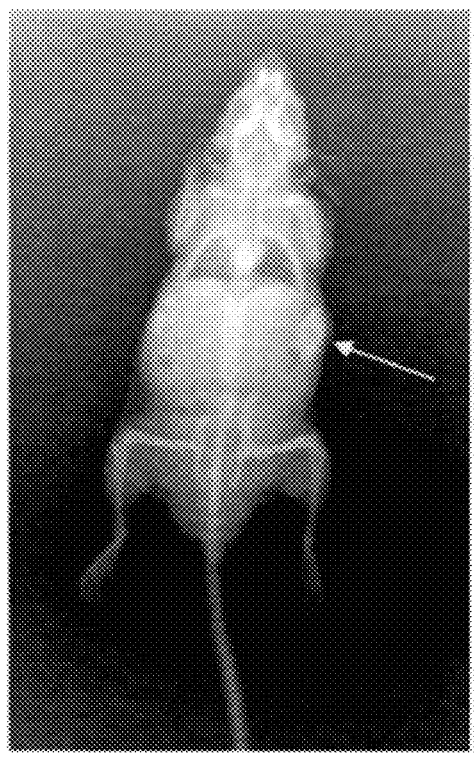

FIGS. 3a-c depict morphology of CTPs derived from connective tissue of a fetus (FIG. 3a) and from adult fat tissue (FIGS. 3b-c); FIG. 3a—CTPs from passage 1; FIG. 3b—CTPs from passage 1; FIG. 3c—CTPs from passage 5;

FIGS. 4a-c are X-ray images of mice subcutaneously transplanted (ectopic model) with the fat-derived CTPs of the present invention. FIG. 4a—3 weeks post surgery; FIGS. 4b and c—5 months post surgery; Note the presence of radio-opaque tissue (arrows) demonstrating the formation of bone tissue in vivo following 3 weeks or 5 months of transplantation.

FIGS. 5a-f are photomicrographs depicting spontaneous tendon formation by fat tissue-derived CTPs, passage 1. High-density, confluent CTP cultures promote the formation of a few cell wide string-like structure (FIG. 5a), arising and growing over the surface of the culture plate (FIG. 5b, focused on the bottom surface of the plate). At later developmental stages, the structure progressively become wider, longer and well defined, with tendon-like morphology, and elongated fibroblast-like cells growing in parallel (FIGS. 5c-f).

Figure 5G:
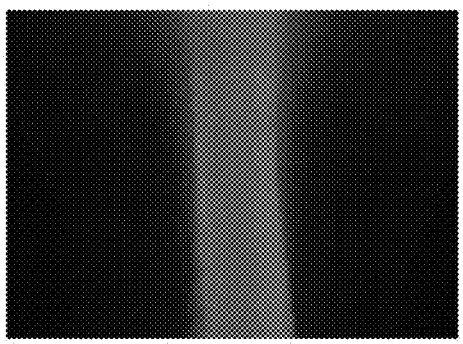
Figure 5H:
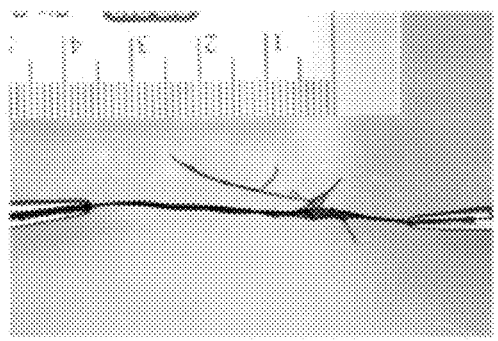
Figure 5I:
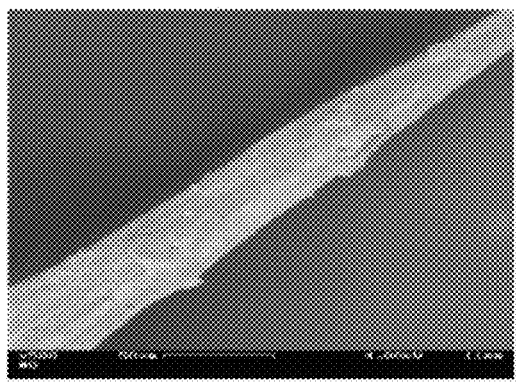
Figure 5J:
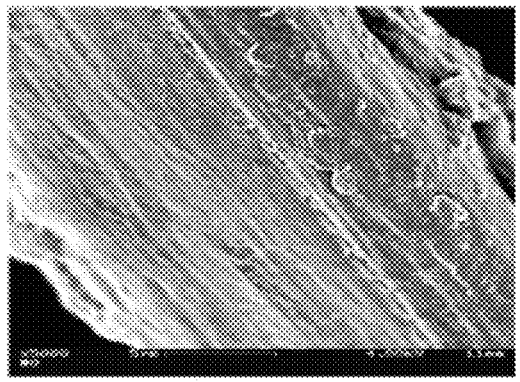
Figure 5K:
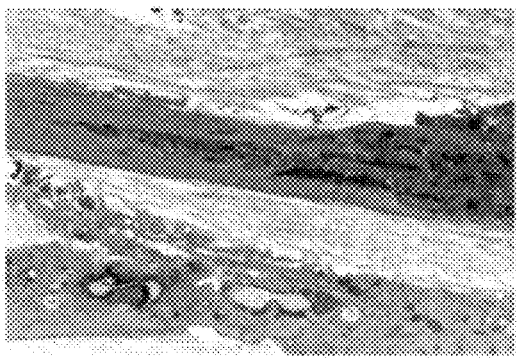
Figure 5L:
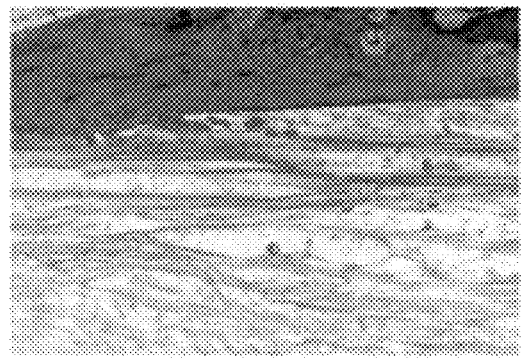
Figure 5M:
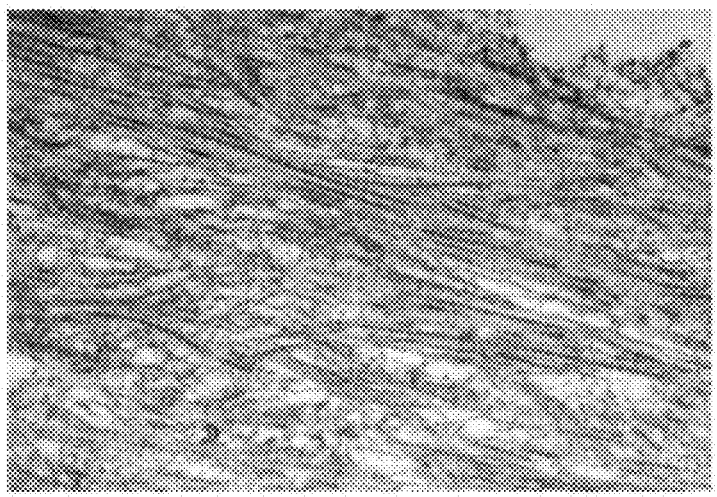

FIGS. 5g-m are photomicrographs depicting spontaneous tendon formation by fetal-derived CTPs, passage 10-14. FIG. 5g—Immunofluorescence analysis of the spontaneously formed tendon tissue using Type-I collagen antibody (Chemicon, Cat. No. MAB3991); FIG. 5h—A macroscopic view of a spontaneously formed tendon tissue; FIGS. 5i-j—SEM analyses of the spontaneously formed tendon tissue [magnifications are ×500 (FIG. 5i) and ×5000 (FIG. 5j)]; FIG. 5k, l, m—TEM analysis of the spontaneously formed tendon tissue.

Figure 6A:
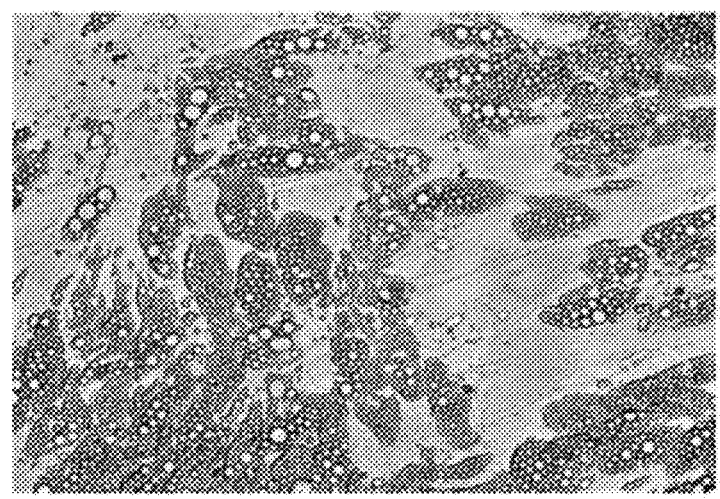
Figure 6B:
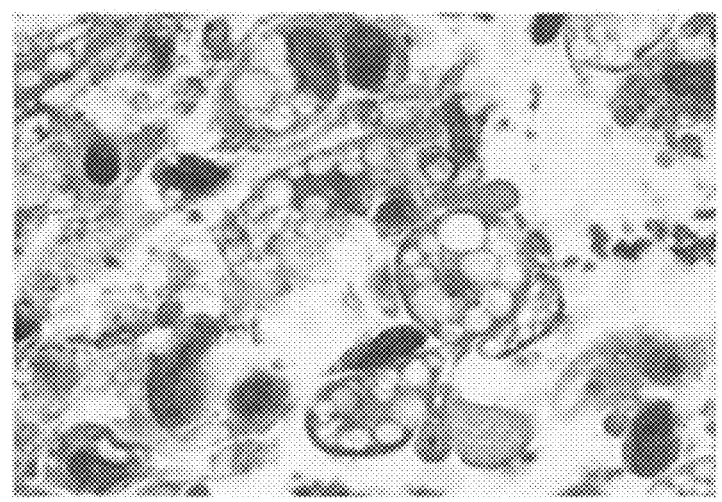

FIGS. 6a-b are photomicrographs depicting differentiation of fat tissue-derived CTPs (FIG. 6a) or fetal-derived CTPs (FIG. 6b) into adipocytes. FIG. 6a—light microscopy of fat-derived CTPs which differentiates into adipocytes. FIG. 6b—Histological staining (H&E staining) of fetal derived CTPs which differentiated into adipocytes.

Figure 7A:
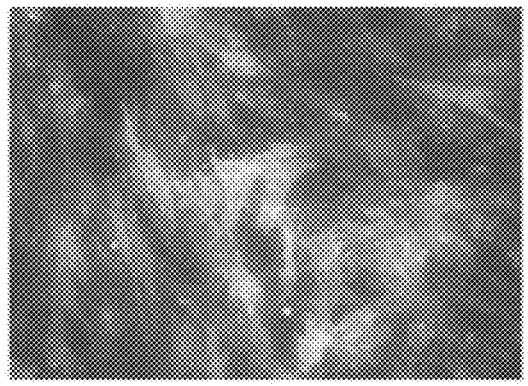
Figure 7B:
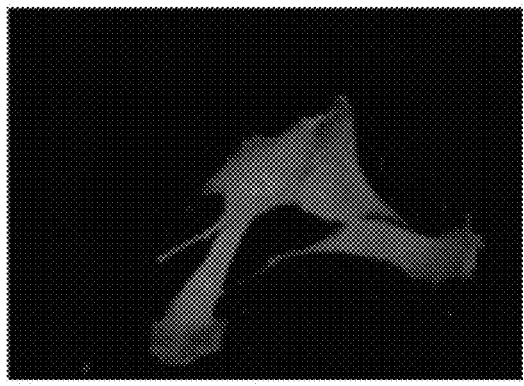

FIGS. 7a-b are photomicrographs of immunofluorescence analysis depicting that the adult stem cells derived CTPs of the present invention (from fetal tissue) express alkaline phosphatase (ALP; using the anti ALP antibody, R&D, Systems Inc, Minneapolis, Minn., USA, Cat. No. MAB1448) (FIG. 7a) and osteocalcin (using the anti osteocalcin antibody, R&D, Cat. No. MAB1419) (FIG. 7b). Nuclei were counterstained with DAPI (blue). Scale bars, 100 µm.

Figure 8A:
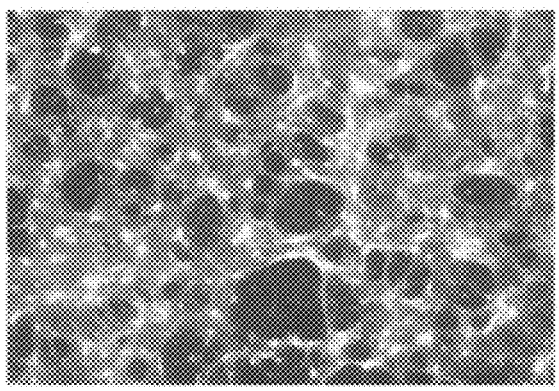
Figure 8B:
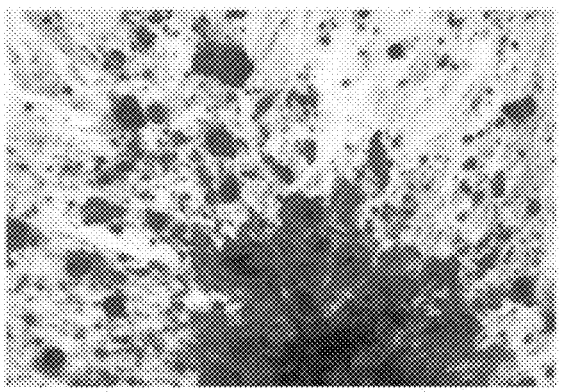
Figure 8C:
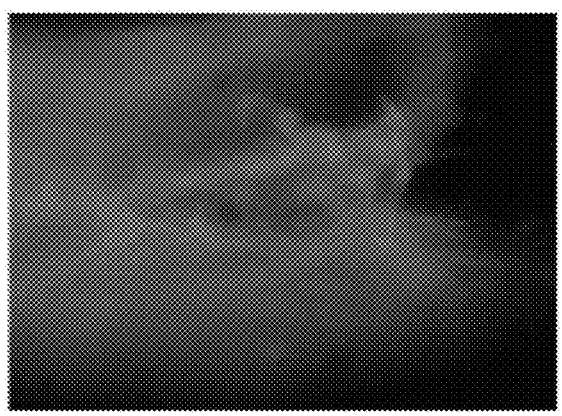
Figure 8D:
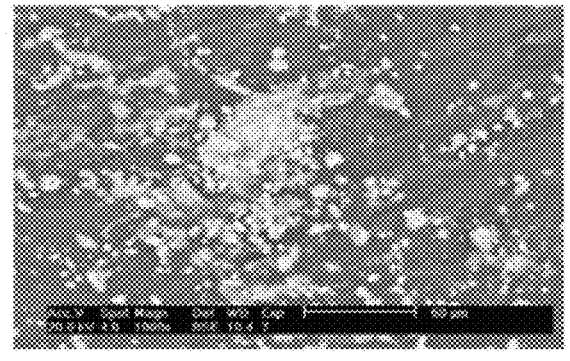

FIGS. 8a-d depict the formation of bone matrix from the adult stem cells-derived CTPs. FIG. 8a—microscopic view of CTP culture (generated from fetal tissue) demonstrating enhanced mineralization after 11 passages. FIG. 8b—Alizarin Red staining of CTP culture (generated from fetal tissue) confirming the presence of mineralization. FIG. 8c—Immunostaining analysis with type I collagen (Chemicon, Cat. No. MAB3991) demonstrating the presence of self-produced matrix in CTP cultures generated from fetal; FIG. 8d—SEM analysis of fetal derived CTPs demonstrating mineralization.

FIGS. 9a-b depict the in-vitro chondrogenic differentiation of the CTPs. Adult stem cells derived CTPs (taken from any passage of 1-25 passages) were cultured in CTP medium for 10-14 days without culture splitting and were subjected to histological and immunostaining analyses. FIG. 9a—Histological examination of intact CTP cultures (generated from a fetal tissue) which were grown in suspension. The H&E staining showing round chondrocyte-like cells embedded in lacunae, at the periphery of the sample. Scale bar—100 µm; FIG. 9b—Picro-sirius red staining detected collagenous matrix surrounding the cells. Scale bar—20 µm.

FIG. 10 is a photomicrograph of a one month old pellet section stained with Toluidine blue. Directed differentiation was induced through pellet cultures (passage 9) in the presence of low serum TGF-β3 supplemented medium. Note the presence of matrix proteoglycans (blue) in the pellet culture. Earlier pellet cultures were not positively stained (data not shown). Scale bar, 100 µm.

Figure 11A:
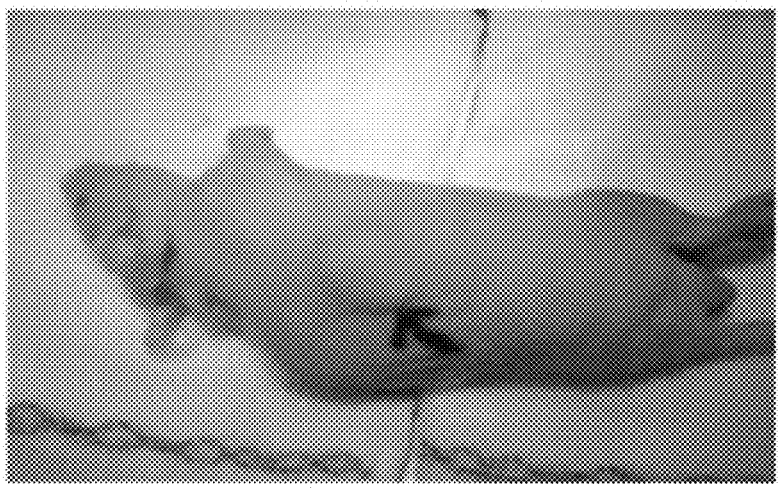
Figure 11B:
Figure 11C:
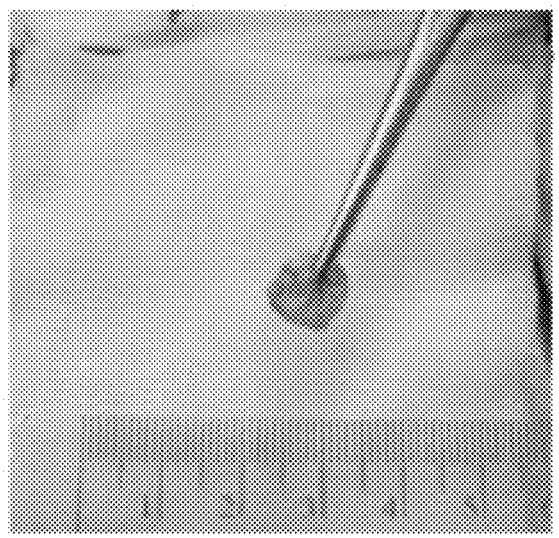

FIGS. 11a-c depict ectopic new bone formation following transplantation of the fat-derived CTPs of the present invention. FIG. 11a—a macroscopic view of a mouse bearing ectopic subcutaneous transplants of fat derived CTPs obtained from any passage of 4-20 passages. Note the visible ectopic transplants (marked with an arrow, FIG. 11a) shown 12 weeks following transplantation. FIG. 11b is a macroscopic view of a 12-week old ectopic transplant (as described in FIG. 4) following removal of skin. Note the round shape (characteristics of a non-cancerous mass), well-vascularized ectopic transplant mass, shown separated in FIG. 11c demonstrating that the ectopic transplant of the adult stem cells derived CTPs (generated from fat tissue) is biocompatible, well integrated within the recipient mouse and not rejected by its immune system.

Figure 12A:
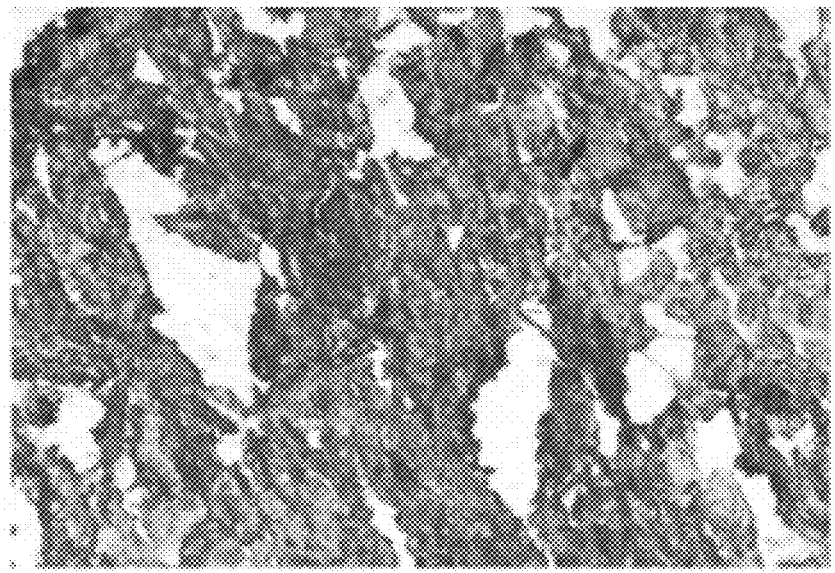
Figure 12B:
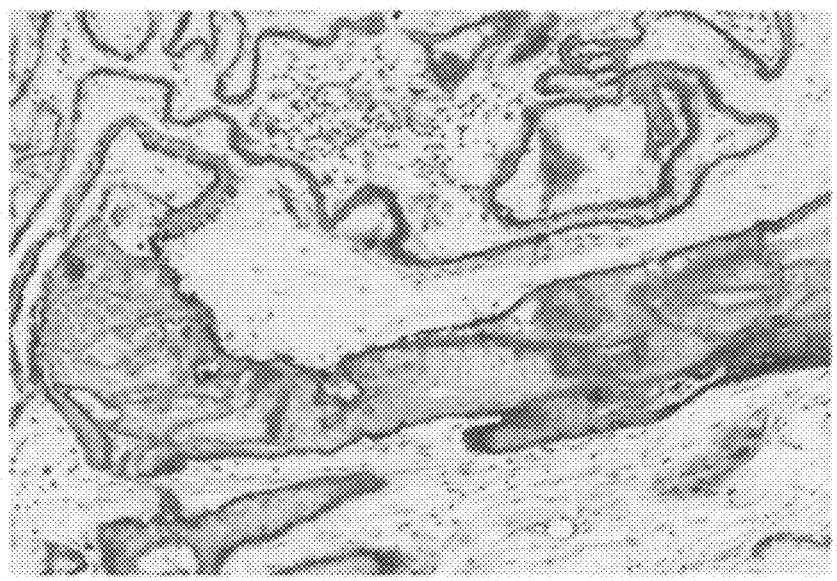

FIG. 12a-b are images of bone tissue formed following subcutaneous transplantation of the fat-derived CTPs (as described in the description of FIGS. 4 and 11). FIG. 12a—a frozen section of non-demineralized tissue demonstrating the formation of mineral deposits. Scale bar: 100 µm. FIG. 12b—histological section stained with H&E demonstrating the formation of bone tissue.

Figure 13A:
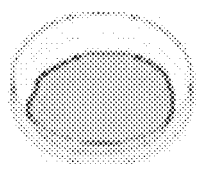
Figure 13B:
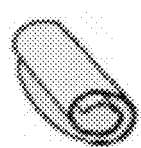
Figure 13C:
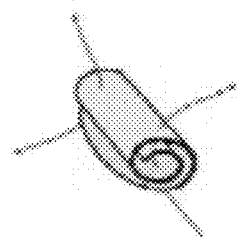
Figures 13D, 13E:
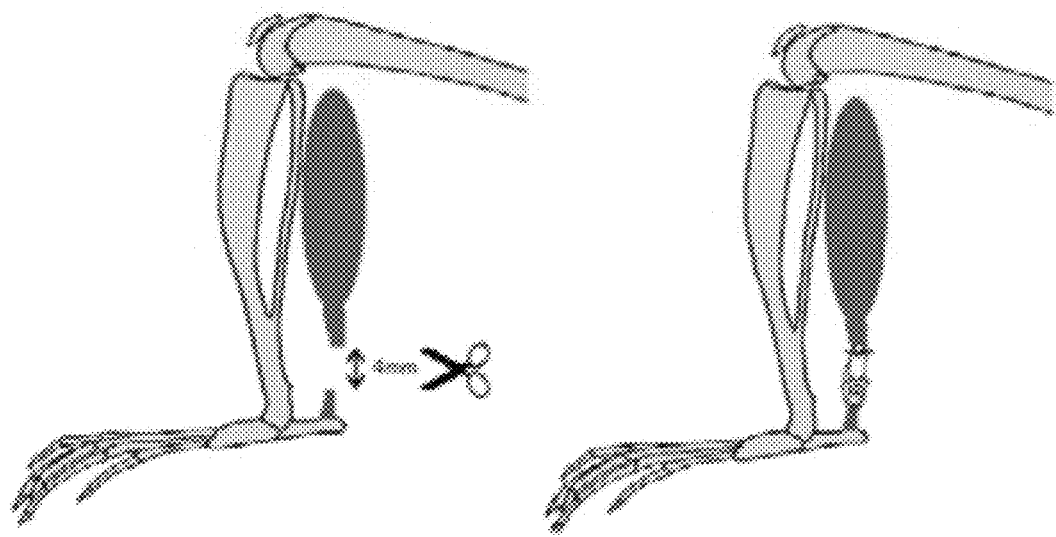

FIGS. 13a-e schematically depict the strategy of repairing critical Achilles-tendon injury by implanting a tendon graft formed from the hESCs derived CTPs of the present invention. FIG. 13a—High-density hESCs derived CTP cultures are grown with no further splitting for 4-5 weeks to form sheet-like tissues in culture plates. FIG. 13b—Once sheet-like tissues are formed, the tissues are gently removed from plates using a cell scraper and rolled to form rounded cylinders. FIG. 13c—Non-absorbable sutures are inserted at the ends of a construct through all layers. FIG. 13d—Constructs are immediately used for transplantation or kept inside custom-made templates made from flexible silicon tubes embedded in agar plates. Full thickness, 3-4 mm long segment of the Achilles tendon in nude mice is cut to form a critical gap. FIG. 13e—The tendon graft constructs are sutured to the proximal and distal edges of the injured Achilles tendon.

Figure 14A:
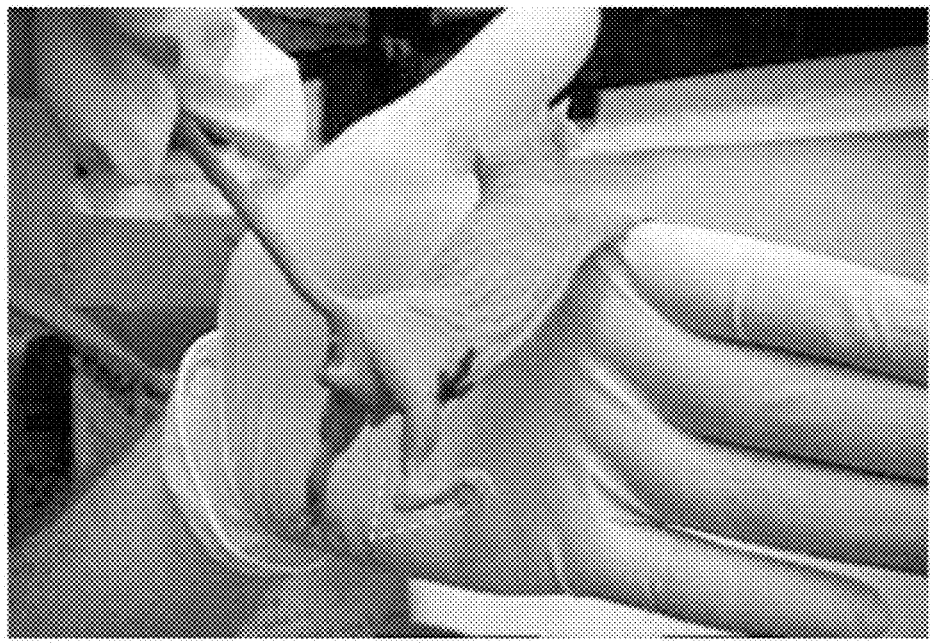
Figure 14B:
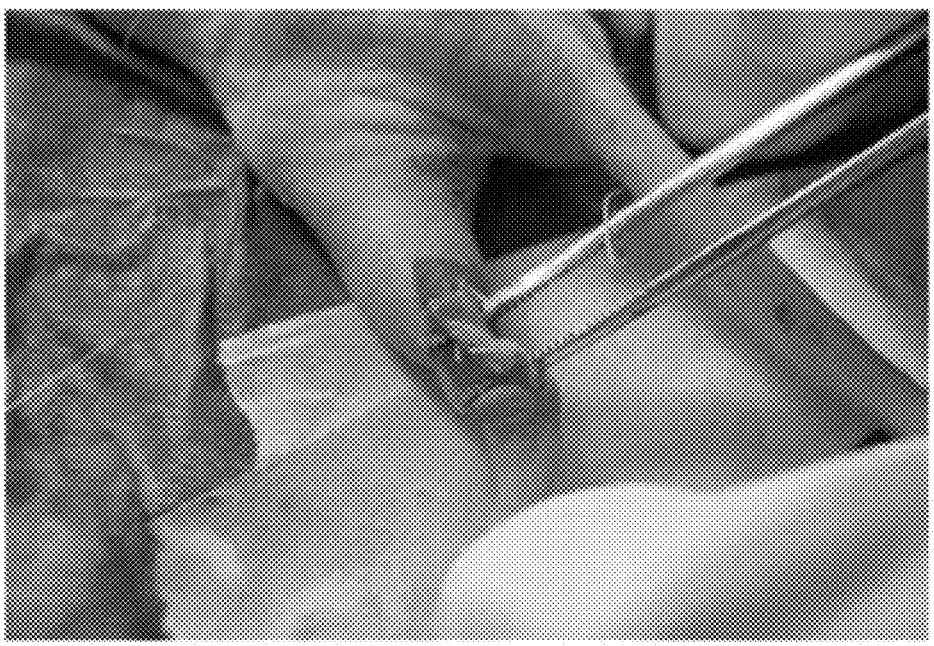
Figure 15A:
Figure 15B:
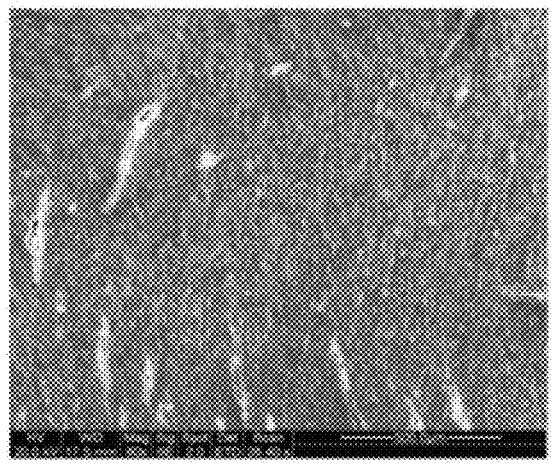
Figure 15C:
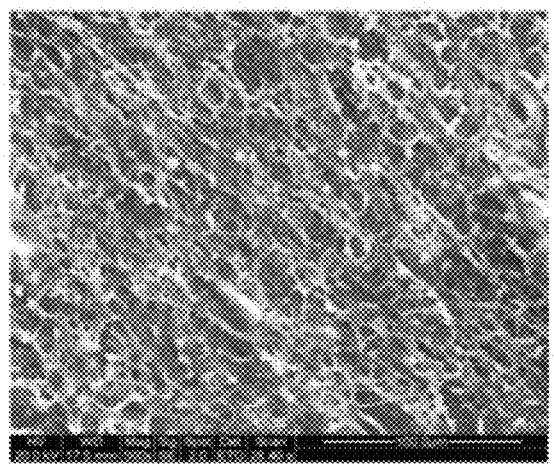
Figure 15D:
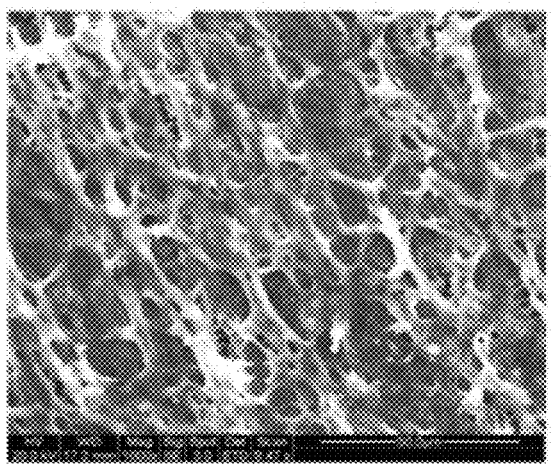
Figure 15E:
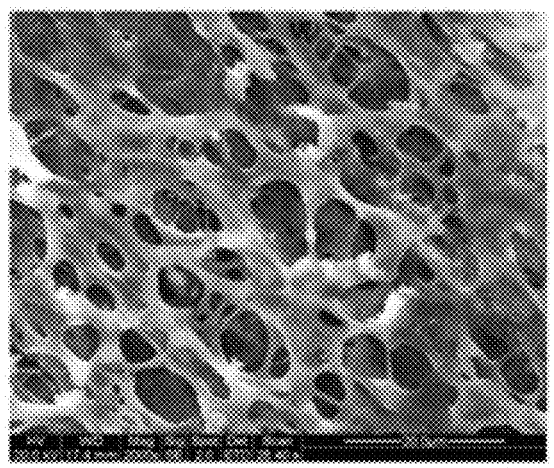
Figure 15F:
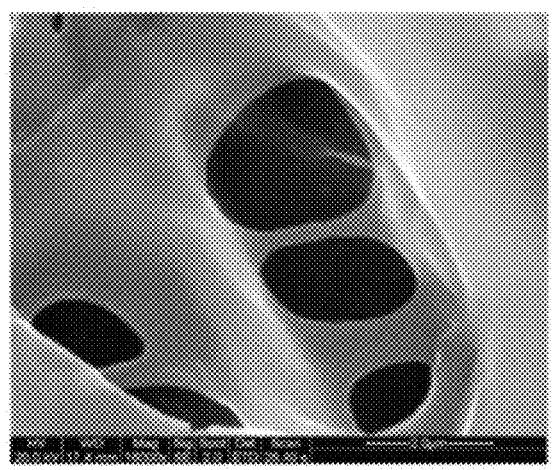

FIGS. 14a-b depict the repair of a critical Achilles-tendon injury in vivo following transplantation of a tendon which was formed in vitro from adult stem cells-derived CTPs (generated from fetal tissue). FIG. 14a—A macroscopic view of a non-transplanted animal which was subjected to critical Achilles-tendon injury (excision of the Achilles-tendon). Note that the mouse is unable to extent its ankle, resulting in a maximal extension of is less than 90 degrees (yellow lines). FIG. 14b—a macroscopic view of the in vitro formed tendon graft following its implantation into a mouse leg, replacing critically injured Achilles tendon.

FIGS. 15a-f depict macroscopic view (FIG. 15l) and SEM analyses (FIGS. 15b-f) of freeze dried engineered tissue, derived from fat-CTPs FIGS. 16a-f are SEM analyses of cells (293 human embryonic kidney cells) seeded on the freeze dried engineered tissue, derived from fat-CTPs (FIGS. 16b, 16d, 16f, and the corresponding tissues without seeded cells (FIGS. 16a, 16c, 16e), demonstrating the biocompatibility of the freeze dried engineered tissue.

Figure 16G:
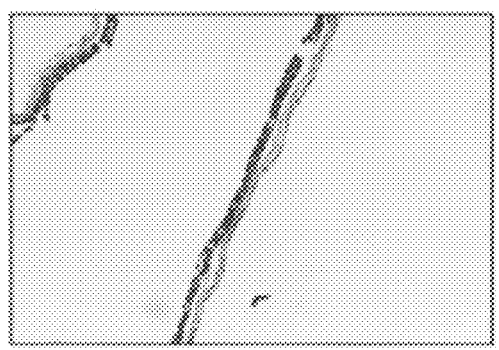
Figure 16H:
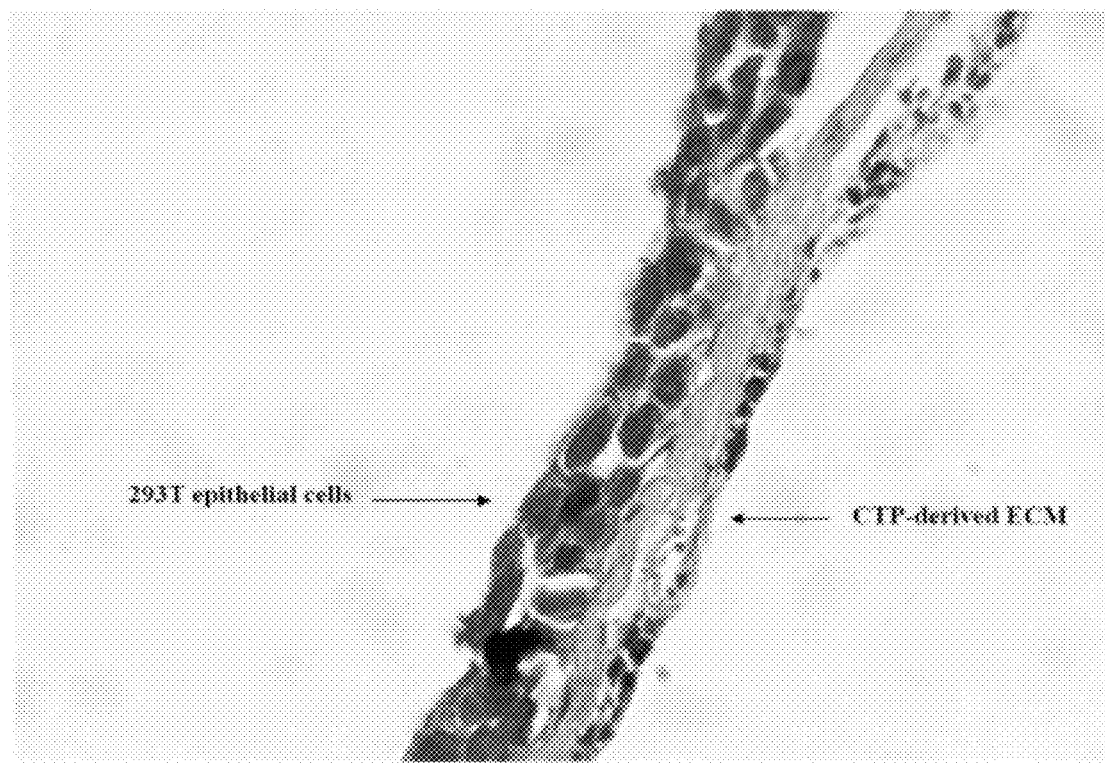

FIGS. 16g-h are histological sections of the 293 human embryonic kidney cells seeded on the freeze-dried engineered tissue, derived from fat-CTPs. FIG. 16g—low magnification (×100); FIG. 16h—high magnification (×400). Note the presence of the 293T epithelial cells and the CTP-derived ECM (marked by arrows).

Figure 17:
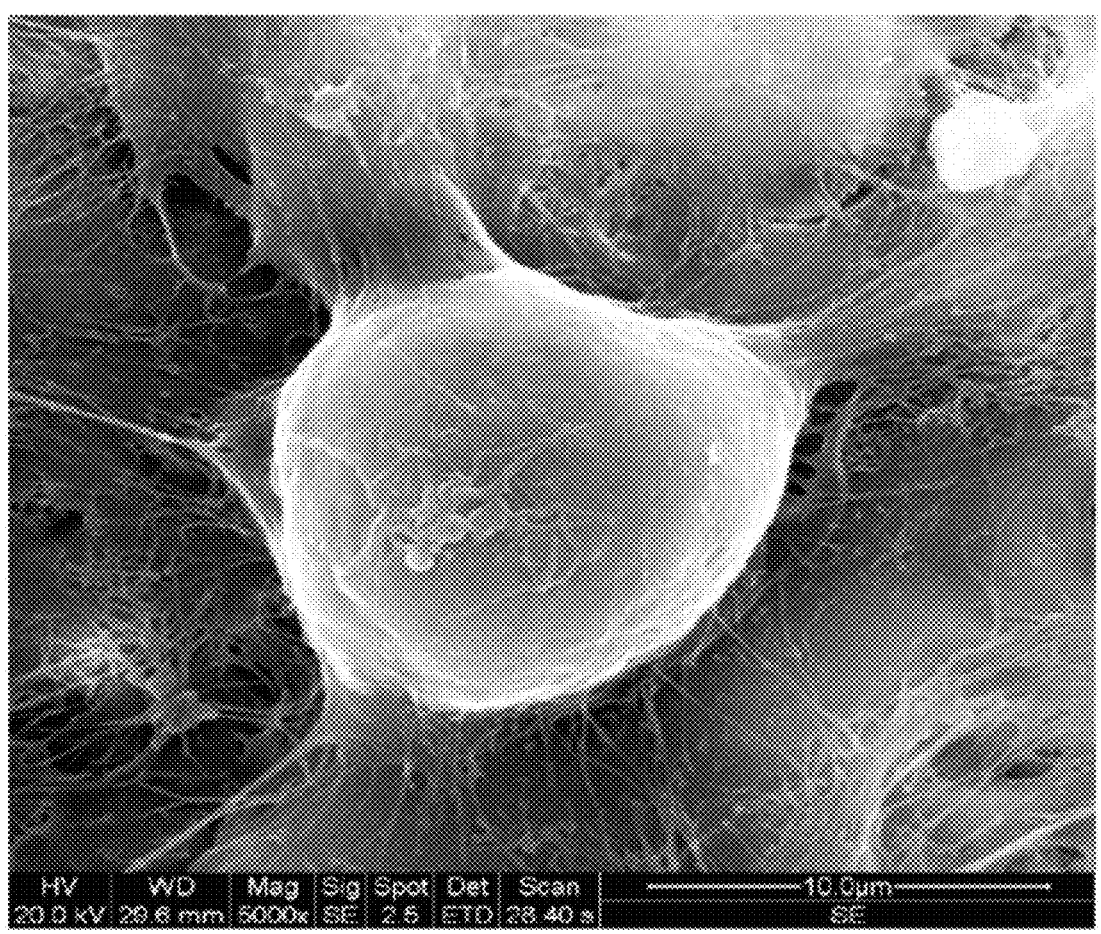

FIG. 17 is an image of SEM depicting high magnification of a single 293 human embryonic kidney cell seeded on the freeze dried engineered tissue shown in FIGS. 16a-h, producing nano scale, native ECM.

Figure 18A:
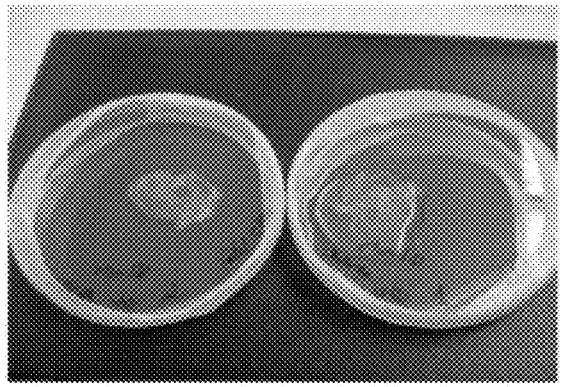
Figure 18B:
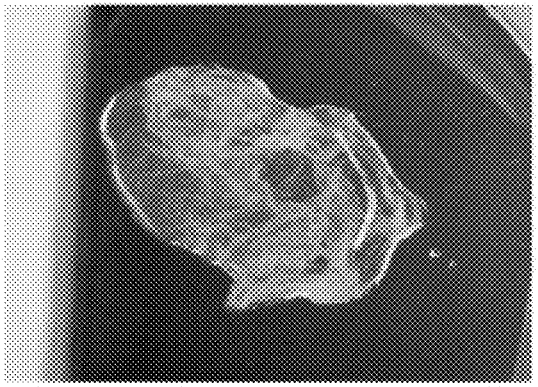
Figure 18C:
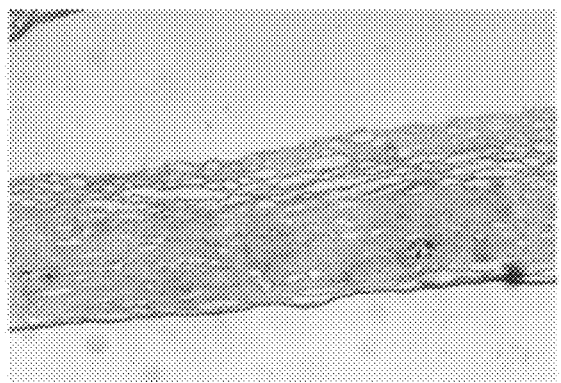
Figure 18D:
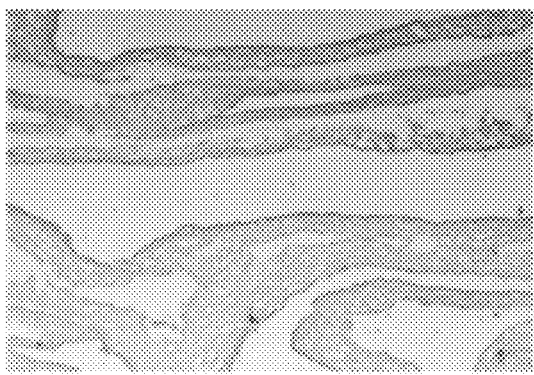
Figure 18E:
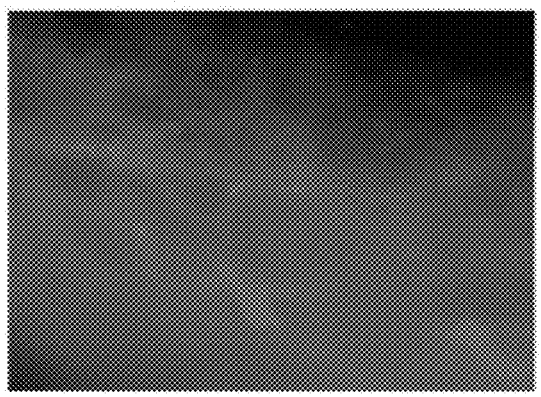
Figure 18F:
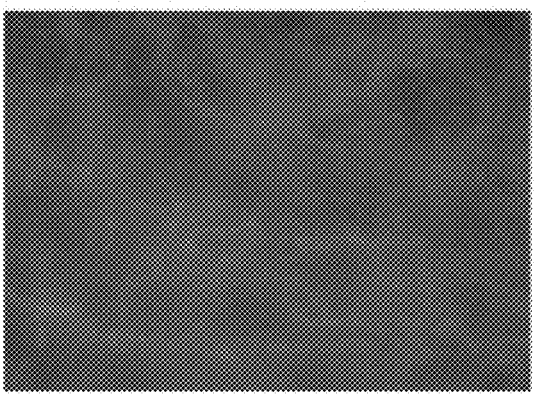

FIGS. 18a-f depict acellularized engineered tissue, derived from fat-CTPs. FIGS. 18a, b—macroscopic appearance of the acellularized engineered tissue. FIG. 18c—H&E staining of acellularized engineered tissue from fat derived CTPs. Note the absence of nuclei or other cellular components and the presence of fibrous ECM. FIG. 18d—fibronectin immunohistochemical staining [using the anti fibronectin antibody, Diagnostic BioSystems, Inc. (DBS) Pleasanton, Calif., USA, Cat. No. RP013] of the acellularized engineered tissue; FIG. 18e—Type I collagen immunofluorescence analysis of the acellularized engineered tissue; FIG. 18f—Type II collagen immunofluorescence (using the anti collagen type II antibody, Chemicon, Cat. No. MAB8887) analysis of the acellularized engineered tissue.

Figure 18G:
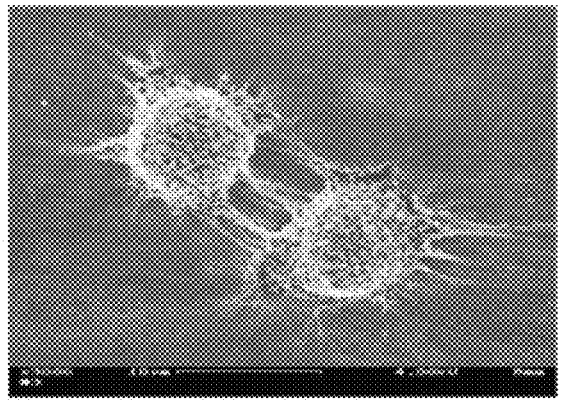
Figure 18H:
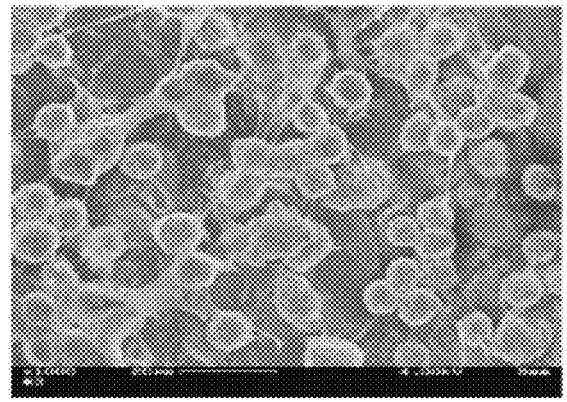
Figure 18I:
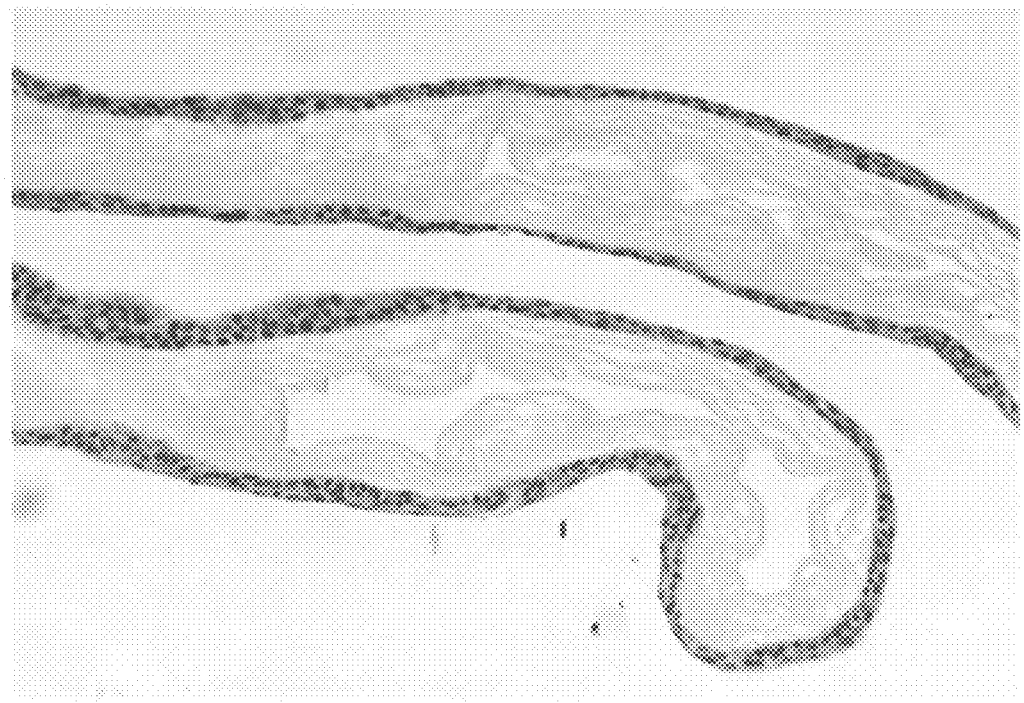

FIGS. 18g-i depict human keratinocyte cells (HACAT cell line) seeded on the acellularized engineered tissue derived from fat-CTPs one hour (FIGS. 18g, h) or 5 days (FIG. 18i) following seeding the cells on the acellularized engineered tissue. FIG. 18g—SEM analysis of two cells using ×3000 magnification (size bar=10 µm); FIG. 18h—SEM analysis of multiple cells using ×1000 magnification (size bar=20 µm). FIG. 18i—H&E staining of the seeded cells on the acellularized engineered tissue (magnification ×100). Altogether, these results demonstrate the biocompatibility of the de-cellularized engineered tissue.

Figure 19A:
Figure 19B:
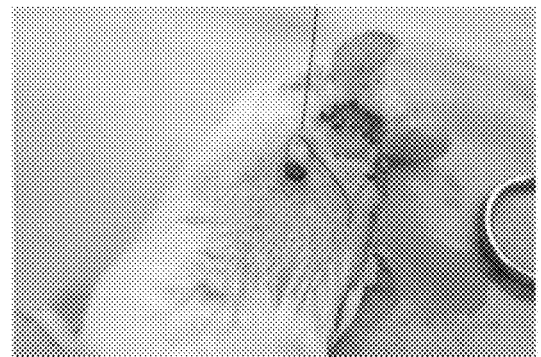
Figure 19C:
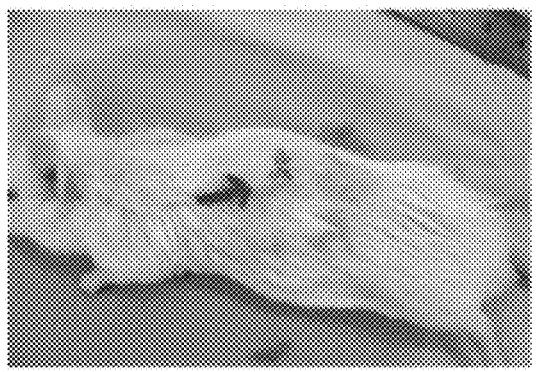
Figure 19D:
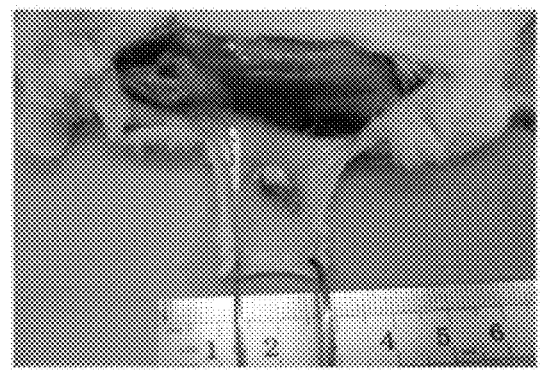
Figure 19E:
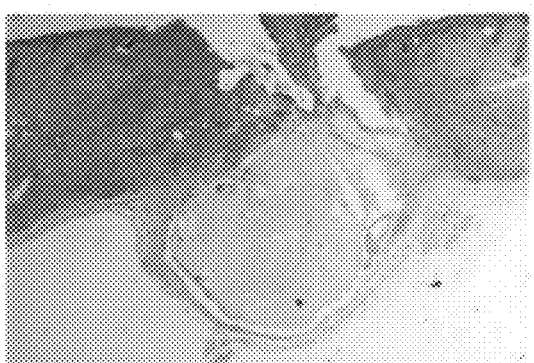
Figure 19F:
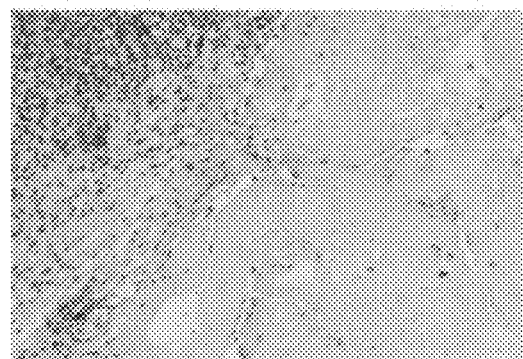

FIGS. 19a-f depict transplantation of the acellularized tissue (generated from fetal derived CTPs) in vivo. FIGS. 19a-b the acellularized freeze dried tissue is inserted through an incision in the skin of an ICR mouse. FIGS. 19c-d—macroscopic appearance of the transplanted tissue one week following transplantation. FIGS. 19*e-f*—histological sections of the transplanted tissue one week following transplantation stained with H&E.

DESCRIPTION OF THE PREFERRED EMBODIMENTS

The present invention is of methods of generating connective tissue progenitor cells (CTPs) from adult stem cells and of using such cells for cell based therapy and tissue engineering. Specifically, the present invention can be used to repair and regenerate damaged or diseased tissue by administering the CTPs of the present invention to a subject in need thereof or by implanting in the subject a tissue graft generated in vitro by the CTPs of the present invention.

The principles and operation of the method of generating connective tissue progenitor cells according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cell-based tissue engineering is an evolving interdisciplinary area that offers new opportunities for clinical applications, creating a tool for repairing and replacing damaged or lost tissues with biological substitutes. The current approaches of repairing damaged or disordered connective tissues, such as bone, cartilage and tendons include the use of autografts, allografts and artificial substitutes. However, while the use of cell grafts is limited by availability and morbidity, synthetic grafts are osteoconductively inferior to their biological counterparts, and could fail.

Thus, for cell based therapy and tissue engineering applications, methods of isolating and expanding stem or progenitor cells which can give rise to an unlimited amount of connective tissue cell lineages capable of forming connective tissue in vitro are highly desired.

Various studies attempted to identify culturing conditions which can be used to generate connective tissue progenitor cells that are capable of unlimited expansion in culture and which exhibit differentiation potential to cells of the connective tissue lineages. These include, for example, culturing of bone marrow-derived MSCs in a culture medium supplemented with serum (see e.g., Pittenger, M. F et al, 1999); culturing of bone-derived cells in a culture medium containing serum and fibroblast growth factor (FGF-2) (Sottile, et al., 2002); culturing of processed lipoaspirate (PLA) cells in a culture medium (DMEM) supplemented with serum (Zuk, P. A., et al., 2001); culturing adipose derived stem cells in a medium containing N-acetyl-L-cysteine, an antioxidant (e.g., vitamin C) and nicotinamide (U.S. Pat. Appl. No. 20050260748); and culturing of skeletal muscle cells in a culture medium containing fibroblast growth factor (FGF-2) and dexamethason (Mastrogiacomo, M., et al., 2005). However, although cells isolated from early passages (e.g., passage 1 or 2) of such culturing conditions exhibited a differentiation potential into various cell lineages such as the osteogenic, chondrogenic and adipogenic cell lineages, the differentiation potential of such cells from later passages such as passage 20 was never shown. In addition, some culturing conditions (e.g., those taught by Sottile, et al., 2002 and Zuk, P. A., et al., 2001) resulted in slow proliferation rate of the cells which limits their use for therapeutic and pharmaceutical applications. Moreover, the use of such culturing conditions for the construction of engineered tissues (e.g., a mature tissue such as a tendon tissue) in the absence of scaffold or carrier or for cell based therapy was never demonstrated.

While reducing the present invention to practice, the present inventors have uncovered that culturing of connective tissue progenitor (CTP) cells isolated from adult tissue can be performed in a culture medium which comprises cortisol (e.g., dexamethasone) and ascorbic acid and that cells cultured in such a culture medium and subject to serially passaging can be expanded in vitro for extended periods of time (e.g., at least 20 passages) and maintain their multipotent differentiation potential. This is in sharp contrast to other studies which used dexamethason and ascorbic acid in order to induce the terminal differentiation of the progenitor cells into the osteogenic lineage (see for example, Mastrogiacomo, M., et al., 2005; Pittenger, M. F et al, 1999; Sottile, et al., 2002; U.S. Pat. Appl. No. 20050260748 and Zuk, P. A., et al., 2001).

As is shown in the Examples section which follows, the CTPs generated according to the method of the present invention are highly proliferative cells and can be expanded in culture for at least 20 passages while maintaining, even following 20 passages, their differentiation potential to any of the connective tissue cell type. In addition, as is further shown in the Examples section which follows, the CTPs of the present invention were capable of differentiating into the osteogenic lineage, the chondrogenic lineage, cartilage lineage (cartilage cells), tendon and ligament lineage (tendon cells, ligament cells) and ECM-forming cells. In addition, CTPs of the present invention were capable of forming a functional tendon without using any scaffold or carrier. Moreover, when transplanted into mice, the CTPs of the present invention were capable of forming a loose connective tissue, a bone tissue and a cartilage tissue in vivo.

Thus, according to one aspect of the present invention there is provided a method of generating connective tissue progenitor cells. The method is effected by culturing adult stem cells in a culture medium which comprises cortisol and ascorbic acid so as to allow differentiation of the adult stem cells into connective tissue progenitor cells, wherein the connective tissue progenitor cells are capable of differentiating into at least two cell lineages of the connective tissue; thereby generating the connective tissue progenitor cells.

As used herein the phrase "connective tissue progenitor cells (CTPs)" refers to cells which are capable of differentiating to more than one cell lineage and/or cell type of a connective tissue. Examples of connective tissues include, but are not limited to dense connective tissue (e.g., ligament, tendon, periodontal ligament), areolar connective tissue (e.g., with proteinaceous fibers such as collagen and elastin), reticular connective tissue, adipose tissue, blood, bone, cartilage, skin, intervertebral disc, dental pulp, dentin, gingival, extracellular matrix (ECM)-forming cells, loose connective tissue and smooth muscle cells.

Preferably, the connective tissue progenitor cells of the present invention are capable of differentiating into at least two, more preferably, at least three, more preferably, at least four cell lineages or cell types of the osteogenic lineage, a chondrogenic lineage, an adipocytic lineage, tendon cells, ligament cells, areolar connective tissue and ECM-forming cells.

The phrase "adult stem cells" as used herein refers to cells obtained from a fetal tissue (i.e., taken from a conceptus post implantation until birth) or a post natal tissue (i.e., a tissue from a newborn or adult individual) which are capable of differentiation into other cell types and/or cell lineage. Preferably, the adult stem cells are obtained from a mammal such as primate or human being, preferably, the adult stem cells are derived from a fetal or a post natal human being.

The adult stem cells of the present invention can be isolated from various biological samples which contain adult stem cells of a fetal or a post natal tissue. Non-limiting examples of biological samples containing adult stem cells of a fetal tissue which can be used along with the method of this aspect of the present invention include a placental tissue which can be obtained from a placental biopsy of an ongoing pregnancy, or following pregnancy termination (using, e.g., a syringe with a needle); chorionic villi sample (CVS) which can be obtained from an ongoing pregnancy (between the 9-14 weeks of gestation) by inserting a catheter through the cervix or a needle into the abdomen and removing a small sample of the placenta (i.e., chorionic villus); amniocytes which can be obtained via amniocentesis of an ongoing pregnancy usually between the $16^{th}$ to the $20^{th}$ week of gestation (can be also performed on a later gestational week) by inserting a thin needle through the abdomen into the uterus; cord blood sample which can be obtained via cordocentesis of an ongoing pregnancy (at any gestation week following the $17^{th}$ week of gestation) by inserting a thin needle through the abdomen and uterine walls to the umbilical cord; amniotic membrane which can be obtained from a terminated pregnancy or immediately after birth by removal of the amniotic sac.

Non-limiting examples of biological samples containing adult stem cells of a post-natal tissue which can be used along with the method of this aspect of the present invention include Wharton's jelly (the matrix present within the umbilical cord) and cord blood which can be obtained from the umbilical cord of a newborn individual shortly after birth; foreskin cells (e.g., foreskin fibroblasts) which can be obtained from a newborn or older individual via circumcision; fibroblasts of any connective tissue (see for example, Rieske P, Krynska B, Azizi S A., 2005, Differentiation, 73: 474-83); bone marrow which can be obtained at any age using a syringe needle (bone marrow aspirates) from the iliac crest, femora, tibiae, spine, rib or other medullar spaces; fat tissue which can be obtained from subcutaneous, breast or perirenal sites, using liposuction surgery or penniculectomy; connective tissue (e.g., loose or dense connective tissue, such as bone tissue) which can be obtained using common biopsy obtaining methods.

Prior to culturing, the adult stem cells are preferably isolated from the biological sample containing thereof. Methods of isolating adult stem cells are known in the arts and include, for example, those disclosed in http://www[[.]]dotworthington-biochem[[.]]dotcom/default[[.]]dothtml or provided along with the Cell Isolation Optimizing System (catalogue no. LK003200; Worthington Biochemical Corporation); Alison, M. R. [Tissue-based stem cells: ABC transporter proteins take center stage. J Pathol. 2003 200(5): 547-50], Cai, J. et al., [Identifying and tracking neural stem cells. Blood Cells Mol Dis. 2003 31(1): 18-27] and Collins, A. T. et al., [Identification and isolation of human prostate epithelial stem cells based on alpha(2)beta(1)-integrin expression. J Cell Sci. 2001; 114(Pt 21): 3865-72].

Briefly, in order to isolate adult stem cells of a fetal or a post natal tissue which includes dense matrix associated or connective proteins (such as elastin and collagen), the tissue can be first minced using a scalpel or a razor blade to small pieces (e.g., tissue chunks of 2-5 mm), following which the tissue is subjected to an enzymatic digestion using an enzyme such as dispase, collagenase (e.g., type I, II, III or IV), trypsin, natural protease, elastase, papain. Digestion enzymes can be obtained from various suppliers such as Sigma (St Louis, Mo., USA) and Worthington. It will be appreciated that selection of the type of digestion enzyme for dissociating the biological sample containing the adult stem cells is depended on the composition of the proteins in the tissue and those of skilled in the art are capable of selecting the suitable enzyme for each type of tissue. For example, for the digestion of tissues such as a placental tissue, chorionic villi sample (CVS), amniotic membrane, foreskin, bone, adipose tissue (fat) and loose connective tissue which include collagen, type II collagenase may be used. On the other hand, for the digestion of a tissue which is rich in elastin such as the Wharton's jelly of the umbilical cord, elastase may be used.

For example, a biological sample containing an adult tissue (e.g., an adipose tissue, CVS, placental tissue, amniotic membrane, cord, foreskin, bone, and loose connective tissue) can be dissociated using type II Collagenase at a concentration between 0.01-0.5%, preferably 0.04-0.2%, most preferably 0.1%, at temperatures between 25-50° C., preferably between 33-40° C., more preferably, at 37° C., for incubation periods which may be effected from 30 minutes to 24 hours. It will be appreciated that the time of incubation with the digestion enzyme depends on the type of tissue. For example, while for adipose tissue, 1-3 hours of digestion are sufficient, for bone tissue, complete digestion may require 18-24 hours or even more. Similarly, for digestion of CVS, placental tissue, amniotic membrane, the sample is incubated with the digestion enzyme, for digestion of, the sample is incubated for 1-10 hours with the digestion enzyme, for digestion of foreskin, the sample is incubated over night with the digestion enzyme, for digestion of loose connective tissue, the sample is incubated over night with the digestion enzyme. It will be appreciated that to increase digestion efficiency, the incubation with the digestion enzyme is preferably performed under agitation (e.g., by 40 RPM). It should be noted that measures are taken in order to dissociate the large cell aggregates to small cell clumps or preferably to single cells without hampering the cell structure and viability. It will be appreciated that the morphology of the dissociated adult stem cells can be monitored using an inverted microscope and the viability of the cells can be measured by subjecting a sample of the cells to the Live/Dead viability assay (Molecular Probes, Molecular Probes, Inc., Eugene, Oreg., USA).

Preferably, following enzymatic digestion, the biological samples are subjected to differential centrifugation as is further described hereinunder.

Alternatively, isolating adult stem cells from tissue samples which are devoid of or have non-significant amounts of collagen, such as cord blood and bone marrow, can be performed by directly subjecting the sample to a differential centrifugation according to known techniques as described elsewhere [Halvorsen, et al, Metabolism 2001, 50:407-413; Hauner, et al, J Clin Invest 1989, 84:1663-1670; Rodbell, et al, J Biol Chem 1966, 241:130-139].

Differential centrifugation can be performed in a culture medium or over a gradient such as Ficoll or Percoll. Cells are centrifuged at speeds of between 100 to 3000×g, more preferably 200-1500×g, more preferably at 500×g, for periods of between 1 minute to 1 hour, more preferably 2 to 15 minutes, more preferably 5 minutes, at temperatures of between 4-50° C., preferably between 20-40° C., more preferably at 25° C. Thus, cells Still alternatively, isolation of adult stem cells from amniocytes can be performed by directly subjecting the amniotic fluid sample to centrifugation which separates the cells from the amniotic fluid.

As mentioned, once isolated the adult stem cells are cultured in a culture medium comprising cortisol and ascorbic acid.

Culturing the adult stem cells according to this aspect of the present invention is effected by seeding the adult stem cells in a culture vessel (e.g., a tissue culture plate, flask, container or bottle) at a cell density which promotes differentiation of the adult stem cells into connective tissue progenitor cells which are capable of proliferation in culture while maintaining their multipotent capacity. For example, a suitable cell density which can be used to generate the CTPs of the present invention may be $1 \times 10^5$-$1 \times 10^6$ cells per $cm^2$, more preferably, $5 \times 10^5$-$1 \times 10^6$ cells per $cm^2$ (e.g., $5 \times 10^5$ cells per $cm^2$). Culturing conditions usually include incubation of the cells at physiological temperatures in the range of 35-38° C. (preferably, 37° C.), under humidity and in the presence of 5% $CO_2$.

The culture medium used by the method of this aspect of the present invention may be any culture medium capable of supporting the growth of the CTPs of the present invention while maintaining their proliferative and multipotent capacities. Such a culture medium can be a water-based medium which includes a combination of substances such as salts, nutrients, minerals, vitamins, amino acids, nucleic acids, proteins such as cytokines, growth factors and hormones, all of which are needed for maintaining CTP proliferation and differentiation levels. For example, a culture medium according to this aspect of the present invention can be a synthetic tissue culture medium such as alpha-MEM (Biological Industries, Beit Haemek, Israel), Ko-DMEM (Gibco-Invitrogen Corporation products, Grand Island, N.Y., USA), DMEM/F12 (Biological Industries, Biet Haemek, Israel), supplemented with the necessary additives as is further described hereinunder. Preferably, all ingredients included in the culture medium of the present invention are substantially pure, with a tissue culture grade.

As used herein the term "cortisol" refers to a synthetic or naturally occurring cortison (a glucocorticoid steroid hormone) which binds the glucocorticoid receptor and is capable of expanding CTPs and maintaining their differentiation state. It will be appreciated that the method of this aspect of the present invention can use a variety of cortisol derivatives or analogues which are capable of the biological activity (e.g., expanding CTPs and maintaining their differentiation state). Non-limiting examples of cortisol derivatives or analogues which can be used according to this aspect of the present include hydrocortisone, cortisone acetate, prednisone, prednisolone, methylprednisolone, dexamethasone (about 40 times more potent), betamethasone, triamcinolone, beclometasone, fludrocortisone acetate and deoxycorticosterone acetate (DOCA). Preferably, the cortisol analogue used by the method of this aspect of the present invention is dexamethasone, which is known to have a potent activity (about 40 times more than hydrocortisone) mediated by the glucocorticoid receptor.

The dexamethasone which is included in the culture medium of this aspect of the present invention can be obtained from Sigma (St Louis, Mo., USA) and is provided at a concentration selected from the range of $10^{-5}$-$10^{-8}$ M, e.g., at least $10^{-7}$ M. For example, as described under "General Materials and Experimental Methods" of the Examples section which follows, the present inventors have used $10^{-7}$ M dexamethasone within the culture medium to obtain a highly proliferative, multipotent CTPs.

As used herein "ascorbic acid" refers to the synthetic or naturally occurring ascorbic acid (an organic acid with anti-oxidant properties), also known as vitamin C, which is suitable for culturing cells (e.g., sterile preparation).

The ascorbic acid which is included in the culture medium of the method of this aspect of the present invention can be obtained from Sigma (St Louis, Mo., USA) and is provided at a concentration of at least 20 µg/ml, more preferably, at least 30 µg/ml, preferably, at a concentration which is selected from the range of 20-500 µg/ml, more preferably, at a concentration which is selected from the range of 20-200 µg/ml, more preferably, at a concentration which is selected from the range of 30-100 µg/ml, e.g., 50 µg/ml. For example, as described under "General Materials and Experimental Methods" of the Examples section which follows, the present inventors have used 50 µg/ml ascorbic acid within the culture medium to obtain a highly proliferative, multipotent CTPs.

As is shown in FIGS. 8a-d and is described in Example 3 of the Examples section which follows, the CTPs generated by the method of this aspect of the present invention are capable of forming mineralized matrix. Preferably, in order to increase the deposition of mineralized matrix (e.g., when differentiation into a bone tissue is desired), the culture medium further includes inorganic phosphate such as beta-glycerophosphate, which can be obtained from Sigma (St Louis, Mo., USA). The inorganic phosphate included in the culture medium is provided at a concentration in the range of 0.01-1000 mM, preferably, at a concentration of 1-50 mM, even more preferably, at a concentration of 10 mM.

Preferably, the culture medium used according to the method of this aspect of the present invention further comprises serum or serum replacement (e.g., a defined preparation made of mainly synthetic or recombinantly expressed proteins which replaces the serum in a culture medium). Such sera can be derived from a human source (human serum) or from an animal source (e.g., bovine serum, horse serum) and can be obtained from a variety of tissue culture suppliers such as Hyclone (Utah, USA), Invitrogen (Grand island, N.Y., USA) or Biological Industries (Biet Haemek, Israel). A preparation of serum replacement can be obtained from Gibco-Invitrogen Corporation (Grand Island, N.Y. USA).

The serum or serum replacement used by the method of this aspect of the present invention is provided at a concentration range of 1% to 40%, more preferably, 5% to 35%, more preferably, 10% to 30%, more preferably 10% to 20%, e.g., 15%.

Preferably, culturing according to this aspect of the present invention is effected under xeno-free culturing conditions, i.e., under conditions which are devoid of animal contaminants (e.g., animal pathogens such as retroviruses). Thus, the serum which is included in the culture medium of the present invention is preferably human serum or serum replacement, and culture medium additives (e.g., the growth factors, minerals, vitamins or hormones such as dexamethasone and ascorbic acid) are preferably synthetic or recombinantly expressed highly pure additives.

It will be appreciated that the CTPs of the present invention can grow in the above-described culture medium by either directly attaching to the wall of the culture vessel (e.g., the bottom of a culture flask) or by attaching to feeder cells which are attached to the wall of the culture vessel. Feeder cells are cells such as stromal cells, fibroblast cells (e.g., foreskin fibroblasts, human embryonic fibroblasts) or human fallopian epithelial cells, which secrete growth factors and/or nutrients and support the growth of the cells-of-interest (e.g., stem or progenitor cells) cultured therewith. However, it will be appreciated that culturing conditions which rely on feeder cells are much more complicated since they require the separation of the cells-of-interest from the feeder cells at each passaging step and thus may result in mixed populations of cells.

Preferably, culturing according to the method of this aspect of the present invention is effected under feeder-free culturing conditions. As used herein the phrase "feeder-free culturing conditions" refers to culturing conditions which are devoid of feeder cells. For example, as shown in the Examples section which follows, the CTPs of the present invention (which are cultured under feeder-free culturing conditions) are completely devoid of feeder cells and thus represent a pure population of CTPs.

Preferably, the method of this aspect of the present invention further comprising passaging the connective tissue progenitor cells in a presence of the culture medium which comprises cortisol (e.g., dexamethasone) and ascorbic acid, wherein a first passage of the passaging is effected no more than 10 days following initial culturing of the adult stem cells in the culture medium.

The term "passaging" as used herein refers to splitting the cells so that the cells can grow beyond confluency. The term "confluency" as used herein refers to a density of adherent cells which when attached to a wall of a culture vessel cover 100% of its area. Preferably, in order to prevent the differentiation of the CTPs of the present invention to terminally differentiated cells (e.g., osteoblasts) or to cells with limited differentiation potential (e.g., precursors which are restricted to a specific cell lineage), the first passaging occurs when the cells in the culture reach subconfluency, i.e., when the cells cover about 70-90% of the culture vessel wall, more preferably, when the cells cover about 80-90% of the culture vessel wall. Preferably, when cultured according to the teachings of the present invention subconfluency of the cells in the culture occurs no more than 10 days of the initial seeding of the cells. Preferably, the cells are serially passaged after no more than 9 days in culture, more preferably, after no more than 8 days in culture, more preferably, after no more than 7 days in culture, more preferably after about 4-6 days in culture.

Passaging according to this aspect of the present invention can be performed by dissociating cells from the wall of the culture vessel using e.g., type IV collagenase (at a concentration of 0.1% for 20-60 minutes) followed by trypsinization (using 0.25% trypsin for 2-5 minutes), counting the single cells and splitting the cells to 2-5, preferably to 4 tissue culture vessels (i.e., a splitting ratio of 1:4) in order to preserve the same cell density of their initial seeding (e.g., $5\times10^5$-$1\times10^6$ cells per cm$^2$). Preferably, the cell culture is subjected to culture passaging every 3-6 days, preferably, culture passaging occurs every 2-5 days, e.g., every 4 days.

Preferably, passaging according to the method of this aspect of the present invention is performed for at least 20 times, more preferably, at least 25 times, more preferably, at least 30 passages, while splitting the cells using a splitting ratio of 1:3, more preferably, a splitting ratio of 1:4 (a splitting ratio of 1:4). As described in the Examples section which follows, the CTPs of the present invention were serially passaged every 4 days for at least 25 passages.

Preferably, passaging according to the method of this aspect of the present invention is effected under xeno-free and/or feeder-free conditions.

In addition, the method of this aspect of the present invention preferably comprises a step of isolating the CTPs (i.e., separating the CTPs from the culture medium). Isolating the cells can be effected at any time while in culture, e.g., prior to the first culture passaging, following the first culture passaging, or following any other culture passaging. Thus, the CTPs can be isolated by filtration (e.g., using a membrane which prevents the passage of CTPs and enables passage of the medium and/or by centrifugation of the cells (e.g., using a conical tube centrifugation at 1500 RPM).

Preferably, the method of this aspect of the present invention further comprises expanding the CTPs. As used herein the phrase "expanding" refers to increasing the number of the connective tissue progenitor cells over the culturing period without hampering their differentiation capacity.

Preferably, CTPs generated and isolated according to the method of this aspect of the present invention are highly proliferative cells. For example, adult stem cells-derived CTPs exhibited a tripling time (i.e., the hours between passages in which the cell number was triplicated) of 80-100 hours during passages 1-18 and of 120-140 hours during passages 19-25 (data not shown).

Preferably, expanding of the connective tissue progenitor cells in the culture medium which comprises cortisol (e.g., dexamethasone) and ascorbic acid is effected such that at least $3.5\times10^9$ connective tissue progenitor cells are obtained from a single cell of the adult stem cells following about 20 passages.

As is shown in FIGS. 1a-g and is described in Example 2 of the Examples section which follows, FACS analysis revealed that the CTPs isolated according to the method of this aspect of the present invention express on their cell surface CD105 (a marker of endothelial cells, also known as Endoglin, GenBank Accession No. NP_000109.1), CD166 (activated leukocyte cell adhesion molecule, also known as ALCAM, GenBank Accession No. NP_001618.2), CD44 (e.g., GenBank Accession No. NP_000601.3, NP_001001389.1, NP_001001390.1, NP_001001391.1, NP_001001392.2), CD29 (ITGB1; e.g., GenBank Accession No. NP_002202.2, NP_391987.1, NP_391989.1, NP_391988.1, NP_596867.1, NP_389647.1) and HLA-ABC. On the other hand, the CTPs of the present invention do not express CD45 (PTPRC; e.g., GenBank Accession No. NP_002829.2, NP_563579.1, NP_563578.1, NP_563580.1) and HLA-DR, thus resembling the expression profile of other mesenchymal stem cells like cells.

As used herein the phrases "expressing" or "not expressing" refer to cells having a positive (+) or negative (−) expression profile, respectively, of a certain marker (e.g., gene or gene product).

Thus, the present invention provides an isolated cell preparation of adult stem cells—derived CTPs. Preferably, the connective tissue progenitor cells of the isolated cell preparation are capable of being maintained in a proliferative, non terminally differentiated state for at least 20 passages in culture.

The phrase "non terminally differentiated state" as used herein refers to cells which are capable of differentiating to at least two cell lineages of the connective tissue even following 20 passages in culture. For example, as is shown in FIGS. 2a-u and is described in Example 2 of the Examples section which follows, adult stem cells-derived CTPs from various passages (e.g., from passages 1-25) express markers of osteogenic lineage, the chondrogenic lineage, cartilage cells, tendon cells, ligament cells and ECM-forming cells. Moreover, as described in the Examples section which follows, when cultured in vitro in the presence of inorganic phosphate, the adult stem cells—derived CTPs formed bone nodules (bone tissue) containing calcium-phosphate deposits, the major component of bone minerals. In addition, when induced to differentiate into the chondrogenic lineage (using the "intact layer" method), adult stem cells—derived CTPs formed a fibrous ECM (FIGS. 9a-b, Examples 4 of the Examples section which follows).

Thus, while further reducing the present invention to practice, the present inventors have uncovered that the CTPs of the present invention can be used to generate a connective tissue.

Preferably, the connective tissue which can be formed from the CTPs of the present invention is a bone tissue (e.g., osseous tissue), a connective tissue (e.g., loose connective tissue), an extracellular matrix (ECM), a tendon tissue, a ligament tissue and a cartilage tissue.

For example, to form a bone tissue, the isolated cell preparation of the CTPs of the present invention are cultured in a medium containing dexamethasone, ascorbic acid and inorganic phosphate (e.g., α-MEM supplemented with 15% serum, $10^{-7}$ M dexamethasone, 50 μg/ml ascorbic acid and 10 mM (β-glycerphosphate) and let to become over-confluent (i.e., they occupy more than 100% of the area of the culture vessel wall and thus form multilayers) for a period of at least 10 days before mineralization appears. The culture medium is occasionally replaced every 4-8 days without culture passaging. The presence of bone tissue can be determined by RNA-based methods (e.g., RT-PCR, in situ RNA hybridization and cDNA microarray) or protein-based methods (e.g., immunological staining) for bone specific markers such as core binding factor alpha 1 (CBFA1), SOX9, type I collagen (Col-I), osteonectin, osteopontin, parathyroid hormone receptor 1 (PTHR1) and alkaline phosphatase. In addition, the ultrastructural and chemical data of bone tissue can be determined using, for example, energy dispersive spectroscopy (EDS), scanning electron microscopy (SEM) and/or confocal Raman spectroscopy (CRS) analyses essentially as described elsewhere [Ubelaker D H, et al., J Forensic Sci. 2002 September; 47(5):940-3; van Apeldoorn A A, et al., J R Soc Interface. 2005 Mar. 22; 2(2):39-45].

For the formation of connective tissue, the isolated cell preparation of the CTPs of the present invention are preferably seeded on a suitable 3D environment (e.g., a scaffold such as an electrospun, PCL/PLA nanofiber scaffold) that would support their growth and organization into a complex connective tissue which produces ECM. Briefly, $5 \times 10^5$ CTPs resuspended in 10 μl of CTP medium (α-MEM supplemented with 15% serum, $10^{-7}$ M dexamethasone, 50 μg/ml ascorbic acid) are seeded on a scaffold and grown in the presence of the CTP medium for about one month. The presence of connective tissue and ECM can be determined by RNA or protein-based methods for markers such as type III (Col-III) and type XII (Col-XII) collagens, decorin, biglycan, elastin, fibronectin, and tenascin-C, as well as using scanning electron microscopy (SEM) analysis.

For the formation of extracellular matrix (ECM), the isolated cell preparation of CTPs are plated at high densities in tissue culture plates in the presence of a culture medium comprising ascorbic acid and preferably also dexamethasone. After about 4 weeks in culture (other periods of time are possible too) sheet-like tissue is formed. The sheet-like tissue can be further subject to freeze-drying and/or cell removal as shown in FIGS. 15-18 and is described in Example 10 of the Examples section which follows. Thus, the ECM can be intact matrix (which can be freeze dry, and/or subjected to acellularization for further tissue engineering applications, tissue replacement, tissue repair and the like, and/or it can be a soluble ECM which can be used as an injectable material for tissue engineering applications, tissue replacement, tissue repair and the like.

For the formation of ligament-forming cells, the isolated cell preparation of the CTPs of the present invention are cultured for at least one week in the presence of medium containing dexamethason and ascorbic acid (e.g., α-MEM supplemented with 15% serum, $10^{-7}$ M dexamethasone, 50 μg/ml ascorbic acid). The presence of ligament-forming cells can be detected by RNA or protein-based methods for markers such as scleraxis and type I Collagen.

For the formation of a cartilage tissue, two main methods can be employed: the "intact layer" method (removal of subconfluent CTP cultures without pre-collagenase treatment and culturing the intact layer in a CTP medium, essentially as described in the Examples section) and the "pellet culture" method (spherical pellets which are cultured in medium supplemented with serum, dexamethasone, ascorbate-2-phosphate and TGF-β3; essentially as described in the Example section). The presence of cartilage tissue can be detected by RNA or protein-based methods for markers such as chondroitin sulfate proteoglycan 4 (CS4), type X collagen, and cartilage oligomeric matrix protein (COMP).

As described in the Examples section which follows, the present inventors have devised a long-term, high-density culture technique for the formation of a tendon tissue. Thus, the CTPs of the present invention were cultured in vitro at a cell density of $5$-$10 \times 10^6$ cells/cm² in the presence of a culture medium containing alpha-MEM supplemented with 15% FBS, 50 μg/ml ascorbic acid and $10^{-7}$ M dexamethasone. Cultures were kept for long periods of up to 4 months in culture, with no further splitting. As is shown in FIGS. 5a-f and is described in Example 6 of the Examples section which follows, tendon tissues formed in vitro included organized, parallel-aligned cells that express type I collagen and exhibit high matrix-to-cell ratio. Moreover, such tendon tissues exhibited mechanical properties which are similar to the native tendon tissues (Example 6).

Thus, according to yet another aspect of the present invention there is provided a method of generating a tendon tissue in vitro.

The method is effected by culturing the CTPs of the present invention in a culture medium which comprises ascorbic acid and/or dexamethason under culture conditions devoid of a carrier, thereby generating the tendon tissue.

The term "carrier" refers to any scaffold, bead, polymer or matrix which supports the attachment of cells thereto. The phrase "devoid of a carrier" as used herein refers to any culture conditions which enable the attachment of the CTPs directly to the culture vessel wall and not to a carrier (e.g., a scaffold). This is in sharp contrast to all known methods of generating tendon tissues in vitro, which are based on seeding cells-of-interest (e.g., non-genetically modified cells) onto a scaffold or a polymer suitable for tissue formation.

Preferably, the culture medium used for generating the tendon tissue comprises ascorbic acid (e.g., between 1-500 μg ml, preferably, about 50 μg/ml) and dexamethasone (e.g., between $10^{-5}$-$10^{-8}$ M, preferably, about $10^{-7}$ M).

Preferably, culturing according to the method of generating a tendon tissue of this aspect of the present invention is effected without cell passaging for culturing periods which vary between a few weeks to several months (e.g., between 4 weeks to 6 months). Preferably, the culture medium is occasionally replaced, e.g., every 2-7 days (e.g., every 4 days). It will be appreciated that the process of tendon tissue formation begins as a single cell attaching to the culture plate side wall, forming fibrous matrix with a tendon-like shape.

The presence of a functional tendon tissue can be determined using histological staining, immunological assays (e.g., using an anti-type I collagen antibody), SEM analyses, electron microscopy, and mechanical evaluation using the stress strain test, essentially as described in the Examples section which follows.

It will be appreciated that for engineering of a particular tissue-of-interest (e.g., a tendon or a ligament), the culturing period of the cells may vary (e.g., become shorter) such that following the formation of a sheet-like tissue (e.g., following 4-5 weeks), the sheet-like tissue is removed from the culture vessel (using e.g., a cell scraper) and further rolled or folded to form the engineered tissue-of-interest (e.g., tendon, ligament). It will be appreciated that due to the culturing conditions employed according to this aspect of the present invention, which result in a tissue with high matrix to cells ratio, removal of the sheet-like tissue can be easily performed while preserving the intact tissue structure.

For example, as is illustrated in FIGS. 13a-e and is described in Example 9 of the Examples section which follows, following 4-5 weeks in the high density culture the formed sheet-like tissue was removed and rolled to form a rounded cylinder. The resulting tendon tissues were cylinder-shaped constructs, with typical ultrastructure characteristics and biomechanical properties of early tendons.

It will be appreciate that tissues which are formed in vitro from the isolated CTPs of the present invention (engineered tissues) can be further implanted in a subject in need thereof (e.g., a subject in need of a CTP-derived tissue formation, regeneration and/or repair) using techniques known in the art (e.g., using a surgical tool such as a scalpel, spoon, spatula, suture device, or other surgical device) to thereby regenerate, replace and/or repair the tissue-of-interest.

For example, as is shown in FIGS. 14a-b and is described in Example 9 of the Examples section which follows, the present inventors were capable of repairing a critical Achilles-tendon injury in mice. Thus, the implanted tendon grafts were remodeled and exhibited excellent biomechanical properties. Moreover, the implanted tendon grafts were functional in vivo as evidenced by the increased ankle extension following transplantation of a tendon graft instead of the injured Achilles tendon.

While further reducing the present invention to practice, the present inventors have uncovered that the connective tissue progenitor cells obtained according to the method of this aspect of the present invention can be used for in vivo cell-based therapy.

As described in Example 7 of the Examples section which follows, when the adult tissue-derived CTPs of the present invention were implanted underneath the kidney capsule of SCID-beige mice a localized sub-capsular formation of loose connective tissue was observed. In addition, as described in Example 8 of the Examples section which follows, when the adult tissue-derived CTPs were subcutaneously transplanted into cd1 nude mice, ectopic new bone and cartilage tissues were formed. The ectopic tissues were well vascularized and biocompatible (FIGS. 11a-c) and included radio-opaque bone tissue (FIG. 4). Further histological analyses of the ectopic tissues confirmed the formation of new bone (FIGS. 12a-b) and hypertrophic cartilage (not shown) tissues.

Thus, according to yet another aspect of the present invention there is provided a method of in vivo forming or generating a connective tissue. The method is effected implanting in a subject in need therefore the connective tissue progenitor cells of the present invention; thereby in vivo forming the connective tissue.

The phrase "in vivo" refers to forming a tissue within a living organism such as a plant or an animal, preferably in mammals, preferably in human subjects.

The phrase "a subject in need thereof" as used herein refers to a mammal, preferably a human being at any age who is in need of a connective tissue such as for tissue construction, repair, regeneration or replacement. For example, such a subject can suffer from a diseased, degenerated, injured or broken tissue or may be missing a particular tissue.

Preferably, the connective tissue which can be formed in vivo according to the method of this aspect of the present invention include bone tissue, cartilage tissue and loose connective tissue.

Implanting the CTPs in the subject can be performed using methods known in the art such as by administering or injecting the CTPs with a syringe needle, catheter or cannula. The cells are preferably administered near or at the site-of-interest (e.g., bone, cartilage, connective tissue) within the subject (e.g., at the site of the damaged or injured tissue) and thus can be used to repair bone fracture, diseased or damaged cartilage, bone or connective tissue. It will be appreciated that in some cases alternative sites may be used. In addition, it will be appreciated that the cells can be administered as an isolated cell preparation (cell therapy) or can be first seeded on a scaffold and then administered to the subject (engineered tissue therapy).

The present invention further contemplates monitoring the formation, regeneration or repair of the connective tissue following implantation. For example, the formation of new bone tissue can be monitored by X-ray and/or CT analysis; the formation of a new tendon tissue can be monitored by MRI; the formation of a new connective tissue can be monitored by MRI. Alternatively, the formation of new tissue can be evaluated by physiological assays such as extension of a tendon, strength of a bone and the like.

It will be appreciated that the CTPs of the present invention can be derived from either autologous sources such as self bone marrow cells, self cord blood cells, self foreskin cell, self adipose tissue, or from allogeneic sources such as bone marrow, bone, umbilical cord, cord blood, connective tissue or other cells derived from non-autologous sources. Since non-autologous cells may induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13: 783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

The isolated cell preparation of CTPs of the present invention may also form part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the isolated cell preparation of connective tissue progenitor cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Thus, the teachings of the present invention can be used for various therapeutic applications such as tendon and ligament repair, bone regeneration, cartilage regeneration, tissue augmentation, tissue reconstruction (mediated or assisted by the CTPs of the present invention) such as deep wound healing, burn wound dressing and skin regeneration, skin fillers, orthodontic procedures, sling procedures and fascia reconstruction.

The present invention further contemplates an article-of-manufacture which comprises packaging material and a composition comprising the isolated cell preparation of CTPs of the present invention along with instructions for use in cell based therapy, tissue repair, reconstruction, regeneration and/or replacement.

The present invention further contemplates an article-of-manufacture which comprising packaging material and a tissue graft generated in vitro from the CTPs of the present invention along with instructions for using the tissue graft for tissue repair, regeneration and/or replacement.

The present invention further contemplates the use of the CTPs of the present invention for the preparation of intact ECM (non-conditioned or conditioned with certain cells such as specialized cells, e.g., cardiomyocytes, keratinocytes and the like) for specialized tissue regeneration/regeneration as well as purified ECM components for tissue regeneration, anti-aging medicine related applications.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Connective Tissue Progenitors (CTPs) Derivation and Propagation From Adult Stem Cells—

Adult stem cells derived CTPs were generated from fetal connective tissue including bone, muscle, cartilage and loose connective tissue, from termination of pregnancies from 9-16 weeks of gestation. In addition, adult stem cells derived CTPs were generated from adult tissue including foreskin (from a neonatal individual) and fat tissue (from 20-60 year old individuals) obtained via liposuction. Briefly, adipose tissue was washed with PBS solution and then subjected to 0.1-0.2% type II collagenase digestion for 1-4 hours. The stromal vascular fraction was then separated from the adipose cells by centrifugation and further purified, using plastic adherence, to remove contaminating mononuclear cell fractions. Next cells were introduced with CTP medium. For foreskin CTPs, foreskin tissue was washed with PBS solution and the tissue was cut into 2-4 mm pieces, and then subjected to 0.1-0.2% type II collagenase digestion for overnight. Next cells were introduced with CTP medium. For fetal tissue CTP, fetal tissue was washed with PBS solution and the tissue was cut into 2-4 mm pieces, and then subjected to 0.1-0.2% type II collagenase digestion for overnight. Alternatively, for fetal CTPs, the fetal tissue was cut into 2-4 mm pieces, and then directly seeded on tissue culture plates and introduced with CTP medium.

Osteogenic Differentiation and Matrix Formation—

For induction of mineralization, CTPs were grown with CTP medium supplemented with 10 mM beta-glycerophosphate (inorganic phosphate), and let to become over-confluent for period of at least 10 days before mineralization appears.

Chondrogenic Differentiation

Method I: The "Intact Layer" Method, Formerly Called "Spontaneous"—

Sub-confluent CTP cultures (from any passage, e.g., 1-13) were removed from the culture plates (without pre-collagenase treatment) as an intact layer, were placed in suspension and were fed with the CTP medium described hereinabove. This method generates typical cartilage morphology.

Method 2: The Pellet Culture System, Formally Called "Directed"—

Sub-confluent CTP cultures (from any passage) were re-suspended at a density of $2-10^5$ cells/ml (the density can vary), dispensed into 15-ml conical tubes and centrifuged for 5 minutes at 1,200 rpm to form spherical pellets. The pellets were further cultured in medium containing 1% serum in addition to high-glucose Dulbecco's modified Eagle's medium supplemented with $10^{-7}$ M dexamethasone, 50 µg/ml ascorbate-2-phosphate, 40 µg/ml L-proline, 100 µg/ml sodium pyruvate, 50 mg/ml ITS+Premix (Collaborative Biomedical: 6.25 µg/ml insulin, 6.25 µg/ml transferrin, 6.25 ng/ml selenious acid, 1.25 mg/ml bovine serum albumin, and 5.35 mg/ml linoleic acid) and 10 ng/ml TGF-β3. This method induced up-regulation of specific cartilage matrix genes such as Col-X, COMP and CS4.

RT-PCR Analysis—

Total RNA was isolated using the TRIzol Reagent (Invitrogen, Carlsbad, Calif. USA) according to the manufacturer's instructions. cDNA was reverse transcribed from 1 µg total RNA with M-MLV Reverse Transcriptase (Promega, Madison, Wis. USA). PCR conditions were optimized for each set of primers and the number of PCR cycles was confirmed to be in the linear range of amplification. The amplified products were separated on 2% agarose gel stained with ethidium bromide and identified by size. The identity of each product was confirmed by restriction enzyme digestion. Samples not treated with reverse transcriptase and no-template samples were used as controls. Table 1, hereinbelow, summarizes the primer sequences (along with their SEQ ID NOs.), annealing temperatures, cycle numbers used for RT-PCR, the restriction enzyme used to verify the identity of RT-PCR products (along with the expected size of the digested product).

TABLE 1

RT-PCR primers and conditions

| Gene (GenBank Accession No.) | Forward (F) and Reverse (R) primers (SEQ ID NO: ) 5'→3' | Cyc. | Ann. | Restr. Enzyme | RT-PCR product size |
|---|---|---|---|---|---|
| CBFA1 (NM_004348) | CBFA1 F: CCGCACGACAACCGCACCAT (SEQ ID NO: 1) CBFA1 R: CGCTCCGGCCCACAAATCTC (SEQ ID NO: 2) | 40 | 62° C. 30 sec | SacI 215 bp | 283 bp |
| SOX9 NM 000346 | Sox9 F: ATCTGAAGAAGGAGAGCGAG (SEQ ID NO: 3) Sox9 R: TCAGAAGTCTCCAGAGCTTG (SEQ ID NO: 4) | 35 | 58° C. 30 sec | EcoRII | 264 bp |
| COL1 NM 000089.3 | hCOL1 F: GCACACAATGGATTGCAAGG (SEQ ID NO: 5) hCOL1 R: TAACCACTGCTCCACTCTGG (SEQ ID NO: 6) | 35 | 64° C. 30 sec | NcoI 39 bp BclI 45 bp | 476 bp |
| ONEC NM 003118 | Onec F: GCAGCAATGACAACAAGACC (SEQ ID NO: 7) Onec R: CTTCTCATTCTCATGGATCTTC (SEQ ID NO: 8) | 35 | 58° C. 30 sec | SphI 166 bp | 277 bp |

TABLE 1-continued

RT-PCR primers and conditions

| Gene (GenBank Accession No.) | Forward (F) and Reverse (R) primers (SEQ ID NO: ) 5'→3' | Cyc. | Ann. | Restr. Enzyme | RT-PCR product size |
|---|---|---|---|---|---|
| OPN NM_000582.21 | hOPN F: CTAGGCATCACCTGTGCCATACC (SEQ ID NO: 9) hOPN R: CAGTGACCAGTTCATCAGATTCATC (SEQ ID NO: 10) | 30 | 55° C. 45 sec | EcoRII 226 bp | 330 bp |
| ALP NM 000478 | ALP F: TGGAGCTTCAGAAGCTCAAC (SEQ ID NO: 11) ALP R: ATCTCGTTGTCTGAGTAGTACCAGTCC (SEQ ID NO: 12) | 35 | 62° C. 30 sec | BstXI 120 bp | 435 bp |
| Hpth/r1 NM 000316 | hPTH/R F: CACAGCCTCATCTTCATGG (SEQ ID NO: 13) hPTH/R1 R: GCATCTCATAGTGCATCTGG (SEQ ID NO: 14) | 35 | 60° C. 45 sec | SacI 148 bp | 417 bp |
| COL9 α2 (17/11) NM_001852.31 | Col9/2 F: TGGTTTAACTGGAGCCAAGG (SEQ ID NO: 15) Col9/2 R: GCCCACCATGAATTTATATC (SEQ ID NO: 16) | 35 | 60° C. 30 sec | SphI 330 bp | 520 bp |
| COL10 NM 000493 | COL10 F: CCCTTTTTGCTGCTAGTATCC (SEQ ID NO: 17) COL10 R: CTGTTGTCCAGGTTTTCCTGGCAC (SEQ ID NO: 18) | 40 | 60° C. 30 sec | XhoI 194 bp | 468 bp |
| COMP (NM_000095) | COMP F: CAGGACGACTTTGATGCAGA (SEQ ID NO: 19) COMP R: AAGCTGGAGCTGTCCTGGTA (SEQ ID NO: 20) | 35 | 57.5° C. 30 sec | BstXI 141 bp | 314 bp |
| AGGRECAN NM 001135 | AGN F: ATCCGAGACACCAACGAGAC (SEQ ID NO: 21) AGN R: GGCTTCACCCTCACTGATGT (SEQ ID NO: 22) | 35 | 60° C. 30 sec | SphI 290 bp | 477 bp |
| CS4 NM 001897 | CS-4S F: CCCCCATCCTCACTACAAAC (SEQ ID NO: 23) CS-4S R: ATCCAGGGTTCCTCTGTGTG (SEQ ID NO: 24) | 40 | 60° C. 30 sec | PstI 34-38 bp | 242 bp |
| SCLER BK000280.11 | Scler F: TGCAAGCTTCCCTTTTCAGT (SEQ ID NO: 25) Scler R: CTGCACAGCCGAAATTGTAA (SEQ ID NO: 26) | 40 | 60° C. 30 sec | HgaI 292 bp | 455 bp |
| COL3 NM_000090.21 | Col3 F: CCTCCAACTGCTCCTACTCG (SEQ ID NO: 27) Col3 R: CGGGTCTACCTGATTCTCCA (SEQ ID NO: 28) | 35 | 60° C. 30 sec | BglI 266 bp | 439 bp |
| collagen, type XII NM_004370 | Col-XII F: GTGCCTGGACTGATTTGGTT (SEQ ID NO: 29) Col-XII R: TGTGGAGGCAATTTGTTTGA (SEQ ID NO: 30) | 35 | 60° C. 30 sec | ScaI 185 bp StyI 414 bp | 464 bp |
| DECOR NM_001920.31 | Decor F: TGAAGAACCTTCACGCATTG (SEQ ID NO: 31) Decor R: GAGCCATTGTCAACAGCAGA (SEQ ID NO: 32) | 35 | 60° C. 30 sec | SacI 255 bp | 481 bp |
| BIGLY NM_001711.31 | Bigly F: TGCAGAACAACGACATCTCC (SEQ ID NO: 33) Bigly R: CCAGGTTCAAAGCCACTGTT (SEQ ID NO: 34) | 35 | 60° C. 30 sec | BstXI 192 bp | 319 bp |

TABLE 1-continued

RT-PCR primers and conditions

| Gene (GenBank Accession No.) | Forward (F) and Reverse (R) primers (SEQ ID NO: ) 5'→3' | Cyc. | Ann. | Restr. Enzyme | RT-PCR product size |
|---|---|---|---|---|---|
| ELAST NM_000501.11 | Elast F: GCTATGGACTGCCCTACACC (SEQ ID NO: 35) Elast R: AGCTCCTGGGACACCAACTA (SEQ ID NO: 36) | 40 | 60° C. 30 sec | BglI 288 + 329 bp | 371 bp |
| FIBRO NM 212482 | Fibro F: GGAGTCAGCTGCCAAGAGAC (SEQ ID NO: 37) Fibro R: ACACACGTGCACCTCATCAT (SEQ ID NO: 38) | 35 | 60° C. 30 sec | XhoI 215 bp | 482 bp |
| TEN C NM 002160 | Ten F: CGTGGAGTACCTTGTCAGCA (SEQ ID NO: 39) Ten R: AGGTAACCGGTGACTGATGC (SEQ ID NO: 40) | 35 | 60° C. 30 sec | XhoI 252 bp | 438 bp |

Primers used to amplify RT-PCR products of the noted genes (are referred to using GenBank Accession Nos.) are provided along with the PCR annealing (Ann.) conditions, number of PCR cycles (Cyc.), the size of PCR products and the restriction enzyme (Restr. Enzyme) and digestion product used to verify the identity of the RT-PCR product.

Microarray Analysis—

For cDNA microarray analysis, isolated total RNA from undifferentiated hESCs (H9.2), fetal CTPs (passage 1) and hESC-derived CTPs grown in the presence of the CTP medium (passages 1 and 9) were reverse transcribed with M-MLV Reverse Transcriptase (Promega, Madison, Wis. USA) using Biotin-16-dUTP (Roche, Mannheim, Germany). The array membranes (GEArray Q Series Human Osteogenesis Gene Array HS-026, SuperArray Bioscience Corp., Frederic, Md. USA) were pre-hybridized for 2 hours with heat-denatured salmon sperm DNA (Invitrogen) at a final concentration of 100 µg/ml according to the manufacturer's instructions. The membranes were hybridized overnight with Biotin-16-dUTP-labeled cDNA probes, and then washed twice for 15 minutes each in a solution of 2×SSC, 1% SDS followed by two washes of 15 minutes each in a solution of 0.1×SSC, 0.5% SDS. All steps were performed at 60° C. with continuous agitation. Chemiluminescent detection was performed using the Chemiluminescent Detection Kit (SuperArray Bioscience Corp., Frederic, Md. USA) according to the manufacturer's instructions. The membranes were blocked for 40 minutes with a GEAblocking solution Q. Binding of alkaline phosphatase-conjugated streptavidin was performed by incubating the membranes for 10 minutes in a binding buffer. The membranes were then washed four times, for 5 minutes each, with 1× Buffer F and rinsed twice with Buffer G, followed by incubation of 2-5 minutes with CDP-star chemiluminescent substrate. All steps were performed at room temperature with continuous agitation. The signal was detected using X-ray film.

Karyotype Analysis—

For karyotype analyses, standard G banding was performed on adult stem cells derived-CTPs (from fetal tissue, CTPs were from passage 8-10, from fat tissue, CTPs were from passage 14) essentially as described elsewhere (Amit, M. et al, 2000).

Electron Microscopy—

For transmission electron microscopy (TEM) cells were fixed in 3% glutaraldehyde in 0.1 M sodium cacodylate buffer pH=7.4, post-fixed with 1% $OsO_4$ and in 2% uranyl acetate, gradually dehydrated in ethanol series and embedded in Epon 812. Ultrathin sections (70 to 90 nm) cut on an ultramicrotome (Leica UCT) were mounted on grids, stained with lead-citrate, and then examined with a Tecnai 12 transmission electron microscope under 120 kV. Pictures were digitized with CCD Megaview III and analyzed with analySIS software (Soft Imaging System).

Scanning Electron Microscopy (SEM)—

For SEM, cells and cell-seeded scaffolds were fixed in 3% glutaraldehyde in 0.1 M sodium cacodylate buffer pH=7.4, followed by gradual dehydration in ethanol and drying using hexamethyldisilazane (HMDS) (Sigma). Samples were sputter coated with carbon and viewed under LEO field-emission scanning electron microscope for imaging and energy dispersive spectroscopy (EDS) analysis.

Cytochemistry and Electron Microscopy—

For histological analyses, cells were fixed in 10% natural buffered formalin, gradually dehydrated in ethanol and embedded in paraffin. Sections were stained with Hematoxylin and Eosin (H&E) for general histomorphology. Picrosirius red (Gurr-BDH, England) was used for the detection of matrix collagens, and Toluidine blue (Serva, Germany) was used to detect matrix proteogylcans in chondrogenic cultures (Hyllested, J. L, et al 2005). Alizarin Red (Sigma) was used to detect calcium phosphate deposits on culture plates as evidence for bone mineralization. For immunofluorescence studies, cells were fixed in 4% paraformaldehyde in phosphate-buffered saline (PBS), and stained with the following primary antibodies, diluted in primary antibody diluent (Dako): anti-human type I collagen (Chemicon, Intnl, Inc. Temecula, Calif., USA, cat. No. MAB3391), anti-human alkaline phosphatase (R&D, Systems Inc, Minneapolis, Minn., USA, Cat. No. MAB1448) and anti-human type II collagen (Chemicon, Cat. No. MAB8887). DAPI was used for nuclear counterstaining. Appropriate secondary antibodies were used for visualization.

FACS Analysis—

Cells were removed from the culture dish with type IV collagenase (Wortington) (0.1%, 30-60 minutes at 37° C.) followed by Trypsin/EDTA (Sigma) for 5 minutes at 37° C. and re-suspended in a FACS buffer [Sigma, PBS supplemented with 2% fetal bovine serum (Gibco) and containing 0.05% NaN3]. Fc blocking was performed by addition of 4% Human serum (Sigma). Cells were probed for 30 minutes at room temperature with the specific monoclonal antibodies (Pharmingen; eBioscience; DAKO) or an appropriate isotype control antibodies (Pharmingen; eBioscience; DAKO) in FACS buffer. Cell were washed twice in FACS buffer, and analyzed using a FACSAria flow cytometer (Becton Dickinson). Acquisition was set for 10,000 events per sample. Dead cells were excluded from analysis by staining with 7AAD (eBioscience). Data were analyzed with Diva software (Becton Dickinson). Experiments were performed in duplicates.

Scaffold Fabrication and Cell Seeding—

Electrospun nanofiber scaffolds were made of a 1:1 blend of polycaprolactone (PCL) and poly (lactic acids) (PLA) by a process previously described (Ma, Z. et al 2005). The average thickness of the prepared scaffold was 500 µm, fiber diameter ranged between 200-450 nm, with porosity of 85%. For preparation for cell seeding, scaffold mat was cut into 0.5×0.5 $cm^2$ squares, gas-sterilized with ethylene oxide, immersed in 5 M sodium hydroxide and washed in PBS to increase surface hydrophilicity. For seeding the cells on scaffolds, subconfluent CTP cultures were collagenase-treated, trypsinized and counted. $5 \times 10^5$ cells were resuspended in 10 µl of CTP medium, seeded onto each scaffold and allowed to attach for 30 minutes before fresh medium was added. Cultures were maintained for one month before harvesting for analysis. Plain cultures on plastic plates were used as control.

In-Vitro Engineering of Functional Tendons—

Tendons were spontaneously formed upon applying the new long-term high-density culture technique: subconfluent CTP cultures (passages 2-21) were regularly split and counted before seeding at a high density of $5-10 \times 10^6$ cells/$cm^2$ on tissue culture plates in the presence of CTP medium. Cultures were kept for long periods of up to 4 months in culture, with no further splitting.

Mechanical Testing of In Vitro Engineered (Formed) Tendon Grafts—

Engineered constructs were removed from their culture plates immediately before testing. The construct diameter was measured at several positions along the length, using an optical microscope (Olympus BX 60 ×500 magnification). An average diameter was calculated, using measured values. Tensile testing was performed with a Micro Fiber Tensile Machine, outfitted with a 35 N load cell and a special stainless steel grips. The grips clamped the specimens by jaws machined from Delrin (acetal). The control of machine was performed by developed software on Matlab6 and data acquisition performed with National Instruments hardware on a PentiumII PC. The load cell was zeroed after the attachment of each sample. Samples were moistened by regularly applying drops of PBS. The gauge length was taken to be the length of the construct between the grips, which was measured from the calibrated images of a fast MotionScope CCD camera. Tests were conducted at a constant displacement rate of 0.08 mm/sec.

In-vVivo Studies—

For subcutaneous transplantation (ectopic transplantation), cd1 nude mice were anesthetized and approximately 5 mm long incision was made in 2 or 3 locations on the back of the animal. CTPs from fat (from passage 12-14) and fetal (from passages 5-6 and 10-11) tissues were implanted into the subcutaneous pouch. The method for critical Achilles tendon injury model preparation is described in the description of FIGS. 13a-e. All animal experimental protocols were approved by the Animal Use and Care Committee of the Technion Faculty of Medicine.

In Vivo Transplantation of CTPs Underneath Kidney Capsules—

Subconfluent CTP cultures (from fetal derived CTPs, passages 5-6 and 10-11) were scraped off the culture plates, washed with PBS and implanted underneath the kidney capsule of 5-week-old CB-17 SCID-beige mice (n=6). Six and twelve weeks after transplantation, kidneys were retrieved, fixed in 10% buffered formalin, embedded in paraffin, and sectioned for histological examination.

Example 1

Isolation of Connective Tissue Progenitor Cells From Human Adult Stem Cells

A cell source for tissue engineering should be highly proliferative while phenotypically stable in vitro, providing a sufficient amount of cells. As estimated elsewhere (Muschler, G. F. et al, 2002), approximately $7 \times 10^7$ osteoblasts are needed to form one cubic centimeter of a new bone. While reducing the present invention to practice, the present inventors have uncovered, through laborious experimentations, culturing conditions suitable for the isolation, propagation and differentiation of connective tissue progenitor cells derived from adult stem cells, as follows.

Experimental Results

Isolation of Connective Tissue Progenitor Cells (CTPs) From Adult Stem Cells—

Adult stem cells from fat, foreskin or fetal tissue were dissociated with a combination of enzymatic digestion and aggressive mechanical agitation. The derived cells were cultured in the presence of a CTP medium containing ascorbic acid and dexamethasone, factors known to promote osteoblastic differentiation (Maniatopoulos, C., et al, 1988; Coelho, M. J. et al, 2000). The cells were cultured without splitting (passaging) in the presence of the CTP medium until reaching sub-confluency (between about 5-10 days) and were then subjected to serial passaging using type IV collagenase (0.1%, 30-60 minutes at 37° C.) followed by trypsinization (0.25%, 2-5 minutes at 37° C.). The growth kinetic pattern of the cells, which were continuously expanding without obvious senescence up to 25 passages, suggested the derivation of a putative cell line. At passage 25 the growth rate of the cells was slowed down (data not shown) and the cells tended to form mineralized cultures at a higher frequency (data not shown). Cultures recovered well after freeze/thaw cycles, and showed the same proliferation and differentiation potential as prior to the freeze/thaw cycles. In addition, adult stem cell derived CTPs from early passages exhibit a morphology resembling that of mesenchymal stem cells (MSCs, FIGS. 3a-b) and CTPs from later passages exhibit a morphology resembling that of fibroblasts (FIG. 3c).

CTPs Exhibit Clonogenic Potential and Normal Karyotype—

The clonality potential of the fetal derived CTP cells was assessed by seeding single cells each in different culture wells. Colonies were formed in high efficiency (20-22 out of 24 experiments (data not shown) and were identical in their growth kinetics, morphology and phenotype, as assessed by RT-PCR. Additionally, G banding analysis of fat stem cells derived CTP nuclei obtained from passages 5-6 and from fetal derived CTPs from passages 7-8, 14 and 20 confirmed that the CTPs are karyotypically normal (data not shown).

CTPs are Suitable for Cell-Based Tissue Engineering—

Assuming symmetric cell division, at least $3.5 \times 10^9$ connective tissue progenitor cells are obtained from a single cell of the adult stem cells following about 20 passage. Thus, the unique derivation method of the present invention generates a sufficient amount of cells for cell-based tissue engineering application.

Altogether, the present inventors have demonstrated that the CTP cells isolated from adult stem cells by culturing and passaging in the CTP medium exhibit high proliferative capacity (for at least 20 passages), in vitro stability (with normal karyotype) and clonogenic potential. In addition, the present inventors have uncovered that the CTPs of the present invention are suitable for cell-based tissue engineering.

Example 2

CTPs Express Markers of Mesenchymal and Osteoblast-Like Cells

To test the potential of the adult stem cells derived CTPs of the present invention to differentiate into the osteogenic lineage, the expression profile of the CTP cells of the present invention was assessed by RT-PCR, cDNA microarray and FACS analyses, as follows.

Experimental Results

CTPs Express Osteogenic Markers—

Gene expression of CTP cells grown in the presence of the CTP medium from passages 1 and 10, was assessed by RT-PCR analysis. As is shown in FIGS. 2a-u, CTPs stably express core binding factor alpha 1 (CBFA1), and SOX9, both are early transcription factors known to play a major role in osteoblast and chondrocyte differentiation. Type I collagen, the most abundant extracellular protein which is synthesized by osteoblasts, osteonectin and osteopontin, two major non-collagenous bone matrix proteins, parathyroid hormone receptor 1 (PTHR1), which regulates mineral homeostasis and bone formation, and bone-specific alkaline phosphatase, which binds phosphor to calcium and forms bone hydroxyapetite, were all detected in the CTPs, indicating osteogenic potential.

Immunofluorescence analysis of the adult stem cells derived CTPs demonstrated that the fetal-derived CTPs of the present invention express alkaline phosphatase (ALP, FIG. 7a) and osteocalcin (FIG. 7b), markers of the osteogenic lineage.

Expression Profiles of CTP-Derived Osteogenic-Like Cells—

The gene expression profile of the cells was detected using cDNA microarray analysis using a set of approximately 100 osteogenesis-related genes. The common transcripts were compared between hESC-derived CTPs (passage 1 and 9) to human fetal CTPs (passage 1). Two independent experiments were performed. The complete list of positive transcripts is shown in Table 2, hereinbelow. Forty transcripts were found to be shared among hESC-derived CTPs and human fetal CTPs, including growth factors and associate molecules, cell adhesion molecules, and matrix associated proteins. A significant overlap of 36 transcripts shared by the three populations (i.e., undifferentiated hESCs, hESC-derived CTPs and human fetal CTPs) was observed. This set of shared transcripts represent genes that though known to play a significant role in osteogenesis, are already switched-on at the hESC stage.

TABLE 2

Expression profile of fetal stem cells-derived CTPs in comparison to undifferentiated hESCs and hESCs-derived CTPs (p9)

| Symbol | Gene Name | Undiff- hESCs | CTP, p9 | Fetal | Description |
|---|---|---|---|---|---|
| ALPL | AP-TNAP/HOPS | p | p | n | Alkaline phosphatase, liver/bone/kidney |
| ANXA5 | ANX5/ENX2 | p | p | p | Annexin A5 |
| ARSE | CDPX/CDPX1 | n | n | n | Arylsulfatase E (chondrodysplasia punctata 1) |
| BGLAP | BGP | n | n | n | Bone gamma-carboxyglutamate (gla) protein (osteocalcin) |
| BGN | DSPG1/PG-S1 | p | p | p | Biglycan |
| BMP1 | PCOLC/TLD | n | p | n | Bone morphogenetic protein 1 |
| BMP2 | BMP2A | p | p | n | Bone morphogenetic protein 2 |
| BMP3 | BMP3 | p | p | n | Bone morphogenetic protein 3 (osteogenic) |
| BMP4 | BMP2B/BMP2B1 | n | n | n | Bone morphogenetic protein 4 |
| BMP5 | MGC34244 | p | p | p | Bone morphogenetic protein 5 |
| BMP6 | VGR/VGR1 | n | n | n | Bone morphogenetic protein 6 |
| BMP7 | OP-1 | p | p | p | Bone morphogenetic protein 7 (osteogenic protein 1) |
| BMP8B | BMP8/OP2 | p | p | p | Bone morphogenetic protein 8b (osteogenic protein 2) |
| BMPR1A | ACVRLK3/ALK3 | p | p | p | Bone morphogenetic protein receptor, type IA |
| CASR | FHH/FIH | n | n | n | Calcium-sensing receptor (hypocalciuric hypercalcemia 1, severe neonatal hyperparathyroidism) |
| CD36 | FAT/GP3B | n | n | n | CD36 antigen (collagen type I receptor, |

TABLE 2-continued

Expression profile of fetal stem cells-derived CTPs in comparison to undifferentiated hESCs and hESCs-derived CTPs (p9)

| Symbol | Gene Name | Undiff- hESCs | CTP, p9 | Fetal | Description |
|---|---|---|---|---|---|
| SCARB1 | CD36L1/CLA-1 | p | p | p | thrombospondin receptor) Scavenger receptor class B, member 1 |
| CSIG | L12/PBK1 | n | n | n | Ribosomal L1 domain containing 1 |
| COL10A1 | COL10A1 | p | p | n | Collagen, type X, alpha 1(Schmid metaphyseal chondrodysplasia) |
| COL11A1 | CO11A1/COLL6 | n | p | p | Collagen, type XI, alpha 1 |
| COL12A1 | COL12A1L/TYPE XII | n | p | p | Collagen, type XII, alpha 1 |
| COL14A1 | UND | p | p | n | Collagen, type XIV, alpha 1 (undulin) |
| COL15A1 | COL15A1 | n | n | n | Collagen, type XV, alpha 1 |
| COL16A1 | 447AA/FP1572 | p | p | p | Collagen, type XVI, alpha 1 |
| COL17A1 | BP180/BPAG2 | n | p | n | Collagen, type XVII, alpha 1 |
| COL18A1 | KNO | p | p | p | Collagen, type XVIII, alpha 1 |
| COL19A1 | COL9A1L/D6S228E | n | n | n | Collagen, type XIX, alpha 1 |
| COL1A1 | AA 694-711/OI4 | n | n | n | Collagen, type I, alpha 1 |
| COL2A1 | COL11A3/SEDC | p | p | p | Collagen, type II, alpha 1 (primary osteoarthritis, spondyloepiphyseal dysplasia, congenital) |
| COL3A1 | EDS4A | p | p | p | Collagen, type III, alpha 1 (Ehlers-Danlos syndrome type IV, autosomal dominant) |
| COL4A3 | TUMSTATIN | n | n | n | Collagen, type IV, alpha 3 (Goodpasture antigen) |
| COL4A4 | CA44 | p | p | p | Collagen, type IV, alpha 4 |
| COL4A5 | ASLN/ATS | n | n | n | Collagen, type IV, alpha 5 (Alport syndrome) |
| COL5A1 | COL5A1 | p | p | p | Collagen, type V, alpha 1 |
| COL7A1 | EBD1/EBDCT | n | p | n | Collagen, type VII, alpha 1 (epidermolysis bullosa, dystrophic, dominant and recessive) |
| COL9A2 | EDM2/MED | p | p | p | Collagen, type IX, alpha 2 |
| CSF2 | GMCSF | p | n | n | Colony stimulating factor 2 (granulocyte-macrophage) |
| CSF3 | G-CSF/GCSF | n | n | n | Colony stimulating factor 3 (granulocyte) |
| CTSK | CTS02/CTSO | n | n | p | Cathepsin K (pycnodysostosis) |
| DCN | DSPG2/PG40 | p | p | p | Decorin |
| EGF | URG | n | n | n | Epidermal growth factor (beta-urogastrone) |
| EGFR | ERBB/ERBB1 | p | p | n | Epidermal growth factor receptor (erythroblastic leukemia viral (v-erb-b) oncogene homolog, avian) |
| FGF1 | AFGF/ECGF | n | p | n | Fibroblast growth factor 1 (acidic) |
| FGF2 | BFGF/FGFB | p | p | n | Fibroblast growth factor 2 (basic) |
| FGF3 | HBGF-3/INT2 | n | n | n | Fibroblast growth factor 3 (murine |

TABLE 2-continued

Expression profile of fetal stem cells-derived CTPs in comparison to undifferentiated hESCs and hESCs-derived CTPs (p9)

| Symbol | Gene Name | Undiff-hESCs | CTP, p9 | Fetal | Description |
|---|---|---|---|---|---|
| | | | | | mammary tumor virus integration site (v-int-2) oncogene homolog) |
| FGFR1 | BFGFR/C-FGR | p | p | p | Fibroblast growth factor receptor 1 (fms-related tyrosine kinase 2, Pfeiffer syndrome) |
| FGFR2 | BEK/BFR-1 | p | n | n | Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| FGFR3 | ACH/CEK2 | p | n | n | Fibroblast growth factor receptor 3 (achondroplasia, thanatophoric dwarfism) |
| FLT1 | FLT/VEGFR1 | p | n | n | Fms-related tyrosine kinase 1 (vascular endothelial growth factor/vascular permeability factor receptor) |
| FN1 | CIG/FINC | p | p | p | Fibronectin 1 |
| GDF10 | BMP-3B/BMP3B | p | p | n | Growth differentiation factor 10 |
| 1CAM1 | BB2/CD54 | n | p | n | Intercellular adhesion molecule 1 (CD54), human rhinovirus receptor |
| IGF1 | IGFI | n | p | p | Insulin-like growth factor 1 (somatomedin C) |
| IGF1R | JTK13 | p | p | n | Insulin-like growth factor 1 receptor |
| IGF2 | IGF-II | n | n | n | Insulin-like growth factor 2 (somatomedin A) |
| ITGA1 | CD49a | p | p | p | Integrin, alpha 1 |
| ITGA2 | BR/CD49B | n | n | n | Integrin, alpha 2 (CD49B, alpha 2 subunit of VLA-2 receptor) |
| ITGA3 | CD49C/GAP-B3 | p | p | n | Integrin, alpha 3 (antigen CD49C, alpha 3 subunit of VLA-3 receptor) |
| ITGAM | CD11B/CR3A | n | n | n | Integrin, alpha M (complement component receptor 3, alpha; also known as CD11b (p170), macrophage antigen alpha polypeptide) |
| ITGAV | CD51/MSK8 | p | p | p | Integrin, alpha V (vitronectin receptor, alpha polypeptide, antigen CD51) |
| ITGB1 | CD29/FNRB | p | p | p | Integrin, beta 1 (fibronectin receptor, beta polypeptide, antigen CD29 includes MDF2, MSK12) |
| SMAD1 | BSP1/JV4-1 | p | p | p | SMAD, mothers against DPP homolog 1 (*Drosophila*) |

TABLE 2-continued

Expression profile of fetal stem cells-derived CTPs in comparison to undifferentiated hESCs and hESCs-derived CTPs (p9)

| Symbol | Gene Name | Undiff- hESCs | CTP, p9 | Fetal | Description |
|---|---|---|---|---|---|
| SMAD2 | MADH2/HSMAD2 | p | p | p | SMAD, mothers against DPP homolog 2 (*Drosophila*) |
| SMAD3 | HSPC193/HST17436 | p | p | n | SMAD, mothers against DPP homolog 3 (*Drosophila*) |
| SMAD4 | DPC4/JIP | p | p | p | SMAD, mothers against DPP homolog 4 (*Drosophila*) |
| SMAD5 | DWFC/JV5-1 | p | p | p | SMAD, mothers against DPP homolog 5 (*Drosophila*) |
| SMAD6 | HST17432/MAD | p | p | n | SMAD, mothers against DPP homolog 6 (*Drosophila*) |
| SMAD7 | MAD/MADH7 | p | p | n | SMAD, mothers against DPP homolog 7 (*Drosophila*) |
| SMAD9 | MAD/MADH6 | p | p | p | SMAD, mothers against DPP homolog 9 (*Drosophila*) |
| MMP10 | SL-2/STMY2 | n | n | n | Matrix metalloproteinase 10 (stromelysin 2) |
| MMP13 | CLG3 | p | p | p | Matrix metalloproteinase 13 (collagenase 3) |
| MMP2 | CLG4/CLG4A | p | p | p | Matrix metalloproteinase 2 (gelatinase A, 72 kDa gelatinase, 72 kDa type IV collagenase) |
| MMP8 | CLG1/HNC | n | n | p | Matrix metalloproteinase 8 (neutrophil collagenase) |
| MMP9 | GELB/CLG4B | n | n | p | Matrix metalloproteinase 9 (gelatinase B, 92 kDa gelatinase, 92 kDa type IV collagenase) |
| MSX1 | HOX7/HYD1 | p | n | n | Msh homeo box homolog 1 (*Drosophila*) |
| MSX2 | CRS2/FPP | n | n | n | Msh homeo box homolog 2 (*Drosophila*) |
| NFKB1 | EBP-1/KBF1 | n | p | p | Nuclear factor of kappa light polypeptide gene enhancer in B-cells 1 (p105) |
| PDGFA | PDGF-A/PDGF1 | p | p | n | Platelet-derived growth factor alpha polypeptide |
| RUNX2 | CCD/AML3 | p | p | p | Runt-related transcription factor 2 |
| SERPINH1 | ASTP3/CBP1 | p | p | p | Serine (or cysteine) proteinase inhibitor, clade H (heat shock protein 47), member 1, (collagen binding protein 1) |
| SERPINH1 | ASTP3/CBP1 | p | p | p | Serine (or cysteine) proteinase inhibitor, clade H (heat shock protein 47), member 1, (collagen binding protein 1) |
| SOX9 | CMD1/CMPD1 | n | n | n | SRY (sex determining region Y)-box 9 (campomelic dysplasia, autosomal sex-reversal) |

TABLE 2-continued

Expression profile of fetal stem cells-derived CTPs in comparison
to undifferentiated hESCs and hESCs-derived CTPs (p9)

| Symbol | Gene Name | Undiff-hESCs | CTP, p9 | Fetal | Description |
|---|---|---|---|---|---|
| SPARC | ON | p | p | p | Secreted protein, acidic, cysteine-rich (osteonectin) |
| SPP1 | BNSP/BSPI | p | n | n | Secreted phosphoprotein 1 (osteopontin, bone sialoprotein I, early T-lymphocyte activation 1) |
| TGFB1 | BETA 1/CED | n | p | n | Transforming growth factor, beta 1 (Camurati-Engelmann disease) |
| TGFB2 | TGF b2 | n | p | n | Transforming growth factor, beta 2 |
| TGFB3 | TGF b3 | p | p | p | Transforming growth factor, beta 3 |
| TGFBR1 | ACVRLK4/ALK-5 | p | p | p | Transforming growth factor, beta receptor I (activin A receptor type II-like kinase, 53 kDa) |
| TGFBR2 | HNPCC6/MFS2 | n | p | n | Transforming growth factor, beta receptor II (70/80 kDa) |
| TNF | DIF/TNF-ALPHA | p | p | p | Tumor necrosis factor (TNF superfamily, member 2) |
| TWIST1 | ACS3/BPES2 | p | p | n | Twist homolog 1 (acrocephalosyndactyly 3; Saethre-Chotzen syndrome) (*Drosophila*) |
| VCAM1 | INCAM-100 | n | n | n | Vascular cell adhesion molecule 1 |
| VDR | NR1I1 | n | n | n | Vitamin D (1,25-dihydroxyvitamin D3) receptor |
| VEGF | VEGFA | p | p | p | Vascular endothelial growth factor |
| VEGFB | VEGFL/VRF | n | n | n | Vascular endothelial growth factor B |
| VEGFC | FLT4-L/VRP | p | p | p | Vascular endothelial growth factor C |
| PUC18 | pUC18 | n | n | n | PUC18 Plasmid DNA |
| PUC18 | pUC18 | n | n | n | PUC18 Plasmid DNA |
| PUC18 | pUC18 | n | n | n | PUC18 Plasmid DNA |
|  |  | n | n | n |  |
|  |  | n | n | n |  |
|  |  | n | n | n |  |
| GAPDH | G3PD/GAPD | p | p | p | Glyceraldehyde-3-phosphate dehydrogenase |
| GAPDH | G3PD/GAPD | p | p | p | Glyceraldehyde-3-phosphate dehydrogenase |
| PPIA | CYPA/CYPH | p | p | p | Peptidylprolyl isomerase A (cyclophilin A) |
| PPIA | CYPA/CYPH | p | p | p | Peptidylprolyl isomerase A (cyclophilin A) |
| PPIA | CYPA/CYPH | p | p | p | Peptidylprolyl isomerase A (cyclophilin A) |
| PPIA | CYPA/CYPH | p | p | p | Peptidylprolyl isomerase A (cyclophilin A) |
| RPL13A | RPL13A | p | p | p | Ribosomal protein L13a |
| RPL13A | RPL13A | p | p | p | Ribosomal protein L13a |

TABLE 2-continued

Expression profile of fetal stem cells-derived CTPs in comparison to undifferentiated hESCs and hESCs-derived CTPs (p9)

| Symbol | Gene Name | Undiff- hESCs | CTP, p9 | Fetal | Description |
|--------|-----------|---------------|---------|-------|-------------|
| ACTB | b-Actin | p | p | p | Actin, beta |
| ACTB | b-Actin | p | p | p | Actin, beta |

Table 2: The cDNA array membrane (GEArray Q Series Human Osteogenesis Gene Array HS-026; SuperArray Bioscience Corp., Frederic, MD USA) was hybridized with biotin-labeled cDNA prepared from human fetal CTPs (fetal, passage 1), undifferentiated hESCs (H9.2; undiff-hESCs), and hESC-derived CTPs at passage 1 (p1) or passage 9 (p9). The presence (positive, "p") or absence (negative, "n") of each of the genes in the array is indicated.

Adult Stem Cells—Derived CTPs are CD105/CD166/CD44/CD29/HLA-ABC-Positive and CD45/HLA-DR-Negative—

FACS analyses performed on adult stem cells derived CTPs from passage 16 using antibodies specific to the CD105, CD166, CD44, CD29, CD45, HLA-ABC and HLA-DR surface markers demonstrated relatively high level of population purity with surface markers characteristic of MSCs (FIGS. 1a-g). Thus, the CTPs of the present invention were positive for CD105, CD166, CD44, CD29 and HLA-ABC, while negative for CD45, a hematopoietic marker and HLA-DR.

Altogether, the FACS results demonstrate that adult stem cells-derived CTPs express markers of mesenchymal stem cells (MSCs). The cDNA microarray and the RT-PCR analyses demonstrate the presence of specific markers of connective tissue derivatives including osteogenic lineage, chondrogenic lineage, tendons and ligaments. In addition, immunostaining analyses demonstrated that the CTP cells isolated according to the teachings of the present invention express markers of the osteogenic lineage and thus can differentiate to form osteoblasts and bone tissue.

Example 3

CTPs are Capable of Producing Bone Matrix

To test to capacity of the CTPs of the present invention (from fetal tissue, foreskin tissue and fat tissue) to differentiate into the osteogenic lineage and form mineralized matrix, inorganic phosphate was added to the CTP medium and the CTP cell cultures were assessed for the presence of mineralized matrix, as follows.

CTP Cells Produce Mineralized Matrix—

To test the capacity of the CTP cells of the present invention to form mineralized matrix, inorganic phosphate (beta-glycerophosphate) was added to the CTP medium. Briefly, CTPs from any passage of passages 1-25 were grown in a CTP medium supplemented with 10 mM beta-glycerophosphate and the potential of matrix formation was assessed. As is shown in FIG. 8a, enhanced mineralization which was visible macroscopically (e.g., at passage 11), or was induced at different passages if cells were grown until over-confluent. Mineralization was confirmed by Alizarin Red staining (FIG. 8b), and scanning electron microscopy (FIG. 8d) coupled with EDS spectra analysis of the bone mineralization. The EDS analysis detected calcium and phosphate as the most prominent signals, in addition to carbon and oxygen which could correspond to the presence of proteins. The ratio between the calcium and phosphate corresponds to the expected ratio of the hydroxyapatite mineral (data not shown). Moreover, immunostaining analysis demonstrated the presence of self-produced matrix which is positive for type I collagen (FIG. 8c). Thus, these results demonstrate that the CTPs of the present invention are capable of forming bone nodules containing calcium-phosphate deposits, the major component of bone minerals.

Altogether, these results demonstrate that adult stem cells-derived CTPs are capable of differentiating into cells of the osteogenic lineage while producing mineralized matrix.

Example 4

Human Adult Stem Cells-Derived CTP Cells are Capable of Differentiating Into the Chondrogenic Lineage To induce to chondrogenic differentiation, the two differentiation methods described under "General Materials and Experimental Methods" were employed.

Experimental Results

Induction of CTPs to Chondrogenic Differentiation Using the "Intact Layer" Method—

To induce chondrogenic differentiation, subconfluent cultures (passages 5-13) were trypsinized and placed as an intact layer in suspension, in the presence of the CTP medium. After 10 days the tissue was harvested for analysis. H&E staining showed round chondrocyte-like cells embedded in lacunae, at the periphery of the sample (FIG. 9a). Picro-sirius red staining demonstrated extensive collagenous matrix surrounding the cells (FIG. 9b).

Induction of CTPs to Chondrogenic Differentiation Using the Pellet Culture Method—

The induction of chondrogenic differentiation was further assessed using the pellet culture system of chondrogenic differentiation as published elsewhere (24). Cells (passages 1-9, of fetal derived CTPs, and passages 5, 10, 15-20, of fat-derived CTPs) were grown as pellet cultures in the presence of low serum TGF-$\beta 3$ supplemented medium as described in method 2 of chondrogenic differentiation in the General Materials and Experimental Methods, hereinabove. A section of one-month-old pellet culture was stained with Toluidine blue, showing the matrix proteoglycans (FIG. 10). Earlier pellet cultures were not positively stained (data not shown).

Altogether, these results demonstrate that adult stem cells-derived CTPs are capable of differentiating into the chondrogenic lineage while expressing cartilage markers.

Example 5

Enhanced Matrix Production by CTPS Seeded on Nanofiber Scaffolds

To provide cells with a suitable 3D environment that would support their growth and organization into a complex tissue, the electrospun, PCL/PLA nanofiber scaffolds were utilized, as follows Experimental Results Seeding of CTPs on Electrospun PCL/PLA Scaffolds Resulted in Connective Tissue Formation—

$5 \times 10^5$ CTPs (passage 10-12) resuspended in 10 µl of CTP medium were seeded on scaffolds and grown in the presence of the CTP medium for one month before harvesting for analysis. Histological analysis showed an high matrix to cell ratio (ECM-rich) connective tissue formation, with mesenchymal-like cells aligned in parallel, surrounded with extensive fibrous collagen matrix, with a thin remnant of the scaffold at the basal side of the construct, suggesting it has degraded over time (data not shown). Scanning electron microscopy illustrated the beginning of matrix production and a progressive tissue-like patches formation until a firm 3D sheet-like tissue is generated (data not shown). The presence of mineral deposits was confirmed by EDS analysis (data not shown). Cells grown in the same conditions but on plastic tissue culture plates did not show any form of 3D tissue-like formation (data not shown).

Altogether, these results demonstrate the ability of the adult stem cells derived CTPs of the present invention to form mineralized matrix and tissue-like patches when grown on nano-scaffolds.

Example 6

CTPS Are Capable of Forming Tendon Grafts in Vitro

To test the ability of the adult stem cells derived CTPs of the present invention to form a more compact and organized tissue, the long-term high-density culture technique was optimized, as follows.

CTP Cells are Capable of Forming a Tendon-Like Tissue—

The long-term high-density culture technique induces the self-assembly of 3D, cylinder-shaped constructs, which morphologically resemble early developed tendons. This process begins as a single cell attaching to the culture plate sidewall, forming fibrous matrix with a tendon-like shape. Adult stem cells derived CTPs from either a fat tissue (FIGS. 5a-f) or a fetal tissue (FIGS. 5g-m) which were cultured in the presence of CTP medium were capable of forming a tendon-like construct following 8 weeks in culture and a clear tendon tissue which grew up to 5 centimeters following 4 months in culture or 6-8 cm following 4-5 months (data not shown). Further immunostaining analyses demonstrated the progressive assembly of long, cylinder-shaped constructs which express type I collagen (data not shown). At a later developmental stage (following 2-3 weeks in culture), wider structures were observed (FIGS. 5c-e), until the formation of well defined, tendon-like constructs (FIG. 5f). Histological examination shows organized, parallel-aligned cells, with high matrix-to-cell ratio (data not shown). Additional SEM analyses of the tendon graft demonstrated well-defined fibrous structure and parallel orientation of elongated, fibroblast-like looking, cells (FIG. 5i, j and data not shown). Thus, these cells formed a well organized, highly cellular collagen-associated mineralized tissue, as evident by histology and electron microscopy (FIG. 5k, l, m and data not shown). Altogether, these experiments demonstrate the engineering of functional tendons from the adult stem cells derived CTPs of the present invention.

Evaluation of the Mechanical Properties of the Engineered Constructs Derived from the CTP Cells—

Three-month old constructs (made from fetal derived CTPs) were removed from the culture plate and were put into a custom built testing machine. The strain-stress response of the constructs resembles a non-linear behavior.

Altogether, these results demonstrate the formation of a tendon-like structure with excellent mechanical properties resembling that of mature rather than immature tendons.

Example 7

Adult Stem Cells Derived CTP Cells Form Connective Tissue In Vivo

To assess the commitment of the adult stem cells-derived CTP cells to the connective tissue lineage on one hand, and to examine their tumorigenic properties on the other hand, CTPs were transplanted into 6 SCID-beige mice, as follows.

CTP Cells are Non-Tumorigenic in Vivo—

Fetal derived CTPs from passages 5-6 or 10-11 were implanted underneath the kidney capsule of 5-week-old SCID-beige mice. Using this animal model, the present inventors have previously shown that undifferentiated hESCs are capable of forming teratomas (data not shown). Six and twelve weeks post transplantation, kidneys were harvested for analysis. Both macroscopic examination and histological analysis did not detect any form of teratoma formation (data not shown). Instead, a localized sub-capsular formation of loose connective tissue was observed, with no evidence of other tissue type (data not shown). Using this model, it is possible to explore the in-vivo developmental potential of adult stem cells-derived CTPs.

Altogether, these results demonstrate that adult stem cells-derived CTPs are non-tumorigenic and are committed to the connective cell lineage in vivo.

Example 8

CTP Cells Form Bone and Cartilage Tissues In Vivo

To assess the potential of the adult stem cells derived CTPs of the present invention to form cartilage and bone tissue in vivo, CTPs were subcutaneously transplanted into cd1 nude mice and the formation of ectopic new bone and cartilage was assessed, as follows.

CTP Derived Ectopic Transplants are Biocompatible, Well-Vascularized Masses with Radio-Opaque Bone Tissue—

For subcutaneous transplantation of adult stem cells derived CTPs, the mice were anesthetized and approximately 5 mm long incisions were made in 2 or 3 locations on the back of the animal. CTP cells from a single T75 flask (from either fetal or fat-derived CTPs) were injected in each incision. Ectopic transplants visible following 3 weeks of transplantation included bone tissue, as confirmed by the radio-opaque transplants seen by X-ray analysis (FIG. 4a and data not shown). Furthermore, X-ray analysis performed following 5 months of transplantation confirmed the formation of bone tissue (FIGS. 4b and c). It should be noted that the presence of bone tissue following 5 months of transplantation demonstrates that the CTPs underwent terminal differentiation to bone tissue and that the transplantation was not associated with a tumorigenic process. Close examination of the ectopic transplants following the removal of the back skin revealed the presence of non-cancerous, well-vascularized masses (FIGS. 11a-c), demonstrating that the ectopic transplant is biocompatible, well integrated within the recipient mouse and not rejected by its immune system.

CTP Derived Ectopic Transplants Include Bone and Cartilage Tissues—

Histological analyses of the ectopic transplants revealed the formation of new bone from CTPs derived from fetal tissue (data not shown) and hypertrophic cartilage (data not shown) tissues with early stage of mineralized bone matrix formation and a later stage showing osteon-like structures and new bone formation (data not shown).

CTP Derived Ectopic Transplants Include Mineralized Bone Tissue—

As is further shown in FIG. 12a, analysis of frozen sections of non-demineralized tissue demonstrated the formation of mineral deposits within the ectopic transplants of the adult stem cells derived CTPs (from fat tissue). In addition, H&E staining of histological sections derived from the ectopic transplant confirmed the formation of bone tissue (FIG. 12b).

CTP Derived Ectopic Transplants are of a Human Origin—

To verify that the ectopic transplants are derived from the adult stem cells derived CTPs from a fetal tissue histological sections of the ectopic transplants were subjected to immunostaining analysis using the anti-human mitochondria antibody (BioGenex, San Ramon, Calif., USA, Cat. No MU213-UC). The newly-formed ectopic tissue is positively stained with the anti-human mitochondria antibody (data not shown), demonstrating the human origin of the ectopic tissue.

Altogether, these results demonstrate the ability of the adult stem cells derived CTPs of the present invention to form bone and cartilage tissue in vivo.

Example 9

The In Vivo Repair of Critical Achilles-Tendon Injury Using a Tendon Graft Formed from Adult Stem Cells Derived CTPS To test the functionality of the in vitro engineered tendon graft from the adult stem cells derived CTPs of the present invention (as described in Example 6, hereinabove), the present inventors have induced a critical Achilles-tendon injury in mice and implanted the tendon graft of the present invention, as follow.

FIGS. 13a-e schematically depict the strategy of repairing a critical Achilles-tendon injury using the in vitro generated tendon graft of the present invention. High-density CTP cultures were grown with no further splitting for 4-5 weeks to form a sheet-like tissues in culture plates (FIG. 13a). Next tissues were gently removed from plates using a cell scraper and rolled to form rounded cylinders (FIG. 13b). Non-absorbable sutures were inserted at the ends of a construct through all layers (FIG. 13c). Constructs were immediately used for transplantation or kept inside custom-made templates made from flexible silicon tubes embedded in agar plates. Full thickness, 3-4 mm long segment of the Achilles tendon in nude mice was cut to form a critical gap (FIG. 13d). Next constructs were sutured to the proximal and distal edges of the injured Achilles tendon (FIG. 13e).

Experimental Results

In Vivo Repair of a Critical Achilles-Tendon Injury Using the in Vitro Formed Tendon Graft of the Present Invention—

Following the induction of a critical Achilles-tendon injury the treated mice are unable to extent their ankle, resulting in a maximal extension of less than 90 degrees (FIG. 14a). To repair the injury, adult stem cells derived CTPs from fetal and adult tissues are subjected to a high-density culture to form tendon grafts which are then implanted in the injured mice (FIG. 14b). One month after transplantation the implanted mice are capable of extending their leg with a maximal extension greater than 90 degrees (data not shown).

The Transplanted Tendon Grafts are Remodeled and Exhibit Excellent Biomechanical Properties—

Following 6-8 weeks of transplantation, the transplanted tendon grafts exhibit good integration at the sites of suturing (data not shown), with circulating blood vessels invading the graft (data not shown). Further histological evaluation of the transplanted grafts (generated from fetal derived CTPs) demonstrated that the grafts remodeled and integrated well (data not shown) with smoother edges. Further biomechanical testing using the tensile test machine demonstrated that the stress/strain behavior of the tendon graft (generated from fetal derived CTPs) after transplantation resembles that of a native rat tail tendon (data not shown).

The Transplanted Tendon Grafts are of a Human Origin—

To confirm the human origin of the transplanted tendon grafts (formed from fetal derived CTPs), a cross section of the transplanted tendon was subjected to immunostaining analysis using the anti-human mitochondria antibody. The transplanted tendon is positively stained with the anti-human mitochondria antibody, demonstrating its human origin (data not shown).

Example 10

Formation of ECM and Accelularized Matrix Using the Connective Tissue Progenitor Cells Experimental Results Formation of ECM in Vitro—

For the formation of extracellular matrix (ECM), the CTPs (from fat tissue) were plated at high densities ($5\text{-}10 \times 10^5$ cells/cm$^2$) in tissue culture plates in the presence of a culture medium comprising ascorbic acid and dexamethasone (CTP medium). After about 4 weeks in culture (other periods of time are also possible) sheet-like tissue was formed. The sheet-like tissue was subjected to freeze-drying and/or cell removal (FIGS. 15a-j). Freeze-drying was done using standard lyophilization device. The resultant tissue was completely devoid of viable cells as detecting using e.g., standard viability assays, thus reducing the risk of cell-based tumor formation and immune rejection.

Dry ECM Tissues are Biocompatible—

Dry tissues were stored at room temperature in dry conditions. The dry tissue formed was found to be biocompatible as evidenced by seeding the dry tissues with different cell types (e.g., Human embryonic kidney 293 cells) and observing the formation of secondary new tissue, as a model for allogenic cell seeding (FIGS. 16a-h, 17 and 18a-d).

The dried tissues were characterized by histology, immunostaining, electron microscopy and the results demonstrated that the ECM was kept intact, in a native form, supporting biological cellular activities (FIGS. 16a-f, 16g-h).

Acelularization of ECM—

Cell removal was done chemically with detergents such as SDS (0.1%, incubation time 20-60 minutes), combined with protease inhibitors, essentially as described in Cartmell J S. and Dunn M G., 2000, J. Biomed Mater. Res. 49(1): 134-40. Histology and electron microscopy assays show that the resultant tissue is completely acellular, while the ECM is preserved (FIGS. 16a, 16c, 16e, 18a-f).

Acelularized ECM Tissue is Biocompatible—

The biocompatibility of the acellular tissues was demonstrated by seeding different cell types onto the tissue, with the formation of secondary new tissue, as a model for allogenic cell seeding (FIGS. 16b, 16d, 16f, and 18a-i).

In addition, as is shown in FIGS. 19a-f, when transplanted in vivo the acellularized tissue (generated from fetal derived CTPs) is biocompatible as evidenced by histological staining of the tissue one week after transplantation with no signs of graft rejection.

Altogether, the freeze-dried and/or de-cellularized CTP-derived tissues are easy to handle and shape, suture retentive, can rapidly re-hydrate (indicates high hydrophilicity) and can be combined with standard hydrogels to make an injectable form.

It will be appreciated that the intact ECM can be conditioned by specific cell types, such as skin, skeletal muscle, cardiac muscle, fat, cartilage, bone, etc., to create tissue specific, specialized intact ECM tissues. This can be done by co-culturing CTPs with the second cell type before the formation of the primary tissue, or by seeding the second cell type onto the already processed CTP-derived tissue, allowing the cells to interact with the intact-ECM tissue, before secondary round of freeze-drying and/or cell removal will occur. Alternatively, the second cell type taken from the patient can be left to grow on the tissue prior to transplantation back into the patient.

Purified ECM Components—

Total protein component or selected proteins is purified from CTPs or CTP-derived tissues according to standard protein purification methods. The resultant protein is assessed by gel electrophoresis, western blotting and proteomics analysis. Such proteins are processed in order to achieve clinical-grade injectable formulas and other forms suitable for biomaterial applications.

Example 11

Adult Stem Cells Derived CTPS are Capable of Forming Fat Tissue

To further test the potential of CTPs which were generated from fat-tissue stem cells to form fat tissue, CTPs derived from any passage 1-20 were cultured in a culture medium containing αMEM supplemented with 15% FBS (selected lots), 0.5 mM 3-isobutyl-1-methylxanthine (IBMX), 10 µg/ml insulin, $10^{-6}$ M dexamethasone, and following 7-21 days in culture adipocytes were observed (FIG. 6a). To further test the potential of CTPs derived from another adult tissue to differentiate into the fat cell lineage, fetal derived CTPs were cultured in the same culture medium described hereinabove and following 7-14 days in culture adipocytes were observed (FIG. 6b).

Altogether, these results conclusively show that adult stem cells—derived CTPs can differentiate into fat tissue and form adipocytes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Additional References are Cited in Text

1. Vacanti, J. P. & Langer, R. (1999) Lancet 354, SI32-SI34.
2. Sharma, B. & Elisseeff, J. H. (2004) Ann Biomed Eng. 32, 148-159.
3. Muschler, G. F., Nakamoto, C. & Griffith, L. G. (2004) J Bone Joint Surg Am. 86, 1541-1558.
4. Lavik, E. & Langer, R. (2004) Appl Microbiol Biotechnol 65, 1-8.
5. Betz, R. R. (2002) Orthopedics. 25, s561-s570.
6. Meyer, U., Joos, U. & Wiesmann, H. P. (2004) Int J Oral Maxillofac Surg 33, 325-332.
7. Muschler, G. F. & Midura, R. J. (2002) Clin Orthop Relat Res 66-80.
8. Sottile, V., Halleux, C., Bassilana, F., Keller, H. & Seuwen, K. (2002) Bone 30, 699-704.
9. Pittenger, M. F., Mackay, A. M., Beck, S. C., Jaiswal, R. K., Douglas, R., Mosca, J. D., Moorman, M. A., Simonetti, D. W., Craig, S, & Marshak, D. R. (1999) Science 284, 143-147.
10. Mastrogiacomo, M., Derubeis, A. R. & Cancedda R. (2005) J Cell Physiol 204, 594-603.
11. Zuk, P. A., Zhu, M., Mizuno, H., Huang, J., Futrell. J. W, Katz, A. J., Benhaim, P., Lorenz, H. P. & Hedrick, M. H. (2001) Tissue Eng 7, 211-228.
12. Thomson, J. A., Itskovitz-Eldor, J., Shapiro, S. S., Waknitz, M. A., Swiergiel, J. J., Marshall, V. S. & Jones, J. M. (1998) Science 282, 1145-1147.
13. Itskovitz-Eldor, J., Schuldiner, M., Karsenti, D., Eden, A., Yanuka, O., Amit, M., Soreq, H. & Benvenisty, N. (2000) Mol Med 6, 88-95.
14. Schuldiner, M., Yanuka. O., Itskovitz-Eldor. J., Melton, D. A. & Benvenisty, N. (2000) Proc Natl Acad Sci USA 97, 11307-11312.
15. Hwang, W. S., Roh, S. I., Lee, B. C., Kang, S. K., Kwon, D. K., Kim, S., Kim, S. J., Park, S. W., Kwon, H. S., Lee, C. K. et al. (2005) Science 308, 1777-1783.
16. Levenberg, S., Huang, N. F., Lavik, E., Rogers, A. B., Itskovitz-Eldor, J. & Langer, R. (2003) Proc Natl Acad Sci USA. 100, 12741-12746.
17. Gerecht-Nir, S., Cohen, S., Ziskind, A. & Itskovitz-Eldor, J (2004) Biotechnol Bioeng. 88, 313-320.
18. Cao, T., Heng, B. C., Ye, C. P., Liu, H., Toh, W. S., Robson, P., Li, P., Hong, Y. H. & Stanton, L. W. (2005) Tissue Cell 37, 325-334.
19. Bielby, R. C., Boccaccini, A. R., Polak, J. M. & Buttery L. D. (2004) Tissue Eng 10, 1518-1525.
20. Sottile, V., Thomson, A. & McWhir, J. (2003) Cloning Stem Cells 5, 149-155.
21. Barberi, T., Willis, L. M., Socci, N. D. & Studer, L. (2005) PLoS Med 2, e161
22. Amit, M., Carpenter, M. K., Inokuma, M. S., Chiu, C. P., Harris, C. P., Waknitz, M. A., Itskovitz-Eldor, J. & Thomson, J. A. (2000) Dev Biol 227, 271-278.

23. Montjovent, M. O., Burri, N., Mark, S., Federici, E., Scaletta, C., Zambelli, P. Y., Hohlfeld, P., Leyvraz, P. F., Applegate, L. L. & Pioletti, D. P. (2004) Bone 35, 1323-1333.
24. Kim, M. S., Hwang, N. S., Lee, J., Kim, T. K., Leong, K., Shamblott, M. J., Gearhart, J. & Elisseeff, J. (2005) Stem Cells 23, 113-123.
25. Hyllested, J. L., Veje, K. & Ostergaard, K. (2002) Osteoarthritis Cartilage 10, 333-343.
26. Ma, Z., Kotaki, M., Inai, R. & Ramakrishna S. (2005) Tissue Eng 11, 101-109.
27. Maniatopoulos, C., Sodek, J. & Melcher, A. H. (1988) Cell Tissue Res 254, 317-330.
28. Coelho, M. J. & Fernandes, M. H. (2000) Biomaterials 21, 1095-1102.
29. Smith, N., Dong, Y., Lian, J. B., Pratap, J., Kingsley, P. D., van Wijnen, A. J., Stein, J. L., Schwarz, E. M., O'Keefe, R. J., Stein, G. S. et al (2005) Cell Physiol 203, 133-143.
30. Rossert, J., Terraz, C. & Dupont, S. (2000) Nephrol Dial Transplant 15, Suppl. 66-88.
31. Bellows, C. G., Aubin, J. E. & Heersche, J. N. (1991) Bone Miner 14, 27-40.
32. Sodek, J., Ganss, B. & McKee, M. D. (2000) Crit Rev Oral Biol Med 11, 279-303
33. Mannstadt, M., Juppner, H. & Gardella, T. J. (1999) Am J Physiol 277, F665-F675.
34. Sperger, J. M., Chen, X., Draper, J. S., Antosiewicz, J. E., Chon, C. H., Jones, S. B., Brooks, J. D., Andrews, P. W., Brown, P. O. & Thomson, J. A. (2003) Proc Natl Acad Sci USA 100, 13350-13355.
35. Golan-Mashiach, M., Dazard, J. E., Gerecht-Nir, S., Amariglio, N., Fisher, T., Jacob-Hirsch, J., Bielorai, B., Osenberg, S., Barad, O., Getz, G. et al (2005) FASEB J 19, 147-149.
36. Bhattacharya, B., Miura, T., Brandenberger, R., Mejido, J., Luo, Y., Yang, A. X., Joshi, B. H., Ginis, I., Thies, R. S., Amit, M. et al (2004) Blood 103, 2956-2964.
37. Zipori, d. (2004) Nat Rev Genet 5, 873-878.
38. Karabela-Bouropoulou, V., Markaki, S. & Milas, C. (1988) Pathol Res Pract 183, 761-766.
39. Reichenberger, E., Aigner, T., von der Mark, K., Stoss, H. & Bertling, W. (1991) Dev Biol 148, 562-572.
40. Levine, J. M. & Nishiyama, A. (1996) Perspect Dev Neurobiol, 3, 245-259.
41. Hedbom, E., Antonsson, P., Hjerpe, A., Aeschlimann, D., Paulsson, M., Rosa-Pimentel, E., Sommarin, Y., Wendel, M., Oldberg, A. & Heinegard, D. (1992) J Biol Chem 267, 6132-6136.
42. Dvash, T. & Benvenisty, N. (2004) Best Pract Res Clin Obstet Gynaecol 18, 929-940.
43. Mistry, A. S. & Mikos, A. G. (2005) Adv Biochem Eng Biotechnol 94, 1-22.
44. Noth, U., Osyczka, A. M., Tuli, R., Hickok, N. J., Danielson, K. G. & Tuan, R. S. (2002) J Orthop Res 20, 1060-1069.
45. Aigner, T. & Stove, J. (2003) Adv Drug Deliv Rev 55, 1569-1593.
46. Scott, J. E. (2003) J Physiol 553, 335-343.
47. Cell Junctions, Cell Adhesion, and the Extracellular Matrix (1994) in Molecular Biology of the Cell, eds. Alberts, B., Johnson, A., Lewis, J., Raff, M., Roberts, K. & Walter, P. (Garland Publishing), pp. 971-995.
48. Yoshimoto, H., Shin, Y. M., Terai, H. & Vacanti, J. P. (2003) Biomaterials 24, 2077-2282.
49. Canty, E. G. & Kadler, K. E. (2002) Comp Biochem Physiol A Mol Integr Physiol 133, 979-985.
50. Brent, A. E., Schweitzer, R. & Tabin, C. J. (2003) Cell 113, 235-248.
51. Brent, A. E., Braun, T. & Tabin, C. J. (2005) Development 132, 515-528.
52. Vunjak-Novakovic, G., Altman, G., Horan, R. & Kaplan, D. L. (2004) Annu Rev Biomed Eng 6, 131-156.
53. Van Eijk, F., Saris, D. B., Riesle, J., Willems, W. J., Van Blitterswijk, C. A., Verbout, A. J. & Dhert, W. J. (2004) Tissue Eng 10, 893-903.
54. Calve, S., Dennis, R. G., Kosnik, P. E. 2nd, Baar, K., Grosh, K. & Arruda, E. M. (2004) Tissue Eng 10, 755-761.
55. Grenier, G., Remy-Zolghadri, M., Larouche, D., Gauvin, R., Baker, K., Bergeron, F., Dupuis, D., Langelier, E., Rancourt, D., Auger, F. A. et al (2005) Tissue Eng 11, 90-100.
56. Lee, C. H., Shin, H. J., Cho, I. H., Kang, Y. M., Kim, I. A., Park, K. D. & Shin, J. W. (2005) Biomaterials 26, 1261-1270.
57. Cartmell, J. S. & Dunn, M. G. (2000) J Biomed Mater Res 49, 134-140.
58. Wren, T. A., Lindsey, D. P., Beaupre, G. S. & Carter, D. R. (2003) Ann Biomed Eng 31, 710-717.

What is claimed is:

1. A method of generating a tendon in vitro, comprising:
   (a) culturing connective tissue progenitor cells in the absence of a scaffold or a carrier to thereby obtain a sheet-like tissue, and
   (b) rolling and/or folding said sheet-like tissue to form a rounded cylinder,
   thereby generating the tendon tissue in vitro.

2. The method of claim 1, wherein said culturing is performed in a culture medium which comprises ascorbic acid and/or dexamethasone.

3. The method of claim 1, wherein said culturing is effected without culture splitting.

4. The method of claim 3, wherein said culturing without said culture splitting is effected for about 4-5 weeks.

5. The method of claim 1, further comprising removing said sheet-like tissue from said culturing vessel prior to said rolling and/or to said folding of said sheet-like tissue.

6. The method of claim 5, wherein said removing is effected using a scraper.

7. The method of claim 1, wherein said connective tissue progenitor cells are capable of differentiating into at least two cell lineages of a connective tissue.

8. The method of claim 7, wherein said at least two cell lineages of said connective tissue are selected from the group consisting of an osteogenic lineage, a chondrogenic lineage, an adipocytic lineage and a tendon and ligament lineage.

9. The method of claim 1, wherein said culturing is effected at a cell density of about $5\text{-}10 \times 10^5$ cells/cm$^2$.

10. The method of claim 2, wherein said culture medium further comprises serum or serum replacement.

11. The method of claim 1, wherein said connective tissue progenitor cells express CD105, CD166, CD44, CD29 and HLA-ABC.

12. The method of claim 1, wherein said connective tissue progenitor cells not expressing CD45 and HLA-DR.

13. The method of claim 1, wherein said connective tissue progenitor cells express core binding factor alpha 1 (CBFA1).

14. The method of claim 1, wherein said connective tissue progenitor cells are devoid of feeder cells.

15. The method of claim 1, wherein said connective tissue progenitor cells are xeno-free.

* * * * *

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ccgcacgaca accgcaccat                                                     20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide
```

```
<400> SEQUENCE: 2
cgctccggcc cacaaatctc                                               20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
atctgaagaa ggagagcgag                                               20

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
tcagaagtct ccagagcttg                                               20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
gcacacaatg gattgcaagg                                               20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
taaccactgc tccactctgg                                               20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
gcagcaatga caacaagacc                                               20

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
cttctcattc tcatggatct tc                                            22

<210> SEQ ID NO 9
<211> LENGTH: 23
<212> TYPE: DNA
```

```
<213> ORGANISM: Artificial sequence
<220> FEATURE:
<223> OTHER INFORMATION: Single strand DNA oligonucleotide

<400> SEQUENCE: 9
ctaggcatca cctgtgccat acc                                         23

<210> SEQ ID NO 10
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 10
cagtgaccag ttcatcagat tcatc                                       25

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
tggagcttca gaagctcaac                                             20

<210> SEQ ID NO 12
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 12
atctcgttgt ctgagtagta ccagtcc                                     27

<210> SEQ ID NO 13
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 13
cacagcctca tcttcatgg                                              19

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
gcatctcata gtgcatctgg                                             20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
tggtttaact ggagccaagg                                             20
```

-continued

```
<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
gcccaccatg aatttatatc                                              20

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17 cccttttgc tgctagtatc c                                             21

<210> SEQ ID NO 18
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 18
ctgttgtcca ggttttcctg gcac                                         24

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
caggacgact ttgatgcaga                                              20

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
aagctggagc tgtcctggta                                              20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
atccgagaca ccaacgagac                                              20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide
```

```
<400> SEQUENCE: 22
ggcttcaccc tcactgatgt                                              20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
cccccatcct cactacaaac                                              20

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
atccagggtt cctctgtgtg                                              20

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
tgcaagcttc cctttcagt                                               20

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
ctgcacagcc gaaattgtaa                                              20

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
cctccaactg ctcctactcg                                              20

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
cgggtctacc tgattctcca                                              20

<210> SEQ ID NO 29
<211> LENGTH: 20
<212> TYPE: DNA
```

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
gtgcctggac tgatttggtt                                               20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
tgtggaggca atttgtttga                                               20

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
tgaagaacct tcacgcattg                                               20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
gagccattgt caacagcaga                                               20

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
tgcagaacaa cgacatctcc                                               20

<210> SEQ ID NO 34
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 34
ccaggttcaa agccactgtt                                               20

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
gctatggact gccctacacc                                               20

```
<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
agctcctggg acaccaacta                                              20

<210> SEQ ID NO 37
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 37
ggagtcagct gccaagagac                                              20

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
acacacgtgc acctcatcat                                              20

<210> SEQ ID NO 39
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 39
cgtggagtac cttgtcagca                                              20

<210> SEQ ID NO 40
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 40
aggtaaccgg tgactgatgc                                              20
```